(12) United States Patent  
Srinivasan et al.

(10) Patent No.: US 11,626,210 B2  
(45) Date of Patent: Apr. 11, 2023

(54) DIGITAL HEALTH PROGNOSTIC ANALYZER FOR MULTIPLE MYELOMA MORTALITY PREDICTIONS

(71) Applicant: Celgene Corporation, Summit, NJ (US)

(72) Inventors: Shankar Swamimalai Srinivasan, Hillsborough, NJ (US); Albert Elion-Mboussa, North Plainfield, NJ (US)

(73) Assignee: Celgene Corporation, Summit, NJ (US)

( * ) Notice: Subject to any disclaimer, the term of this patent is extended or adjusted under 35 U.S.C. 154(b) by 432 days.

(21) Appl. No.: 16/345,152

(22) PCT Filed: Oct. 30, 2017

(86) PCT No.: PCT/US2017/059008  
§ 371 (c)(1),  
(2) Date: Apr. 25, 2019

(87) PCT Pub. No.: WO2018/081696  
PCT Pub. Date: May 3, 2018

(65) Prior Publication Data  
US 2019/0287683 A1 Sep. 19, 2019

Related U.S. Application Data

(60) Provisional application No. 62/414,975, filed on Oct. 31, 2016.

(51) Int. Cl.  
*G16H 50/30* (2018.01)  
*G16H 50/50* (2018.01)  
(Continued)

(52) U.S. Cl.  
CPC .......... *G16H 50/30* (2018.01); *G06N 20/00* (2019.01); *G16H 50/20* (2018.01); *G16H 50/50* (2018.01); *Y02A 90/10* (2018.01)

(58) Field of Classification Search  
CPC ........ G16H 50/30; G16H 50/50; G16H 50/20; G16H 20/00; Y02A 90/10  
(Continued)

(56) References Cited

U.S. PATENT DOCUMENTS

| 2010/0057651 A1* | 3/2010 | Fung | G06N 7/005 |
| | | | 706/54 |
| 2013/0132323 A1* | 5/2013 | Soto | G16H 15/00 |
| | | | 706/47 |

FOREIGN PATENT DOCUMENTS

WO WO-2013009890 A2 * 1/2013 ............. G16H 70/20

OTHER PUBLICATIONS

Biran, N., Jagannath, S.,&Chari,A. (2013). Riskstratificationinmultiplemyeloma,part1:characterizationofhigh-riskdisease. ClinAdvHematolOncol,11(8),489-503. (Year: 2013).*

(Continued)

*Primary Examiner* — Joshua B Blanchette  
*Assistant Examiner* — Winston Furtado  
(74) *Attorney, Agent, or Firm* — Jones Day

(57) ABSTRACT

Computer-implemented systems and methods are provided for constructing a numerical model to generate a probability that a patient diagnosed with multiple myeloma will die within a predetermined period of time. Reference data for a plurality of patients diagnosed with multiple myeloma is received. First variables selected from the reference data are deemed predictive of mortality for a first predetermined period of time, and second variables selected from the reference data are deemed predictive of mortality for a second predetermined period of time. A first computer (Continued)

model comprising a combination of variables of the first selected variables and first weighting factors is generated. A second computer model comprising a combination of variables of the second selected variables and second weighting factors is generated. The first computer model and the second computer model are trained using the reference data to determine numerical values for the respective first and second weighting factors.

37 Claims, 32 Drawing Sheets

(51) Int. Cl.
    *G16H 50/20*     (2018.01)
    *G06N 20/00*     (2019.01)
(58) Field of Classification Search
    USPC .......................................................... 705/2
    See application file for complete search history.

(56) References Cited

OTHER PUBLICATIONS

Chen,S.X.(1998). Weightedpolynomialmodelsandweightedsamplingschemesforfinitepopulation.TheAnnalsofStatistics,26(5), 1894-1915. (Year: 1998).*

Rajkumar, S. V. (2016). Multiple myeloma: 2016 update on diagnosis, risk-stratification, and management. American journal of hematology, 91(7), 719-734. (Year: 2016).*

Joseph Mikael, et al.; Management of Newly Diagnosed Symptomatic Multiple Myeloma: Updated Mayo Stratification of Myeloma and Risk-Adapted Therapy (mSMART) Consensus Guidelines 2013; Mayo Clinic Proceedings; Apr. 2013; pp. 360-376; vol. 88(4).

Mark Levine, Jim Julian; Registries That Show Efficacy: Good, but Not Good Enough; Journal of Clinical Oncology; Nov. 2008; pp. 5316-5319; vol. 26(33).

Richard Gliklich, Nancy Dreyer, Michelle Leavy, eds.; Registries for Evaluating Patient Outcomes: A User's Guide, 3d Edition; Apr. 2014; Agency for Healthcare Research and Quality; Rockville, Maryland.

K. Yoshida, et al.; Use of Data From Multiple Registries in Studying Biologic Discontinuation: Challenges and Opportunities; Clinical and Experimental Rheumatology; Aug. 2013; pp. S28-S32; vol. 31(Suppl. 78).

A. Larocca, et al.; Early Mortality in Elderly Patients with Newly Diagnosed Multiple Myeloma Treated with Novel Agents; 15th International Myeloma Workshop: Clinical Lymphoma, Myeloma & Leukemia; Sep. 2015; pp. e42-e43.

Howard Terebelo, et al.; Development of a Prognostic Model for Overall Survival in Multiple Myeloma Using the Connect MM Patient Registry; British Journal of Haematology; Jun. 2019; 13 pages; John Wiley & Sons Ltd.

Noa Biran, et al.; Risk Stratification in Multiple Myeloma, Part 2: The Significance of Genetic Risk Factors in the Era of Currently Available Therapies; Clinical Advances in Hematology & Oncology; Sep. 2013; pp. 578-583; vol. 11 (9).

Athanasios Anagnostopoulos, et al.; Multiple Myeloma in Elderly Patients: Prognostic Factors and Outcome; European Journal of Haematology; Nov. 2005; pp. 370-375; vol. 75(5).

Michael Attal, et al.; Lenalidomide, Bortezomib, and Dexamethasone with Transplantation for Myeloma; The New England Journal of Medicine; Apr. 2017; pp. 1311-1320; vol. 376.

Ashraf Badros; In the Age of Novel Therapies, What Defines High-Risk Multiple Myeloma?; Journal of the National Comprehensive Cancer Network; Feb. 2010; pp. S28-S34; vol. 8, Supplement 1.

Robert Bendel, A. Afifi; Comparison of Stopping Rules in Forward "Stepwise" Regression; Journal of the American Statistical Association; 1977; pp. 46-53; vol. 72(357).

P.L. Bergsagel; Where We Were, Where We Are, Where We Are Going: Progress in Multiple Myeloma; American Society of Clinical Oncology Educational Book; Jun. 2014; pp. 199-203.

Zoran Byrsac, et al.; Purposeful Selection of Variables in Logistic Regression; Source Code for Biology and Medicine; Dec. 2008; vol. 3(17).

J. Anthony Child, et al.; High-Dose Chemotherapy with Hematopoietic Stem-Cell Rescue for Multiple Myeloma; The New England Journal of Medicine; May 2003; pp. 1875-1883; vol. 348.

Brian G.M. Durie, et al.; Bortezomib With Lenalidomide and Dexamethasone Versus Lenalidomide and Dexamethasone Alone in Patients with Newly Diagnosed Myeloma Without Intent for Immediate Autologous Stem-cell Transplant (SWOG S0777): a Randomised, Open-Label, Phase 3 Trial; Lancet; Feb. 2017; pp. 519-527; vol. 389.

Thierry Facon; Phase 3 Randomized Study of Daratumumab Plus Lenalidomide and Dexamethasone (D-Rd) Versus Lenalidomide and Dexamethasone (Rd) in Patients with Newly Diagnosed Multiple Myeloma (NDMM) Ineligible for Transplant (MAIA); Blood; 2018; p. LBA-2; vol. 132.

R. Fonseca, et al.; Trends in Overall Survival and Costs of Multiple Myeloma, 2000-2014; Leukemia; 2017; pp. 1915-1921; vol. 31.

Francesca Gay, et al.; Carfilzomib-Lenalidomide-Dexamethasone (KRd) Induction-Autologous Transplant (ASCT)-Krd Consolidation Vs KRd 12 Cycles Vs Carfilzomib-Cyclophosphamide-Dexamethasone (KCd) Induction-ASCT-KCd Consolidation: Analysis of the Randomized Forte Trial in Newly Diagnosed Multiple Myeloma (NDMM); Blood; 2018; p. 121; vol. 132.

John W. Graham, et al.; How Many Imputations are Really Needed? Some Practical Clarifications of Multiple Imputation Theory; Prevention Science; Jun. 2007; pp. 206-213; vol. 8(3).

Philip R. Greipp, et al.; International Staging System for Multiple Myeloma; Journal of Clinical Oncology; May 2005; pp. 3412-3420; vol. 23(15).

Susan Halabi, Kouros Owzar; The Importance of Identifying and Validating Prognostic Factors in Oncology; Seminars in Oncology; Apr. 2010; pp. e9-e18; vol. 37(2).

Amr Hanbali, et al.; The Evolution of Prognostic Factors in Multiple Myeloma; Advances in Hematology; Feb. 2017; 11 pages; vol. 2017(6).

Jean Luc Harousseau, Michel Attal; How I Treat First Relapse of Myeloma; Blood; 2017; pp. 963-973; vol. 130.

N.L. Henry; Clinical Importance of Prognostic Factors: Moving from Scientifically Interesting to Clinically Useful; In Principles of Molecular Oncology; 2008; Human Press Inc; Totowa, NJ.

Sundar Jagannath, et al.; Treatment Choices and Outcomes for Patients with Multiple Myeloma after Relapse on Lenalidomide Maintenance Therapy: Results from the Connect® MM Registry; Blood; 2018; p. 3232; vol. 132.

Andrzej Jakubowiak, et al.; A Phase 1/2 Study of Carfilzomib in Combination with Lenalidomide and Low-Dose Dexamethasone as a Frontline Treatment for Multiple Myeloma; Blood; Aug. 2012; pp. 1801-1809; vol. 120(9).

Efstathios Kastritis, et al.; Evaluation of the Revised International Staging System in an Independent Cohort of Unselected Patients with Multiple Myeloma; Haematologica; 2017; pp. 593-599; vol. 102(3).

R.A. Kyle, S.V. Rajkumar; Criteria for Diagnosis, Staging, Risk Stratification and Response Assessment of Multiple Myeloma; Leukemia; 2009; pp. 3-9; vol. 23(1).

Eric Maiese, et al.; Temporal Trends in Survival and Healthcare Costs in Patients with Multiple Myeloma in the United States; American Health & Drug Benefits; Feb. 2018; pp. 39-46; vol. 11(1).

Philip McCarthy, et al.; Lenalidomide Maintenance After Autologous Stem-Cell Transplantation in Newly Diagnosed Multiple Myeloma: A Meta-Analysis; Journal of Clinical Oncology; Oct. 2017; pp. 3279-3289; vol. 35(29).

Ruth Mickey, Sander Greenland; The Impact of Confounder Selection Criteria on Effect Estimation; American Journal of Epidemiology; Jan. 1989; pp. 125-137; vol. 129(1).

(56) References Cited

OTHER PUBLICATIONS

Philippe Moreau, et al.; Oral Ixazomib, Lenalidomide, and Dexamethasone for Multiple Myeloma; The New England Journal of Medicine; Apr. 2016; pp. 1621-1634; vol. 374(17).
Blase Polite, et al.; Charting the Future of Cancer Health Disparities Research: A Position Statement From the American Association for Cancer Research, the American Cancer Society, the American Society of Clinical Oncology, and the National Cancer Institute; Journal of Clinical Oncology; Sep. 2017; 10 pages; vol. 35(26).
S. Vincent Rajkumar; Multiple Myeloma: 2016 Update on Diagnosis, Risk-Stratification, and Management; American Journal of Hematology; Jul. 2016; pp. 719-734; vol. 91(7).
S. Vincent Rajkumar, S. Kumar; Multiple Myeloma: Diagnosis and Treatment; Mayo Clinic Proceedings; Jan. 2016; pp. 101-1019; vol. 91(1).
S. Vincent Rajkumar, R.A. Kyle; Multiple Myeloma: Diagnosis and Treatment; Mayo Clinic Proceedings; Oct. 2005; pp. 1371-1382; vol. 80(10).
Shahzad Razs, et al.; Optimizing Current and Emerging Therapies in Multiple Myeloma: A Guide for the Hematologist; Therapeutic Advances in Hematology; 2017; pp. 55-70; vol. 8(2).
Murielle Roussel, et al.; Front-Line Transplantation Program With Lenalidomide, Bortezomib, and Dexamethasone Combination As Induction and Consolidation Followed by Lenalidomide Maintenance in Patients With Multiple Myeloma: A Phase II Study by the Intergroupe Francophone du Myelome; Journal of Clinical Oncology; Sep. 2014; pp. 2712-2717; vol. 32(25).
Donald Rubin; Multiple Imputation for Nonresponse in Surveys; 1987; John Wiley & Sons; New York, NY.
Jesus San Miguel, et al.; Bortezomib plus Melphalan and Prednisone for Initial Treatment of Multiple Myeloma; The New England Journal of Medicine; Aug. 2008; pp. 906-917; vol. 359.
Pieter Sonneveld, et al.; Treatment of Multiple Myeloma with High-Risk Cytogenetics: a Consensus of the International Myeloma Working Group; Blood; 2016; pp. 2955-2962; vol. 127(24).
Joan Warren, et al.; Multiple Myeloma Treatment Transformed: A Population-Based Study of Changes in Initial Management Approaches in the United States; Journal of Clinical Oncology; Jun. 2013; pp. 1984-1989; vol. 31(16).
W. Wu, et al.; The Association of Diabetes and Anti-Diabetic Medications with Clinical Outcomes in Multiple Myeloma; British Journal of Cancer; Jul. 2014; pp. 628-636; vol. 111 (3).
Shankar S. Srinivasan, et al.; Validation, Multivariate Modeling, and the Construction of Heat-Map Prediction Matrices for Survival in the Context of Missing Data; Ch. 17 in Biopharmaceutical Applied Statistics Symposium; Sep. 2018; pp. 353-374; Springer: Singapore.
Paul D. Allison; Estimating Survivor Functions; In: Survival Analysis Using SAS: A Practical Guide (2d ed.); 2010; pp. 186-192; SAS Institute, Inc.: Cary, NC.
Lotfi Benboubker, et al.; Lenalidomide and Dexamethasone in Transplant-Ineligible Patients with Myeloma; The New England Journal of Medicine; Sep. 2014; pp. 906-917; vol. 371(10).
James A. Hanley, Barbara J. McNeil; The Meaning and Use of the Area under a Receiver Operating Characteristic (ROC) Curve; Radiology; Apr. 1982; pp. 29-36; vol. 143.
Frank E. Harrell; Quantifying Predictive Ability; In: Regression Modeling Strategies with Applications to Linear Models, Logistic Regression and Survival Analysis; 2001; pp. 247-253; Springer: New York.
R.J.A. Little, D.B. Rubin; Introduction to Multiple Imputation; In: Statistical Analysis with Missing Data (2d ed.); 2002; pp. 85-89; Wiley: Hoboken, New Jersey.
Patricia Bergland, Steven Herringa; Introduction to Multiple Imputation Theory and Methods; Ch. 2 in Multiple Imputation of Missing Data Using SAS; 2014; pp. 11-18; SAS Institute: Inc., Cary, NC.
Michael J. Pencina, Ralph B. D'agostino; Overall C as a Measure of Discrimination in Survival Analysis: Model Specific Population Value and Confidence Interval Estimation; Statistics in Medicine; Jun. 2004; pp. 2109-2123; vol. 23.

Robert M. Rifkin, et al.; Connect MM Registry: The Importance of Establishing Baseline Disease Characteristics; Clinical Lymphoma Myeloma and Leukemia; Jun. 2015; pp. 368-376; vol. 15(6).
Jatin J. Shah, et al.; Analysis of Common Eligibility Criteria of Randomized Controlled Trials in Newly Diagnosed Multiple Myeloma Patients and Extrapolating Outcomes; Clinical Lymphoma, Myeloma and Leukemia; Sep. 2017; pp. 575-583; vol. 17(9).
M.E. Stokes, et al.; Logistic Regression I: Dichotomous Response; Ch. 8 in Categorical Data Analysis Using SAS (3d ed.); 2012; pp. 165-175; SAS Institute, Inc.: Cary, NC.
Howard Terebelo, et al.; Recognition of Early Mortality in Multiple Myeloma by a Prediction Matrix; American Journal of Hematology; Sep. 2017; pp. 915-923; vol. 92(9).
Carol Townsley, et al.; Systematic Review of Barriers to the Recruitment of Older Patients With Cancer Onto Clinical Trials; Journal of Clinical Oncology; May 2005; pp. 312-3124; vol. 23(13).
Joseph M. Unger, et al.; Comparison of Survival Outcomes Among Cancer Patients Treated In and Out of Clinical Trials; Journal of the National Cancer Institute; Mar. 2014; 13 pages; vol. 106(3).
Stef van Buuren; Multiple Imputation of Discrete and Continuous Data By Fully Conditional Specification; Statistical Methods in Medical Research; Jun. 2007; pp. 219-242; vol. 16.
Nathan Vastesaeger, et al.; A Pilot Risk Model for the Prediction of Rapid Radiographic Progression in Rheumatoid Arthritis; Rheumatology; Jul. 2009; pp. 1114-1121; vol. 48.
Nathan Vastesaeger, et al.; Predicting the Outcome of Ankylosing Spondylitis Therapy; Annals of Rheumatic Diseases; Mar. 2011; pp. 973-981; vol. 70.
G.E. Vist, et al.; Outcomes of Patients Who Participate in Randomized Controlled Trials Compared to Similar Patients Receiving Similar Interventions Who Do Not Participate (Review); Cochrane Database of Systematic Reviews; 2008; 106 pages; vol. 3.
Angela M. Wood, et al.; How Should Variable Selection Be Performed With Multiply Imputed Data?; Statistics in Medicine; Jul. 2008; pp. 3227-3246; vol. 27(17).
Yang Yuan; Multiple Imputation for Missing Data: Concepts and New Development; In Proceedings of SUGI-25; Jan. 2005; 13 pages.
H. Murakami, et al.; Risk Factors for Early Death in Patients Undergoing Treatment for Multiple Myeloma; Annals of Hematology; Aug. 2001; pp. 452-455; vol. 80(8).
Efstathios Kastritis, et al.; Very Early Death (<2 months) In Myeloma Is Associated With Advanced Age, Poor Performance Status and Reducted Use of Novel Agents, While Early Death Within 12 Months Is Associated With High Risk Features Of Both The Disease and the Patient; American Society of Hematology; 2013; Abstract 3195; vol. 122 (21).
Noa Biran, et al.; Risk Stratification in Multiple Myeloma, Part 1: Characterization of High-Risk Disease; Clinical Advances in Hematology & Oncology; Aug. 2013; pp. 489-503; vol. 11(8).
M.D. Alessandra Larocca, et al.; Early Mortality in Elderly Newly Diagnosed Multiple Myeloma Patients Treated with Novel Agents: A Pooled Analysis of Two Large Randomized Phase III Trials; 20th Congress of the European Hematology Association; Jun. 2015; Abstract P270.
Bradley M. Augustson, et al.; Early Mortality After Diagnosis of Multiple Myeloma: Analysis of Patients Entered Onto the United Kingdom Medical Research Council Trials Between 1980 and 2002—Medical Research Council Adult Leukemia Working Party; Journal of Clinical Oncology; Dec. 2005; pp. 9219-9226; vol. 23(36).
Vishal Rana, et al.; Factors Predicting Eady Modality in Patients with Newly Diagnosed Multiple Myeloma; American Society of Hematology; 2011; Abstract 3981; vol. 118(21).
Philippe Moreau, et al.; Combination of International Scoring System 3, High Lactate Dehydrogenase, and t(4;14) and/or del(17p) Identifies Patients with Multiple Myeloma (MM) Treated with Front-Line Autologous Stem-Cell Transplantation at High Risk of Eady MM Progression-Related Death; Journal of Clinical Oncology; Jul. 2014; pp. 2173-2180; vol. 32(20).
R.M. Conroy, et al.; Estimation of Ten-Year Risk of Fatal Cardiovascular Disease in Europe: the SCORE Project European Head Journal; 2003; pp. 987-1003; vol. 24(11).

(56) References Cited

OTHER PUBLICATIONS

Frederick R. Appelbaum, et al.; Age and Acute Myeloid Leukemia; Blood; May 2006; pp. 3481-3485; vol. 107(9).

Andreas Rosenwald, et al.; The Use of Molecular Profiling to Predict Survival After Chemotherapy for Diffuse Large-B-Cell Lymphoma; New England Journal of Medicine; Jun. 2002; pp. 1937-1947; vol. 346(25).

Chieh Lin, et al.; Eady 18F-FDG PET for Prediction of Prognosis in Patients with Diffuse Large B-Cell Lymphoma: SUV-Based Assessment Versus Visual Analysis; The Journal of Nuclear Medicine; Oct. 2007; pp. 1626-1632; vol. 48(10).

S. Ozaki, et al.; Survival of Multiple Myeloma Patients Aged 65-70 Years in the Era of Novel Agents and Autologous Stem Cell Transplantation: A Multicenter Retrospective Collaborative Study of the Japanese Society of Myeloma and the European Myeloma Network; Acta Haematologica; Jan. 2014; pp. 211-219; vol. 132(2).

Shaji K. Kumar, et al.; Continued Improvement in Survival in Multiple Myeloma: Changes in Eady Modality and Outcomes in Older Patients; Leukemia; 2014; pp. 1122-1128; vol. 28(5).

L.J. Costa, et al.; Early Mortality in Multiple Myeloma; Leukemia; Feb. 2015; pp. 1616-1618; vol. 29.

Coen A. Bernaards, et al.; Robustness of a Multivariate Normal Approximation for Imputation of Incomplete Binary Data; Statistics in Medicine; Mar. 2007; pp. 1368-1382; vol. 26(6).

Ewout W. Steyerberg, et al.; Assessing the Performance of Prediction Models: A Framework for Some Traditional and Novel Measures; Epidemiology; Jan. 2010; pp. 128-138; vol. 21(1).

Antonio Palumbo, et al.; Continuous Lenalidomide Treatment for Newly Diagnosed Multiple Myeloma; New England Journal of Medicine; May 2012; pp. 1759-1769; vol. 366(19).

Martin Oken, et al.; Toxicity and Response Criteria of the Eastern Cooperative Oncology Group; American Journal of Clinical Oncology; Dec. 1982; pp. 649-656; vol. 5(6).

European Society for Medical Oncology; Performance Scales: Karnofsky & ECOG Scores; https://oncologypro.esmo.org/oncology-in-practice/practice-tools/performance-scales; 2017.

Meral Beksac, et al.; Addition of Thalidomide to Oral Melphalan/Prednisone in Patients with Multiple Myeloma not Eligible for Transplantation: Results of a Randomized Trial from the Turkish Myeloma Study Group; European Journal of Haematology; Jan. 2011; pp. 16-22; vol. 86(1).

Wilson I. Gonsalves, et al.; Limiting Early Mortality: Do's and Don'ts in the Management of Patients with Newly Diagnosed Multiple Myeloma; American Journal of Hematology; Jan. 2016; pp. 101-108; vol. 91(1).

Antonio Palumbo, et al.; Revised International Staging System for Multiple Myeloma: A Report from International Myeloma Working Group; Journal of Clinical Oncology; Sep. 2015; pp. 2863-2869; vol. 33(26).

Antonio Palumbo, et al.; Geriatric Assessment Predicts Survival and Toxicities in Elderly Myeloma Patients: an International Myeloma Working Group Report; Blood; Mar. 2015; pp. 2068-2074; vol. 125(13).

Jayesh Mheta, et al.; How I Treat Elderly Patients with Myeloma; Blood; Sep. 2010; pp. 2215-2223; vol. 116 (13).

M A. Dimopoulos, et al.; Significant Improvement in the Survival of Patients with Multiple Myeloma Presenting with Severe Rena Impairment After the Introduction of Novel Agents; Annals of Oncology; Jan. 2014; pp. 195-200; vol. 25(1).

A. Zomas, et al.; Hypercalcemia Remains an Adverse Prognostic Factor for Newly Diagnosed Patients with Symptomatic Multiple Myeloma in the Era of Novel Anti-Myeloma Therapies, Independently of Age, ISS Stage and Treatment Type: an Analysis of 2129 Patients; Blood; 2014; Abstract 2113; vol. 124.

Shaji Kumar; Risk of Early Death in Multiple Myelmoma; Clinical Advances in Hematology & Oncology; Mar. 2012; pp. 172-174; vol. 10(3).

Morten Holmstrom, et al.; Causes of Early Death in Multiple Myeloma Patients who are Ineligible for High-Dose Therapy with Hematopoietic Stem Cell Support: A Study Based on the Nationwide Danish Myeloma Database; American Journal of Hematology; Apr. 2015; pp. E73-E74; vol. 90(4).

Ulrich Mey, et al.; Improved Survival of Older Patients with Multiple Myeloma in the Era of Novel Agents; Hematological Oncology; Dec. 2016; pp. 217-223; vol. 34(4).

W.J. Chng, et al.; IMWG Consensus on Risk Stratification in Multiple Myeloma; Leukemia; Feb. 2014; pp. 269-277; vol. 28(2).

* cited by examiner

FIG. 2F

| Attributes | Select Value from Drop-Down List ▶ |
|---|---|
| 1. Mobility | Some Problem in Walking About |
| 2. Platelet Count in X10^9/L | Confined to Bed |
| 3. ISS Stage | Some Problem in Walking About |
| 4. Age Group | No Problem in Walking About |
| 5. Hypertension History | Yes |
| 6. Diabetes History | Yes |

| Attributes | Select Value from Drop-Down List |
|---|---|
| 1. Mobility | No Problem in Walking About |
| 2. Age Group | <=75 |
| 3. Platelet Count in X10^9/L | >150 |
| 4. Serum Creatinine in mg/dL | >2 |
| 5. Diabetes History | Yes |
| 6. ISS Stage | I, II |
| 7. Novel Therapies | <=1 |

| Patient specific |
|---|
| Age (≤ 75 vs > 75) |
| Age (≤ 70 vs > 70) |
| Body mass index |
| ECOG performance status score |
| History of diabetes |
| History of hypertension |
| History of venous thromboembolism (VTE) |
| del(17p) from FISH and cytogenetic forms |
| T(4.14) from FISH and cytogenetic forms |
| T(11.14) from FISH |
| T(14.16) from FISH |
| History of MGUS |
| History of smoldering myeloma |
| Hyperdiploid |

FIG. 3B

| Disease specific |
|---|
| Lactic acid dehydrogenase ($\leq 300$ vs $> 300$ IU/L) |
| Extramedullary plasmacytoma (Yes/No) |
| History of solitary plasmacytoma (Yes/No) |
| Immunoglobulin IgG class ($< 5$ g/dL vs $\geq 5$ g/dL) |
| Albumin ($\leq 3.5$ g/dL vs $> 3.5$ g/dL |
| ISS disease stage (calculated) |
| Myeloma bone involvement |
| Hypercalcemia (serum calcium $\geq 11.5$ mg/dL) |
| Renal insufficiency (serum creatinine $> 2$ mg/dL) |
| Anemia (hemoglobin $< 10$ g/dL or $> 2$ below LLN) |
| Clonal bone marrow plasma cells ($>=10\%$ vs $<10\%$) |
| Serum monoconal protein ($>=3$ g/dL vs $<3$ g/dL) |
| Serum free light chain abnormality |
| Pathological fracture |
| Platelet count ($\leq 150 \times 10^9$/L vs $> 150 \times 10^9$/L) |
| IMWG risk (High vs Standard) |
| Beta 2 microglobulin ($\geq 5.5$ mg/L) |

FIG. 3C

| HRQOL from EQ-5D |
| --- |
| Self-care from EQ-5D |
| Mobility from EQ-5D |
| Novel therapy |
| Triplet therapy use (Yes/No) |
| IMID containing therapy use |
| PI containing therapy use |
| Novel therapy use (0,1) vs $\geq 2$ |

FIG. 3D

| Characteristic | Odds Ratio | 95% Confidence Interval | P-value |
|---|---|---|---|
| Age (<75 vs >=75) | 1.70 | (1.09, 2.67) | 0.020 |
| ECOG Performance Score (>=2 vs <2) | 3.89 | (1.67, 9.05) | 0.002 |
| History of Hypertension | 1.96 | (1.19, 3.22) | 0.008 |
| ISS Disease Stage (III vs I and II) | 1.85 | (1.18, 2.90) | 0.007 |
| Renal Insufficiency (Serum Creatinine > 2 mg/dL) | 1.59 | (0.98, 2.60) | 0.062 |
| Platelet Count (<150x10^9/L vs > 150x10^9/L) | 2.29 | (1.49, 3.53) | <0.001 |
| Mobility from EQ5D | 2.42 | (1.48, 3.94) | <0.001 |

FIG. 3E

| Characteristic | Hazard Ratio | 95% Confidence Interval | P-Value |
|---|---|---|---|
| Age (>75 vs <=75) | 1.89 | (1.58, 2.26) | <0.001 |
| EQ-5D Mobility | 1.32 | (1.10, 1.59) | 0.003 |
| Del (17p) from FISH and Cytogenic forms | 1.72 | (1.28, 2.31) | 0.001 |
| ISS disease stage | 1.31 | (1.14, 1.49) | <0.001 |
| Platelet count (<=150x10^9/L vs >150x10^9/L) | 1.64 | (1.32, 2.03) | <0.001 |
| Solitary plasmacytoma | 1.52 | (1.21, 1.91) | <0.001 |
| ECOG performance status score (2, 3, 4, 5) vs (0, 1) | 1.41 | (1.05, 1.88) | 0.022 |
| History of diabetes | 1.40 | (1.15, 1.71) | 0.001 |
| Renal insufficiency (serum creatinine > 2 mg/dL) | 1.33 | (1.08, 1.64) | 0.008 |
| Triplet therapy use | 0.77 | (0.65, 0.91) | 0.002 |

FIG. 3F-1

| Characteristic | Hazard Ratio | 95% Confidence Interval | P-value |
|---|---|---|---|
| Age (>75 vs >=75) | 2.01 | (1.66, 2.44) | <0.001 |
| ECOG Performance Score (>=2 vs <2) | 1.73 | (1.09, 2.74) | 0.019 |
| History of Diabetes | 1.37 | (1.11, 1.69) | 0.003 |
| Del(17P) from FISH and Cytogenetic forms | 1.55 | (1.18, 2.04) | 0.002 |
| Hyperdiploidy | 1.65 | (1.22, 2.25) | 0.002 |
| Extramedullary Plasmacytoma | 1.47 | (1.13, 1.91) | 0.004 |
| ISS Disease Stage (III vs II vs I) | 1.31 | (1.15, 1.50) | <0.001 |
| Renal Insufficiency (Serum Creatinine > 2 mg/dL) | 1.46 | (1.16, 1.83) | 0.001 |
| Platelet Count (<150x10^9/L vs > 150x10^9/L) | 1.47 | (1.21, 1.79) | <0.001 |
| Mobility from EQ5D | 1.49 | (1.24, 1.79) | <0.001 |
| Novel Therapy Use >= 2 vs (0,1) | 0.78 | (0.62, 0.98) | 0.033 |

| Mobility | ECOG>=2 Age>75 | ECOG>=2 Age<=75 | PC | ECOG>=2 Age>75 | ECOG>=2 Age<=75 | ISS | ECOG<2 Age>75 | ECOG<2 Age<=75 | Creat | ECOG<2 Age>75 | ECOG<2 Age<=75 |
|---|---|---|---|---|---|---|---|---|---|---|---|
| Mobility: No problem in walking about — *Hypertension = Yes* | | | | | | | | | | | |
| | 12% | 8% | PC>150 | 7% | 4% | ISS I, II | 3% | 2% | Creat<=2 | 2% | 1% |
| | 18% | 11% | | 10% | 6% | ISS III | 5% | 3% | Creat>2 | 3% | 2% |
| | 20% | 13% | | 12% | 7% | ISS I, II | 6% | 4% | Creat<=2 | 3% | 2% |
| | 29% | 19% | PC<=150 | 17% | 11% | ISS III | 10% | 6% | Creat>2 | 5% | 3% |
| | 24% | 16% | | 14% | 9% | ISS I, II | 8% | 5% | Creat<=2 | 4% | 2% |
| | 34% | 23% | | 21% | 13% | ISS III | 12% | 7% | Creat>2 | 6% | 4% |
| | 37% | 26% | | 23% | 15% | ISS I, II | 13% | 8% | Creat<=2 | 7% | 4% |
| | 48% | 36% | | 32% | 22% | ISS III | 19% | 12% | Creat>2 | 11% | 7% |
| Hypertension = No | | | | | | | | | | | |
| | | | | 9% | | | | | | | 3% |
| | 25% | 16% | | 15% | 9% | ISS I, II | 8% | 5% | Creat<=2 | 4% | 3% |
| | 35% | 24% | PC>150 | 21% | 14% | ISS III | 12% | 7% | Creat>2 | 7% | 4% |
| | 38% | 27% | | 24% | 16% | ISS I, II | 14% | 9% | Creat<=2 | 8% | 5% |
| | 50% | 37% | | 34% | 23% | ISS III | 20% | 13% | Creat>2 | 11% | 7% |
| | 43% | 31% | | 28% | 19% | ISS I, II | 16% | 10% | Creat<=2 | 9% | 6% |
| | 55% | 42% | PC<=150 | 38% | 27% | ISS III | 24% | 16% | Creat>2 | 14% | 9% |
| | 59% | 46% | | 42% | 30% | ISS I, II | 27% | 18% | Creat<=2 | 16% | 10% |
| | 69% | 57% | | 54% | 40% | ISS III | 37% | 26% | Creat>2 | 23% | 15% |
| | Age>75 | Age<=75 | | Age>75 | Age<=75 | | Age>75 | Age<=75 | | Age>75 | Age<=75 |
| Mobility: some problem in walking about — *Hypertension = Yes* | | | | | | | | | | | |
| | 45% | 32% | | 29% | 19% | ISS I, II | 17% | 11% | Creat<=2 | 10% | 6% |
| | 56% | 43% | PC>150 | 40% | 28% | ISS III | 25% | 16% | Creat>2 | 14% | 9% |
| | 60% | 47% | | 43% | 31% | ISS I, II | 28% | 18% | Creat<=2 | 16% | 10% |
| | 71% | 58% | | 55% | 42% | ISS III | 38% | 27% | Creat>2 | 24% | 16% |
| Mobility: confined to bed — *Hypertension = No* | | | | | | | | | | | |
| | 65% | 52% | | 49% | 36% | ISS I, II | 32% | 22% | Creat<=2 | 20% | 12% |
| | 75% | 63% | PC<=150 | 60% | 47% | ISS III | 43% | 31% | Creat>2 | 28% | 19% |
| | 77% | 67% | | 64% | 51% | ISS I, II | 47% | 34% | Creat<=2 | 31% | 21% |
| | 85% | 76% | | 74% | 62% | ISS III | 59% | 45% | Creat>2 | 42% | 30% |

Prognostic Matrix of Estimated Probability of Survival Beyond
Three Years for Younger Patients (Age <= 75)

| | | | Mobility: Confined to Bed | | | | | | | | | | | | |
|---|---|---|---|---|---|---|---|---|---|---|---|---|---|---|---|
| | | | ISS III | | | | ISS II | | | | ISS I | | | | |
| Del17P = No | PC>150 | | 51% | 61% | 64% | 73% | 59% | 69% | 71% | 78% | 67% | 75% | 77% | 83% | ECOG <2 |
| | | | 41% | 53% | 56% | 66% | 51% | 62% | 64% | 73% | 59% | 69% | 71% | 78% | |
| | | | 40% | 52% | 55% | 65% | 50% | 61% | 63% | 72% | 59% | 68% | 70% | 78% | |
| | | | 31% | 43% | 46% | 58% | 41% | 53% | 55% | 65% | 50% | 61% | 63% | 72% | |
| | | | 38% | 50% | 53% | 64% | 48% | 59% | 62% | 71% | 57% | 67% | 69% | 77% | ECOG >=2 |
| | | | 29% | 41% | 44% | 56% | 38% | 51% | 53% | 64% | 48% | 59% | 62% | 71% | |
| | | | 28% | 40% | 43% | 55% | 38% | 50% | 53% | 63% | 47% | 59% | 61% | 70% | |
| | | | 19% | 31% | 34% | 46% | 28% | 40% | 43% | 55% | 38% | 50% | 53% | 63% | |
| | PC<=150 | | 33% | 45% | 48% | 59% | 43% | 54% | 57% | 67% | 52% | 63% | 65% | 74% | ECOG <2 |
| | | | 23% | 36% | 38% | 51% | 33% | 45% | 48% | 59% | 43% | 54% | 57% | 67% | |
| | | | 23% | 35% | 38% | 50% | 32% | 45% | 47% | 59% | 42% | 54% | 56% | 67% | |
| | | | 15% | 25% | 28% | 40% | 23% | 35% | 38% | 50% | 32% | 45% | 47% | 59% | |
| | | | 21% | 33% | 36% | 48% | 30% | 42% | 45% | 57% | 40% | 52% | 54% | 65% | ECOG >=2 |
| | | | 13% | 23% | 26% | 38% | 21% | 33% | 36% | 48% | 30% | 43% | 45% | 57% | |
| | | | 13% | 23% | 25% | 38% | 20% | 32% | 35% | 47% | 29% | 42% | 45% | 56% | |
| | | | 7% | 15% | 17% | 28% | 13% | 23% | 26% | 38% | 20% | 32% | 35% | 47% | |
| | | | Solitary Plasmacytoma | | | | | | | | | | | | |
| | | | Yes | | No | | Yes | | No | | Yes | | No | | |
| Del17P = Yes | PC>150 | | 31% | 43% | 46% | 58% | 41% | 53% | 55% | 66% | 50% | 61% | 63% | 72% | ECOG <2 |
| | | | 22% | 34% | 37% | 49% | 31% | 43% | 46% | 58% | 41% | 53% | 55% | 66% | |
| | | | 21% | 33% | 36% | 48% | 30% | 43% | 46% | 57% | 40% | 52% | 55% | 65% | |
| | | | 13% | 24% | 26% | 39% | 21% | 33% | 36% | 48% | 30% | 43% | 46% | 57% | |
| | | | 19% | 31% | 34% | 46% | 28% | 41% | 44% | 55% | 38% | 50% | 53% | 63% | ECOG >=2 |
| | | | 12% | 22% | 24% | 37% | 19% | 31% | 34% | 46% | 28% | 41% | 44% | 55% | |
| | | | 11% | 21% | 24% | 36% | 19% | 30% | 33% | 45% | 28% | 40% | 43% | 55% | |
| | | | 6% | 13% | 15% | 26% | 11% | 21% | 24% | 36% | 19% | 30% | 33% | 46% | |
| | PC<=150 | | 15% | 26% | 28% | 41% | 23% | 35% | 38% | 50% | 32% | 45% | 48% | 59% | ECOG <2 |
| | | | 8% | 17% | 19% | 31% | 15% | 26% | 28% | 41% | 23% | 35% | 38% | 50% | |
| | | | 8% | 16% | 19% | 30% | 14% | 25% | 28% | 40% | 23% | 34% | 37% | 50% | |
| | | | 4% | 10% | 11% | 21% | 8% | 16% | 19% | 30% | 14% | 25% | 28% | 40% | |
| | | | 7% | 15% | 17% | 28% | 13% | 23% | 26% | 38% | 21% | 32% | 35% | 48% | ECOG >=2 |
| | | | 3% | 8% | 10% | 19% | 7% | 15% | 17% | 28% | 13% | 23% | 26% | 38% | |
| | | | 3% | 8% | 10% | 19% | 7% | 14% | 17% | 28% | 12% | 22% | 25% | 37% | |
| | | | 1% | 4% | 5% | 11% | 3% | 8% | 10% | 19% | 7% | 14% | 17% | 28% | |
| | | | Yes | No | Yes | No | Yes | No | Yes | No | Yes | No | Yes | No | |
| | | | History of Diabetes | | | | | | | | | | | | |

Prognostic Matrix of Estimated Probability of Survival Beyond Three Years for Younger Patients (Age <= 75) (contd.)

| | Mobility: Some Problems in Walking About | | | | | | | | | | | | |
|---|---|---|---|---|---|---|---|---|---|---|---|---|---|
| | ISS III | | | | ISS II | | | | ISS I | | | | |
| ECOG <2 | 60% | 69% | 71% | 79% | 67% | 75% | 77% | 83% | 74% | 81% | 82% | 87% | Creat <=2 |
| | 51% | 62% | 64% | 73% | 60% | 69% | 71% | 79% | 67% | 76% | 77% | 83% | |
| | 50% | 61% | 64% | 73% | 59% | 69% | 71% | 78% | 67% | 75% | 77% | 83% | Creat >2 |
| | 41% | 53% | 56% | 66% | 51% | 62% | 64% | 73% | 59% | 69% | 71% | 78% | |
| ECOG >=2 | 48% | 60% | 62% | 71% | 57% | 67% | 69% | 77% | 65% | 74% | 76% | 82% | Creat <=2 |
| | 39% | 51% | 54% | 64% | 49% | 60% | 62% | 71% | 57% | 67% | 69% | 77% | |
| | 38% | 50% | 53% | 64% | 48% | 59% | 62% | 71% | 57% | 67% | 69% | 77% | Creat >2 |
| | 29% | 41% | 44% | 56% | 38% | 50% | 53% | 64% | 48% | 59% | 62% | 71% | |
| ECOG <2 | 43% | 55% | 57% | 67% | 52% | 63% | 65% | 74% | 61% | 70% | 72% | 79% | Creat <=2 |
| | 33% | 46% | 49% | 60% | 43% | 55% | 58% | 67% | 53% | 63% | 65% | 74% | |
| | 33% | 45% | 48% | 59% | 42% | 54% | 57% | 67% | 52% | 63% | 65% | 74% | Creat >2 |
| | 23% | 35% | 38% | 51% | 33% | 45% | 48% | 59% | 43% | 54% | 57% | 67% | |
| ECOG >=2 | 31% | 43% | 46% | 57% | 40% | 52% | 55% | 65% | 50% | 61% | 63% | 72% | Creat <=2 |
| | 21% | 33% | 36% | 48% | 31% | 43% | 46% | 57% | 40% | 52% | 55% | 65% | |
| | 21% | 33% | 35% | 48% | 30% | 42% | 45% | 57% | 40% | 52% | 54% | 65% | Creat >2 |
| | 13% | 23% | 26% | 38% | 21% | 33% | 36% | 48% | 30% | 42% | 45% | 57% | |
| | Solitary Plasmacytoma | | | | | | | | | | | | |
| | Yes | | No | | Yes | | No | | Yes | | No | | |
| ECOG <2 | 41% | 53% | 56% | 66% | 51% | 62% | 64% | 73% | 59% | 69% | 71% | 78% | Creat <=2 |
| | 32% | 44% | 47% | 58% | 41% | 53% | 56% | 66% | 51% | 62% | 64% | 73% | |
| | 31% | 43% | 46% | 58% | 41% | 53% | 55% | 65% | 50% | 61% | 63% | 72% | Creat >2 |
| | 22% | 34% | 37% | 49% | 31% | 43% | 46% | 58% | 41% | 53% | 55% | 66% | |
| ECOG >=2 | 29% | 41% | 44% | 56% | 38% | 51% | 53% | 64% | 48% | 59% | 62% | 71% | Creat <=2 |
| | 20% | 31% | 34% | 47% | 29% | 41% | 44% | 56% | 39% | 51% | 53% | 64% | |
| | 19% | 31% | 34% | 46% | 28% | 40% | 43% | 55% | 38% | 50% | 53% | 63% | Creat >2 |
| | 12% | 22% | 24% | 36% | 19% | 31% | 34% | 46% | 28% | 41% | 43% | 55% | |
| ECOG <2 | 24% | 36% | 39% | 51% | 33% | 45% | 48% | 59% | 43% | 55% | 57% | 67% | Creat <=2 |
| | 15% | 26% | 29% | 41% | 24% | 36% | 39% | 51% | 33% | 45% | 48% | 59% | |
| | 15% | 25% | 28% | 41% | 23% | 35% | 38% | 50% | 32% | 45% | 48% | 59% | Creat >2 |
| | 8% | 17% | 19% | 31% | 15% | 26% | 28% | 41% | 23% | 35% | 38% | 50% | |
| ECOG >=2 | 13% | 23% | 26% | 38% | 21% | 33% | 36% | 48% | 30% | 43% | 45% | 57% | Creat <=2 |
| | 7% | 15% | 18% | 29% | 13% | 24% | 26% | 39% | 21% | 33% | 36% | 48% | |
| | 7% | 15% | 17% | 28% | 13% | 23% | 26% | 38% | 21% | 32% | 35% | 47% | Creat >2 |
| | 3% | 8% | 10% | 19% | 7% | 15% | 17% | 28% | 13% | 23% | 26% | 38% | |
| | Yes | No | Yes | No | Yes | No | Yes | No | Yes | No | Yes | No | |
| | History of Diabetes | | | | | | | | | | | | |

Prognostic Matrix of Estimated Probability of Survival Beyond Three Years for Younger Patients (Age <= 75) (contd.)

| | Mobility: No Problem in Walking About | | | | | | | | | | | | | |
|---|---|---|---|---|---|---|---|---|---|---|---|---|---|---|
| | ISS III | | | | ISS II | | | | ISS I | | | | | |
| Creat <= 2 | 68% | 76% | 77% | 83% | 74% | 81% | 82% | 87% | 80% | 85% | 86% | 90% | Yes | |
| | 60% | 70% | 72% | 79% | 68% | 76% | 77% | 83% | 74% | 81% | 82% | 87% | No | |
| Creat > 2 | 60% | 69% | 71% | 78% | 67% | 75% | 77% | 83% | 74% | 81% | 82% | 87% | Yes | |
| | 51% | 62% | 64% | 73% | 60% | 69% | 71% | 79% | 67% | 75% | 77% | 83% | No | |
| Creat <= 2 | 58% | 68% | 70% | 77% | 66% | 74% | 76% | 82% | 72% | 79% | 81% | 86% | Yes | |
| | 49% | 60% | 62% | 72% | 58% | 68% | 70% | 77% | 66% | 74% | 76% | 82% | No | |
| Creat > 2 | 48% | 60% | 62% | 71% | 57% | 67% | 69% | 77% | 65% | 74% | 75% | 82% | Yes | |
| | 39% | 51% | 54% | 64% | 48% | 60% | 62% | 71% | 57% | 67% | 69% | 77% | No | Triplet |
| Creat <= 2 | 53% | 63% | 66% | 74% | 61% | 71% | 73% | 80% | 69% | 77% | 78% | 84% | Yes | Therapy |
| | 44% | 55% | 58% | 68% | 53% | 64% | 66% | 74% | 61% | 71% | 73% | 80% | No | |
| Creat > 2 | 43% | 55% | 57% | 67% | 52% | 63% | 65% | 74% | 61% | 70% | 72% | 79% | Yes | |
| | 33% | 46% | 48% | 60% | 43% | 55% | 57% | 67% | 52% | 63% | 65% | 74% | No | |
| Creat <= 2 | 41% | 53% | 55% | 66% | 50% | 61% | 64% | 72% | 59% | 69% | 71% | 78% | Yes | |
| | 31% | 44% | 46% | 58% | 41% | 53% | 55% | 66% | 50% | 61% | 64% | 72% | No | |
| Creat > 2 | 30% | 43% | 46% | 57% | 40% | 52% | 55% | 65% | 50% | 61% | 63% | 72% | Yes | |
| | 21% | 33% | 36% | 48% | 31% | 43% | 46% | 57% | 40% | 52% | 55% | 65% | No | |
| | Solitary Plasmacytoma | | | | | | | | | | | | | |
| | Yes | | No | | Yes | | No | | Yes | | No | | | |
| Creat <= 2 | 51% | 62% | 64% | 73% | 60% | 69% | 71% | 79% | 67% | 76% | 77% | 83% | Yes | |
| | 42% | 54% | 56% | 66% | 51% | 62% | 64% | 73% | 60% | 69% | 71% | 79% | No | |
| Creat > 2 | 41% | 53% | 56% | 66% | 51% | 62% | 64% | 73% | 59% | 69% | 71% | 78% | Yes | |
| | 31% | 44% | 47% | 58% | 41% | 53% | 56% | 66% | 51% | 62% | 64% | 73% | No | |
| Creat <= 2 | 39% | 51% | 54% | 64% | 49% | 60% | 62% | 71% | 57% | 67% | 69% | 77% | Yes | |
| | 29% | 42% | 45% | 56% | 39% | 51% | 54% | 64% | 49% | 60% | 62% | 71% | No | |
| Creat > 2 | 29% | 41% | 44% | 56% | 38% | 50% | 53% | 64% | 48% | 59% | 62% | 71% | Yes | |
| | 20% | 31% | 34% | 47% | 29% | 41% | 44% | 56% | 38% | 51% | 53% | 64% | No | Triplet |
| Creat <= 2 | 33% | 46% | 49% | 60% | 43% | 55% | 58% | 67% | 53% | 63% | 65% | 74% | Yes | Therapy |
| | 24% | 36% | 39% | 51% | 34% | 46% | 49% | 60% | 43% | 55% | 58% | 68% | No | |
| Creat > 2 | 23% | 35% | 38% | 51% | 33% | 45% | 48% | 59% | 43% | 54% | 57% | 67% | Yes | |
| | 15% | 26% | 29% | 41% | 23% | 36% | 39% | 51% | 33% | 45% | 48% | 59% | No | |
| Creat <= 2 | 22% | 33% | 36% | 48% | 31% | 43% | 46% | 57% | 40% | 52% | 55% | 65% | Yes | |
| | 14% | 24% | 27% | 39% | 22% | 33% | 36% | 49% | 31% | 43% | 46% | 57% | No | |
| Creat > 2 | 13% | 23% | 26% | 38% | 21% | 33% | 36% | 48% | 30% | 42% | 45% | 57% | Yes | |
| | 7% | 15% | 17% | 29% | 13% | 23% | 26% | 38% | 21% | 33% | 36% | 48% | No | |
| | Yes | No | Yes | No | Yes | No | Yes | No | Yes | No | Yes | No | | |
| | History of Diabetes | | | | | | | | | | | | | |

FIG. 3H-3

Prognostic Matrix of Estimated Probability of Survival Beyond Three Years for Elderly Patients (Age > 75)

| | | | ISS III | | | | ISS II | | | | ISS I | | | | |
|---|---|---|---|---|---|---|---|---|---|---|---|---|---|---|---|
| | | colspan="12" | Mobility: Confined to Bed | | | | | | | | | | | | |
| Del17P = No | PC>150 | 28% | 40% | 43% | 55% | 37% | 50% | 52% | 63% | 47% | 58% | 61% | 70% | | |
| | | 19% | 30% | 33% | 46% | 28% | 40% | 43% | 55% | 37% | 50% | 52% | 63% | ECOG <2 | |
| | | 18% | 30% | 33% | 45% | 27% | 39% | 42% | 54% | 37% | 49% | 52% | 62% | | |
| | | 11% | 21% | 23% | 35% | 18% | 30% | 33% | 45% | 27% | 39% | 42% | 54% | | |
| | | 16% | 28% | 30% | 43% | 25% | 37% | 40% | 52% | 35% | 47% | 50% | 61% | | |
| | | 10% | 19% | 21% | 33% | 16% | 28% | 31% | 43% | 25% | 37% | 40% | 52% | ECOG >=2 | |
| | | 9% | 18% | 21% | 32% | 16% | 27% | 30% | 42% | 24% | 37% | 40% | 52% | | |
| | | 4% | 11% | 13% | 23% | 9% | 18% | 21% | 33% | 16% | 27% | 30% | 42% | | |
| | PC<=150 | 12% | 22% | 25% | 37% | 20% | 32% | 35% | 47% | 29% | 41% | 44% | 56% | | |
| | | 7% | 14% | 17% | 28% | 12% | 22% | 25% | 37% | 20% | 32% | 35% | 47% | ECOG <2 | |
| | | 6% | 14% | 16% | 27% | 12% | 22% | 24% | 37% | 19% | 31% | 34% | 46% | | |
| | | 3% | 8% | 9% | 18% | 6% | 14% | 16% | 27% | 12% | 22% | 25% | 37% | | |
| | | 5% | 12% | 14% | 25% | 10% | 20% | 23% | 35% | 18% | 29% | 32% | 44% | | |
| | | 2% | 7% | 8% | 16% | 5% | 12% | 14% | 25% | 11% | 20% | 23% | 35% | ECOG >=2 | ■ ■ ■ |
| | | 2% | 6% | 8% | 16% | 5% | 12% | 14% | 24% | 10% | 19% | 22% | 34% | | |
| | | 1% | 3% | 4% | 9% | 2% | 6% | 8% | 16% | 5% | 12% | 14% | 25% | | |
| | | colspan="12" | Solitary Plasmacytoma | | | | | | | | | | | | |
| | | Yes | | No | | Yes | | No | | Yes | | No | | | |
| Del17P = Yes | PC>150 | 11% | 21% | 23% | 35% | 18% | 30% | 33% | 45% | 27% | 40% | 43% | 54% | | Continued at Fig. 3I-2 |
| | | 6% | 13% | 15% | 26% | 11% | 21% | 23% | 36% | 19% | 30% | 33% | 45% | ECOG <2 | |
| | | 6% | 13% | 15% | 25% | 11% | 20% | 23% | 35% | 18% | 29% | 32% | 44% | | |
| | | 2% | 7% | 8% | 17% | 6% | 13% | 15% | 25% | 11% | 20% | 23% | 35% | | |
| | | 5% | 11% | 13% | 23% | 9% | 18% | 21% | 33% | 16% | 27% | 30% | 42% | | |
| | | 2% | 6% | 7% | 15% | 5% | 11% | 13% | 23% | 9% | 18% | 21% | 33% | ECOG >=2 | |
| | | 2% | 5% | 7% | 15% | 4% | 11% | 13% | 23% | 9% | 18% | 20% | 32% | | |
| | | 0% | 2% | 3% | 8% | 2% | 5% | 7% | 15% | 4% | 11% | 13% | 23% | | |
| | PC<=150 | 3% | 8% | 9% | 18% | 6% | 14% | 16% | 27% | 12% | 22% | 25% | 37% | | |
| | | 1% | 4% | 5% | 11% | 3% | 8% | 9% | 19% | 6% | 14% | 16% | 27% | ECOG <2 | |
| | | 1% | 3% | 4% | 11% | 3% | 7% | 9% | 18% | 6% | 14% | 16% | 27% | | |
| | | 0% | 1% | 2% | 6% | 1% | 3% | 4% | 11% | 3% | 8% | 9% | 18% | | |
| | | 1% | 3% | 4% | 9% | 2% | 6% | 8% | 16% | 5% | 12% | 14% | 25% | | |
| | | 0% | 1% | 1% | 5% | 1% | 3% | 4% | 9% | 2% | 6% | 8% | 16% | ECOG >=2 | |
| | | 0% | 1% | 1% | 4% | 1% | 3% | 3% | 9% | 2% | 6% | 8% | 16% | | |
| | | 0% | 0% | 0% | 2% | 0% | 1% | 1% | 4% | 1% | 3% | 4% | 9% | | |
| | | Yes | No | Yes | No | Yes | No | Yes | No | Yes | No | Yes | No | | |
| | | colspan="12" | History of Diabetes | | | | | | | | | | | | |

FIG. 3I-1

Prognostic Matrix of Estimated Probability of Survival Beyond
Three Years for Elderly Patients (Age > 75) (contd.)

| | | | | | | | | | | | | | |
|---|---|---|---|---|---|---|---|---|---|---|---|---|---|
| | Mobility: Some Problems in Walking About | | | | | | | | | | | | |
| | ISS III | | | | ISS II | | | | ISS I | | | | |
| ECOG <2 | 38% | 50% | 53% | 63% | 47% | 59% | 61% | 71% | 57% | 67% | 69% | 77% | Creat <=2 |
| | 28% | 41% | 43% | 55% | 38% | 50% | 53% | 63% | 48% | 59% | 61% | 71% | |
| | 28% | 40% | 43% | 55% | 37% | 49% | 52% | 63% | 47% | 58% | 61% | 70% | Creat >2 |
| | 19% | 30% | 33% | 45% | 28% | 40% | 43% | 55% | 37% | 50% | 52% | 63% | |
| ECOG >=2 | 25% | 38% | 41% | 53% | 35% | 47% | 50% | 61% | 45% | 56% | 59% | 69% | Creat <=2 |
| | 17% | 28% | 31% | 43% | 26% | 38% | 41% | 53% | 35% | 47% | 50% | 61% | |
| | 16% | 27% | 30% | 43% | 25% | 37% | 40% | 52% | 34% | 47% | 50% | 61% | Creat >2 |
| | 9% | 19% | 21% | 33% | 16% | 28% | 30% | 43% | 25% | 37% | 40% | 52% | |
| ECOG <2 | 20% | 32% | 35% | 47% | 30% | 42% | 45% | 56% | 39% | 51% | 54% | 65% | Creat <=2 |
| | 13% | 23% | 26% | 38% | 20% | 32% | 35% | 48% | 30% | 42% | 45% | 57% | |
| | 12% | 22% | 25% | 37% | 20% | 32% | 35% | 47% | 29% | 41% | 44% | 56% | Creat >2 |
| | 6% | 14% | 16% | 28% | 12% | 22% | 25% | 37% | 20% | 32% | 35% | 47% | |
| ECOG >=2 | 11% | 20% | 23% | 35% | 18% | 30% | 32% | 45% | 27% | 39% | 42% | 54% | Creat <=2 |
| | 6% | 13% | 15% | 26% | 11% | 20% | 23% | 35% | 18% | 30% | 33% | 45% | |
| | 5% | 12% | 14% | 25% | 10% | 20% | 22% | 34% | 18% | 29% | 32% | 44% | Creat >2 |
| | 2% | 6% | 8% | 16% | 5% | 12% | 14% | 25% | 10% | 20% | 23% | 35% | |
| | Solitary Plasmacytoma | | | | | | | | | | | | |
| | Yes | | No | | Yes | | No | | Yes | | No | | |
| ECOG <2 | 19% | 30% | 33% | 46% | 28% | 40% | 43% | 55% | 37% | 50% | 52% | 63% | Creat <=2 |
| | 11% | 21% | 24% | 36% | 19% | 30% | 33% | 46% | 28% | 40% | 43% | 55% | |
| | 11% | 21% | 23% | 35% | 18% | 30% | 33% | 45% | 27% | 40% | 42% | 54% | Creat >2 |
| | 6% | 13% | 15% | 26% | 11% | 21% | 23% | 35% | 18% | 30% | 33% | 45% | |
| ECOG >=2 | 10% | 19% | 21% | 33% | 17% | 28% | 31% | 43% | 25% | 37% | 40% | 52% | Creat <=2 |
| | 5% | 11% | 13% | 24% | 10% | 19% | 21% | 33% | 17% | 28% | 31% | 43% | |
| | 4% | 11% | 13% | 23% | 9% | 18% | 21% | 33% | 16% | 27% | 30% | 42% | Creat >2 |
| | 2% | 6% | 7% | 15% | 5% | 11% | 13% | 23% | 9% | 18% | 21% | 33% | |
| ECOG <2 | 7% | 14% | 17% | 28% | 12% | 23% | 25% | 37% | 20% | 32% | 35% | 47% | Creat <=2 |
| | 3% | 8% | 10% | 19% | 7% | 14% | 17% | 28% | 12% | 23% | 25% | 38% | |
| | 3% | 8% | 9% | 18% | 6% | 14% | 16% | 27% | 12% | 22% | 25% | 37% | Creat >2 |
| | 1% | 4% | 5% | 11% | 3% | 8% | 9% | 18% | 6% | 14% | 16% | 27% | |
| ECOG >=2 | 2% | 7% | 8% | 17% | 5% | 12% | 15% | 25% | 11% | 20% | 23% | 35% | Creat <=2 |
| | 1% | 3% | 4% | 10% | 2% | 7% | 8% | 17% | 5% | 12% | 15% | 25% | |
| | 1% | 3% | 4% | 9% | 2% | 6% | 8% | 16% | 5% | 12% | 14% | 25% | Creat >2 |
| | 0% | 1% | 1% | 5% | 1% | 3% | 4% | 9% | 2% | 6% | 8% | 16% | |
| | Yes | No | Yes | No | Yes | No | Yes | No | Yes | No | Yes | No | |
| | History of Diabetes | | | | | | | | | | | | |

Prognostic Matrix of Estimated Probability of Survival Beyond Three Years for Elderly Patients (Age > 75) (contd.)

| | Mobility: No Problem in Walking About | | | | | | | | | | | | | |
|---|---|---|---|---|---|---|---|---|---|---|---|---|---|---|
| | ISS III | | | | ISS II | | | | ISS I | | | | | |
| Creat <=2 | 48% | 59% | 62% | 71% | 57% | 67% | 69% | 77% | 65% | 74% | 75% | 82% | Yes | |
| | 38% | 51% | 53% | 64% | 48% | 59% | 62% | 71% | 57% | 67% | 69% | 77% | No | |
| Creat >2 | 38% | 50% | 53% | 63% | 47% | 59% | 61% | 70% | 56% | 67% | 69% | 76% | Yes | |
| | 28% | 40% | 43% | 55% | 38% | 50% | 53% | 63% | 47% | 59% | 61% | 71% | No | |
| Creat <=2 | 36% | 48% | 51% | 62% | 45% | 57% | 59% | 69% | 54% | 65% | 67% | 75% | Yes | |
| | 26% | 38% | 41% | 53% | 36% | 48% | 51% | 62% | 45% | 57% | 59% | 69% | No | |
| Creat >2 | 25% | 38% | 41% | 53% | 35% | 47% | 50% | 61% | 45% | 56% | 59% | 69% | Yes | |
| | 17% | 28% | 31% | 43% | 26% | 38% | 41% | 53% | 35% | 47% | 50% | 61% | No | Triplet Therapy |
| Creat <=2 | 30% | 42% | 45% | 57% | 40% | 52% | 55% | 65% | 49% | 61% | 63% | 72% | Yes | |
| | 21% | 33% | 36% | 48% | 30% | 43% | 45% | 57% | 40% | 52% | 55% | 65% | No | |
| Creat >2 | 20% | 32% | 35% | 47% | 29% | 42% | 45% | 56% | 39% | 51% | 54% | 64% | Yes | |
| | 13% | 23% | 26% | 38% | 20% | 32% | 35% | 47% | 30% | 42% | 45% | 56% | No | |
| Creat <=2 | 19% | 30% | 33% | 45% | 27% | 40% | 43% | 54% | 37% | 49% | 52% | 63% | Yes | |
| | 11% | 21% | 24% | 36% | 19% | 30% | 33% | 45% | 28% | 40% | 43% | 55% | No | |
| Creat >2 | 11% | 20% | 23% | 35% | 18% | 29% | 32% | 45% | 27% | 39% | 42% | 54% | Yes | |
| | 6% | 13% | 15% | 25% | 11% | 20% | 23% | 35% | 18% | 30% | 32% | 45% | No | |
| | Solitary Plasmacytoma | | | | | | | | | | | | | |
| | Yes | | No | | Yes | | No | | Yes | | No | | | |
| Creat <=2 | 28% | 41% | 44% | 55% | 38% | 50% | 53% | 63% | 48% | 59% | 61% | 71% | Yes | |
| | 19% | 31% | 34% | 46% | 28% | 41% | 44% | 55% | 38% | 50% | 53% | 64% | No | |
| Creat >2 | 19% | 30% | 33% | 46% | 28% | 40% | 43% | 55% | 37% | 50% | 52% | 63% | Yes | |
| | 11% | 21% | 24% | 36% | 19% | 30% | 33% | 46% | 28% | 40% | 43% | 55% | No | |
| Creat <=2 | 17% | 28% | 31% | 43% | 26% | 38% | 41% | 53% | 35% | 48% | 50% | 61% | Yes | |
| | 10% | 19% | 22% | 34% | 17% | 28% | 31% | 44% | 26% | 38% | 41% | 53% | No | |
| Creat >2 | 10% | 19% | 21% | 33% | 16% | 28% | 30% | 43% | 25% | 37% | 40% | 52% | Yes | |
| | 5% | 11% | 13% | 24% | 10% | 19% | 21% | 33% | 17% | 28% | 31% | 43% | No | Triplet Therapy |
| Creat <=2 | 13% | 23% | 26% | 38% | 21% | 32% | 35% | 48% | 30% | 42% | 45% | 57% | Yes | |
| | 7% | 15% | 17% | 28% | 13% | 23% | 26% | 38% | 21% | 32% | 35% | 48% | No | |
| Creat >2 | 7% | 14% | 17% | 28% | 12% | 22% | 25% | 37% | 20% | 32% | 35% | 47% | Yes | |
| | 3% | 8% | 10% | 19% | 7% | 14% | 17% | 28% | 12% | 22% | 25% | 37% | No | |
| Creat <=2 | 6% | 13% | 15% | 26% | 11% | 21% | 23% | 35% | 18% | 30% | 33% | 45% | Yes | |
| | 2% | 7% | 8% | 17% | 6% | 13% | 15% | 26% | 11% | 21% | 23% | 35% | No | |
| Creat >2 | 2% | 7% | 8% | 16% | 5% | 12% | 14% | 25% | 11% | 20% | 23% | 35% | Yes | |
| | 1% | 3% | 4% | 10% | 2% | 7% | 8% | 17% | 5% | 12% | 15% | 25% | No | |
| | Yes | No | Yes | No | Yes | No | Yes | No | Yes | No | Yes | No | | |
| | History of Diabetes | | | | | | | | | | | | | |

FIG. 3I-3

Prognostic Matrix of Estimated Probability of Survival Beyond Three Years for Elderly Patients (Age > 75)

Prognostic Matrix of Estimated Probability of Survival Beyond Three Years for Elderly Patients (Age > 75) (contd.)

*Figure omitted - complex prognostic table with ECOG, Mobility, Del17P, Hyperdiploid, Extramedullary Plasmacytoma, Creatinine, and Therapy variables*

Prognostic Matrix of Estimated Probability of Survival Beyond Three Years for Elderly Patients (Age > 75) (contd.)

FIG. 3J-3

Prognostic Matrix of Estimated Probability of Survival Beyond Three Years for Younger Patients (Age <=75)

| | | | ISS III | | | | | | | | | | ISS II | | | | | | | | | | ISS I | | | | | | | |
|---|---|---|---|---|---|---|---|---|---|---|---|---|---|---|---|---|---|---|---|---|---|---|---|---|---|---|---|---|---|---|---|
| ECOG <2 | | 49% | 60% | 62% | 70% | 72% | 73% | 80% | | 58% | 67% | 69% | 76% | 78% | 79% | 84% | | 66% | 74% | 76% | 82% | 79% | 84% | 88% | 98% | Creat >2 | Novel |
| | | 40% | 51% | 54% | 64% | 65% | 67% | 75% | | 50% | 60% | 62% | 71% | 72% | 74% | 80% | | 59% | 68% | 70% | 77% | 78% | 79% | 85% | Creat <=2 | Therapy |
| | | 36% | 47% | 49% | 60% | 61% | 64% | 72% | | 46% | 56% | 59% | 68% | 69% | 71% | 78% | | 55% | 65% | 67% | 74% | 75% | 77% | 83% | Creat >2 | Novel |
| | | 27% | 38% | 41% | 52% | 54% | 56% | 65% | Hyper- | 36% | 48% | 50% | 61% | 62% | 64% | 72% | | 46% | 57% | 59% | 68% | 70% | 71% | 78% | Creat <=2 | Therapy |
| | | 35% | 47% | 49% | 60% | 61% | 63% | 72% | diploid | 45% | 56% | 58% | 67% | 69% | 71% | 78% | PC | 55% | 64% | 66% | 74% | 75% | 77% | 82% | Creat >2 | Novel |
| | | 26% | 38% | 40% | 51% | 53% | 56% | 65% | = No | 36% | 48% | 50% | 60% | 62% | 64% | 72% | > 150 | 46% | 57% | 59% | 68% | 69% | 71% | 78% | Creat <=2 | Therapy |
| | | 22% | 33% | 36% | 47% | 49% | 51% | 61% | | 31% | 43% | 46% | 56% | 58% | 60% | 69% | | 41% | 53% | 55% | 63% | 66% | 68% | 75% | Creat >2 | Novel |
| | | 14% | 24% | 27% | 38% | 40% | 43% | 54% | | 23% | 34% | 36% | 48% | 50% | 52% | 62% | PC | 32% | 44% | 46% | 57% | 59% | 61% | 70% | Creat <=2 | Therapy |
| | | 31% | 42% | 45% | 56% | 58% | 60% | 69% | | 41% | 52% | 54% | 64% | 66% | 68% | 75% | <= 150 | 51% | 61% | 63% | 71% | 73% | 74% | 80% | Creat >2 | Novel |
| | | 22% | 33% | 36% | 47% | 49% | 52% | 62% | | 32% | 43% | 46% | 57% | 58% | 60% | 69% | | 42% | 53% | 55% | 65% | 66% | 68% | 76% | Creat <=2 | Therapy |
| | | 18% | 29% | 31% | 43% | 45% | 47% | 58% | Hyper- | 27% | 39% | 41% | 52% | 54% | 56% | 66% | | 37% | 49% | 51% | 61% | 63% | 65% | 73% | Creat >2 | Novel |
| | | 11% | 20% | 23% | 34% | 36% | 38% | 50% | diploid | 19% | 30% | 32% | 44% | 46% | 48% | 59% | | 28% | 40% | 42% | 53% | 55% | 57% | 67% | Creat <=2 | Therapy |
| | | 18% | 28% | 31% | 42% | 44% | 47% | 58% | = Yes | 27% | 38% | 41% | 52% | 54% | 56% | 66% | PC | 37% | 48% | 51% | 61% | 62% | 64% | 73% | Creat >2 | Novel |
| | | 11% | 20% | 22% | 33% | 35% | 38% | 49% | | 19% | 29% | 32% | 43% | 45% | 48% | 58% | > 150 | 28% | 39% | 42% | 53% | 55% | 57% | 66% | Creat <=2 | Therapy |
| | | 8% | 16% | 18% | 29% | 31% | 33% | 45% | | 15% | 25% | 27% | 39% | 41% | 43% | 54% | | 23% | 35% | 37% | 49% | 50% | 53% | 63% | Creat >2 | Novel |
| | | 4% | 10% | 11% | 20% | 22% | 24% | 36% | | 9% | 17% | 19% | 30% | 32% | 34% | 46% | | 16% | 26% | 28% | 40% | 42% | 44% | 55% | Creat <=2 | Therapy |
| ECOG >=2 | | 29% | 41% | 43% | 54% | 56% | 58% | 67% | | 39% | 50% | 53% | 63% | 64% | 66% | 74% | PC | 49% | 59% | 62% | 70% | 71% | 73% | 80% | Creat >2 | Novel |
| | | 21% | 32% | 34% | 46% | 48% | 50% | 60% | | 30% | 42% | 44% | 55% | 57% | 59% | 68% | <= 150 | 40% | 51% | 54% | 64% | 65% | 67% | 75% | Creat <=2 | Therapy |
| | | 17% | 27% | 30% | 41% | 43% | 46% | 56% | | 26% | 37% | 40% | 51% | 53% | 55% | 65% | | 35% | 47% | 49% | 60% | 61% | 63% | 72% | Creat >2 | Novel |
| | | 10% | 19% | 21% | 32% | 34% | 37% | 48% | Hyper- | 18% | 28% | 31% | 42% | 44% | 46% | 57% | | 27% | 38% | 41% | 52% | 53% | 56% | 65% | Creat <=2 | Therapy |
| | | 17% | 27% | 29% | 41% | 43% | 45% | 56% | diploid | 25% | 37% | 39% | 51% | 52% | 55% | 64% | PC | 35% | 47% | 49% | 59% | 61% | 63% | 71% | Creat >2 | Novel |
| | | 10% | 19% | 21% | 32% | 34% | 36% | 48% | = No | 17% | 28% | 30% | 42% | 44% | 46% | 57% | > 150 | 26% | 38% | 40% | 51% | 53% | 55% | 65% | Creat <=2 | Therapy |
| | | 7% | 15% | 17% | 27% | 29% | 31% | 43% | | 14% | 23% | 26% | 37% | 39% | 41% | 53% | | 22% | 33% | 35% | 47% | 49% | 51% | 61% | Creat >2 | Novel |
| | | 4% | 9% | 10% | 19% | 21% | 23% | 34% | | 8% | 16% | 18% | 28% | 30% | 32% | 44% | | 14% | 24% | 27% | 38% | 40% | 42% | 53% | Creat <=2 | Therapy |
| | | 13% | 23% | 25% | 37% | 38% | 41% | 52% | | 21% | 32% | 35% | 46% | 48% | 51% | 61% | | 31% | 42% | 45% | 56% | 57% | 60% | 68% | Creat >2 | Novel |
| | | 8% | 15% | 17% | 28% | 29% | 32% | 43% | | 14% | 24% | 26% | 37% | 39% | 42% | 53% | | 22% | 33% | 36% | 47% | 49% | 51% | 62% | Creat <=2 | Therapy |
| | | 5% | 12% | 13% | 23% | 25% | 27% | 39% | Hyper- | 11% | 19% | 22% | 33% | 35% | 37% | 49% | | 18% | 29% | 31% | 43% | 45% | 47% | 58% | Creat >2 | Novel |
| | | 2% | 6% | 8% | 15% | 17% | 19% | 30% | diploid | 6% | 12% | 14% | 24% | 26% | 28% | 40% | | 11% | 20% | 23% | 34% | 36% | 38% | 49% | Creat <=2 | Therapy |
| | | 5% | 12% | 13% | 23% | 25% | 27% | 38% | = Yes | 11% | 19% | 21% | 32% | 34% | 37% | 48% | PC | 18% | 28% | 31% | 42% | 44% | 47% | 57% | Creat >2 | Novel |
| | | 2% | 6% | 8% | 15% | 17% | 19% | 29% | | 6% | 12% | 14% | 25% | 25% | 28% | 39% | <= 150 | 11% | 20% | 22% | 33% | 35% | 38% | 49% | Creat <=2 | Therapy |
| | | 1% | 4% | 5% | 12% | 13% | 15% | 25% | | 4% | 9% | 11% | 20% | 21% | 23% | 35% | | 8% | 16% | 18% | 29% | 31% | 33% | 45% | Creat >2 | Novel |
| | | 0% | 2% | 2% | 7% | 9% | 9% | 17% | | 2% | 5% | 6% | 12% | 14% | 16% | 26% | | 4% | 10% | 11% | 20% | 22% | 24% | 36% | Creat <=2 | Therapy |
| Mobility : No Problem in Walking About | | Del17P = Yes | | | | | | | Del17P = No | | | | | | | | Del17P = Yes | | | | | | | Del17P = No | | | | | | | |

Prognostic Matrix of Estimated Probability of Survival Beyond Three Years for Younger Patients (Age <= 75) (contd.)

FIG. 3K-3

DIGITAL HEALTH PROGNOSTIC ANALYZER FOR MULTIPLE MYELOMA MORTALITY PREDICTIONS

CROSS-REFERENCE TO RELATED APPLICATIONS

This application is the National Phase application of International Application No. PCT/US2017/059008, filed Oct. 30, 2017, which designates the United States and was published in English, which claims priority to U.S. Provisional Patent Application No. 62/414,975, filed Oct. 31, 2016, entitled "Digital Health Prognostic Analyzer for Multiple Myeloma Mortality Predictions,". International Application No. PCT/US2017/059008 and U.S. Provisional Patent Application No. 62/414,975 are incorporated herein by reference in their entirety.

FIELD

The present disclosure relates to computer-based systems and methods for predicting likelihoods of near-terra acid long-term mortality in medical patients and, more particularly, relates to technology involving computer models for predicting mortality in patients diagnosed with multiple myeloma.

BACKGROUND

Multiple myeloma is a cancer formed by malignant plasma cells. Healthy plasma cells help humans fight infections by making antibodies that recognize and attack germs. Multiple myeloma causes cancer cells to accumulate in the bone marrow, where the cancer cells crowd out healthy blood cells. Instead of producing the antibodies for attacking germs, the cancer cells produce abnormal proteins that can cause various problems (e.g., kidney problems). Present approaches for predicting mortality for multiple myeloma patients may involve the Revised International Staging System (ISS) based upon sophisticated numerical models, such as described in "Revised International Staging System for Multiple Myeloma: A Report From International Myeloma Working Group," A. Palumbo, et al., *J. Clin Oncol* 2015, 33:2863-2869, which models are complex and require the use of computer processing, e.g., in carrying out a K-adaptive partitioning algorithm among other numerical approaches. However, the present inventors have observed that the numerical computer models of the technological approaches noted above are too constrained, suffer from limits in the numbers and types of numerical variables and predictors, and ultimately provide only a crude, qualitative prediction of patient mortality and not specific numerical predictions.

SUMMARY

Inventive computer models involving numerical algorithms described herein provide technical solutions that may overcome the technological problems mentioned above by, for example, providing a model that is not limited in the numbers and types of numerical variables and predictors and ultimately provides specific numerical predictions instead of qualitative predictions. The present disclosure provides computer-implemented systems and methods for constructing a numerical model to generate a probability that a patient diagnosed with multiple myeloma will die within a predetermined period of time. The present disclosure further provides computer-implemented systems and methods for generating a probability that a patient diagnosed with multiple myeloma will die within a predetermined period of time. The methodologies provided herein provide a technical effect and improved technical performance of enhanced precision and accuracy of final results and intermediate results over prior computational methods. Further, the methodologies provided herein, by narrowing the universe of variables to those that are screened as the most important or most predictive, provide the technical effect of improved technical performance by permitting the computational models to be trained more quickly, using less computational resources, less memory and less bandwidth, than would be required for significantly more variables, and permit the same technical enhancements when executing the finally trained model. These technical effects are explained in further detail below.

In an example, a computer-implemented method for constructing a numerical model to generate a probability that a patient diagnosed with multiple myeloma will die within a predetermined period of time is described. Reference data for a plurality of patients diagnosed with multiple myeloma is received. The reference data comprises for respective patients of the plurality of patients (i) data for variables of a set of patient variables, and (ii) survival data indicative of an amount of time between the patient's cancer diagnosis and the patient's death or between the cancer diagnosis and a date in a database when the patient is last known to be alive. Multiple candidate computer models comprising different combinations of the variables of the set of patient variables are generated. Each of the candidate computer models includes multiple weighting factors associated with the variables, and each variable of each candidate computer model has an associated weighting factor. Multiple computerized numerical regression analyses for the multiple candidate computer models are conducted based on the data for the variables and the survival data to determine first selected variables and second selected variables from the set of patient variables. The first selected variables satisfy one or more selection criteria to be deemed predictive of mortality for a first predetermined period of time for patients diagnosed with multiple myeloma, and the second selected variables satisfy one or more selection criteria deemed to be predictive of mortality for a second predetermined period of time for patients diagnosed with multiple myeloma. A first computer model comprising a combination of variables of the first selected variables and first weighting factors associated with the respective first selected variables is generated. A second computer model comprising a combination of variables of the second selected variables and second weighting factors associated with the respective selected second variables is generated. The first computer model and the second computer model are trained using the reference data to determine numerical values for the respective first and second weighting factors. The first computer model and the second computer model are updated to include the determined numerical values for the first weighting factors and the second weighting factors for each selected variable of the first and second selected variables such that the first computer model is configured to generate probability data that a patient satisfying certain first selectable criteria will die within the first predetermined period of time and such that the second computer model is configured to generate probability data that a patient satisfying certain second selectable criteria will die within the second predetermined period of time. The conducting of the multiple computerized numerical regression analyses based on the data for the variables and the survival data to determine the first and second selected variables implements a more sophisticated variable selection than prior computational methods and thus provides a technical effect and improved technical performance of enhanced precision and accuracy of final results and intermediate results generated by the first and second computer models over the prior computational methods. This technical effect is achieved without further disadvantages (e.g., increase of computation time, need for additional computational resources, etc.). Further, by conducting the multiple computerized numerical regression analyses to determine the first and second selected variables and generating the first and second computer models based on first and second selected variables, respectively, the universe of variables is narrowed to those that are screened as most important or predictive, thus providing the technical effect of improved technical performance by permitting the first and second computer models to be trained more quickly, using less computational resources, less memory and less bandwidth, than would be required for significantly more variables, and permits the same technical enhancements when executing the finally trained first and second computer models.

In an example, the first selected variables include a first variable indicative of the patient's age, a second variable indicative of the patient's Eastern Cooperative Oncology Group (ECOG) performance status, a third variable indicative of the patient's history of hypertension, a fourth variable indicative of a stage of the patient's multiple myeloma disease, a fifth variable indicative of whether the patient has renal insufficiency, a sixth variable indicative of the patient's platelet count, and a seventh variable indicative of the patient's mobility. In an example, the second selected variables include a first variable indicative of the patient's age, a second variable indicative of the patient's mobility, a third variable indicative of the patient's Del(17P) from FISH and cytogenetic forms, a fourth variable indicative of a stage of the patient's multiple myeloma disease, a fifth variable indicative of the patient's platelets, a sixth variable indicative of whether the patient has a history of solitary plasmacytoma, a seventh variable indicative of the patient's ECOG performance status, an eighth variable indicative of the patient's history of diabetes, a ninth variable indicative of whether the patient has renal insufficiency, and a tenth variable indicative of whether the patient has used triplet therapy. The use of the first and second computer models including these variables implements a more sophisticated set of variables than prior computational methods and thus provides a technical effect and improved technical performance of enhanced precision and accuracy of final results and intermediate results generated by the first and second computer models over the prior computational methods. This technical effect is achieved without further disadvantages (e.g., increase of computation time, need for additional computational resources, etc.). Further, by conducting the multiple computerized numerical regression analyses to narrow the universe of variables to these particular variables, this provides the technical effect of improved technical performance by permitting the first and second computer models to be trained more quickly, using less computational resources, less memory and less bandwidth, than would be required for significantly more variables, and permits the same technical enhancements when executing the finally trained first and second computer models.

In an example, the computer-implemented method includes validating the first and second computer models with testing using additional independent data not used in training the first and second computer models. Further, in an example, the computer-implemented method includes providing a graphical user interface with selectable input fields adapted to receive input information from a user, the processing system processing the input information and numerical data of at least one of the first computer model and the second computer model so as to render to the user a probability that the patient will die within at least one of the first predetermined time and the second predetermined time. By conducting the multiple computerized numerical regression analyses to determine the first and second selected variables and generating the first and second computer models based on the first and second selected variables, respectively, this narrows the universe of variables and thus provides the technical effect of improved technical performance by requiring less input information from the user, such that a smaller amount of input data is processed to render the probability. Processing the smaller amount of input data enables the probability to be rendered more quickly, using less computational resources, less memory and less bandwidth, than would be required for a larger amount of input data.

In an example, the determining of the first selected variables and the second selected variables in the computer-implemented method includes analyzing each variable of the set of patient variables independently of the other variables to determine variables that have a degree of unvariable association with patient death within the first predetermined period of time that is above a threshold, and analyzing each variable of the set of patient variables independently of the other variables to determine variables that have a degree of univariate association with patient death within the second predetermined period of time that is above the threshold. The independent analyses of each variable of the set of patient variables to determine the first and second selected variables that have a degree of univariate association with patient death that is above a threshold implements a more sophisticated variable selection than prior computational methods and thus provides a technical effect and improved technical performance of enhanced precision and accuracy of final results and intermediate results generated by the first and second computer models over the prior computational methods.

In an example, the training of the first computer model and the second computer model includes processing the reference data to determine, for patients represented in the reference data, numerical measures for respective variables of the first selected variables, and conducting a first computerized numerical regression analysis based on the determined numerical measures to determine the first weighting factors. The training of the first computer model and the second computer model further includes processing the reference data to determine, for patients represented in the reference data, numerical measures for respective variables of the second selected variables, and conducting a second computerized numerical regression analysis based on the determined numerical measures to determine the second weighting factors. In an example, the computer-implemented method further includes determining variables of the first and second selected variables for which an amount of data missing from the reference data is above a predetermined amount, and prior to the training of the first and second computer models, performing an imputation procedure to impute data for the variables having the amount of data missing above the predetermined amount.

An exemplary system for constructing a numerical model to generate a probability that a patient diagnosed with multiple myeloma will die within a predetermined period of time includes a processing system and computer-readable memory in communication with the processing system encoded with instructions for commanding the processing system to execute steps. In executing the steps, reference data for a plurality of patients diagnosed with multiple myeloma is received. The reference data comprises for respective patients of the plurality of patients (i) data for variables of a set of patient variables, and (ii) survival data indicative of an amount of time between the patient's cancer diagnosis and the patient's death or between the cancer diagnosis and a date at which the patient is last known to be alive. Multiple candidate computer models comprising different combinations of the variables of the set of patient variables are generated. Each of the candidate computer models includes multiple weighting factors associated with the variables, and each variable of each candidate computer model has an associated weighting factor. Multiple computerized numerical regression analyses for the multiple candidate computer models are conducted based on the data for the variables and the survival data to determine first selected variables and second selected variables from the set of patient variables. The first selected variables satisfy one or more selection criteria to be deemed predictive of mortality for a first predetermined period of time for patients diagnosed with multiple myeloma, and the second selected variables satisfy one or more selection criteria deemed to be predictive of mortality for a second predetermined period of time for patients diagnosed with multiple myeloma. A first computer model comprising a combination of variables of the first selected variables and first weighting factors associated with the respective first selected variables is generated. A second computer model comprising a combination of variables of the second selected variables and second weighting factors associated with the respective selected second variables is generated. The first computer model and the second computer model are trained using the reference data to determine numerical values for the respective first and second weighting factors. The first computer model and the second computer model are updated to include the determined numerical values for the first weighting factors and the second weighting factors for each selected variable of the first and second selected variables such that the first computer model is configured to generate probability data that a patient satisfying certain first selectable criteria will die within the first predetermined period of time and such that the second computer model is configured to generate probability data that a patient satisfying certain second selectable criteria will die within the second predetermined period of time. The conducting of the multiple computerized numerical regression analyses based on the data for the variables and the survival data to determine the first and second selected variables implements a more sophisticated variable selection than prior systems and thus provides a technical effect and improved technical performance of enhanced precision and accuracy of final results and intermediate results generated by h first and second computer models over the prior systems. This technical effect is achieved without further disadvantages (e.g., increase of computation time, need for additional computational resources, etc.). Further, by conducting the multiple computerized numerical regression analyses to determine the first and second selected variables and generating the first and second computer models based on the first and second selected variables, respectively, the universe of variables is narrowed to those that are screened as most important or predictive, thus providing the technical effect of improved technical performance by permitting the first and second computer models to be trained more quickly, using less computational resources, less memory and less bandwidth, than would be required for significantly more variables, and permits the same technical enhancements when executing the finally trained first and second computer models.

In an example system, the first selected variables include a first variable indicative of the patient's ape, a second variable indicative of the patient's Eastern Cooperative Oncology Group (ECOG) performance status, a third variable indicative of the patient's history of hypertension, a fourth variable indicative of a stage of the patient's multiple myeloma disease, a fifth variable indicative of whether the patient has renal insufficiency, a sixth variable indicative of the patient's platelet count, and a seventh variable indicative of the patient's mobility. In an example, the second selected variables include a first variable indicative of the patient's age, a second variable indicative of the patient's mobility, a third variable indicative of the patient's Del(17P) from and cytogenetic forms, a fourth variable indicative of a stage of the patient's multiple myeloma disease, a fifth variable indicative of the patient's platelet count, a sixth variable indicative of whether the patient has a history of solitary plasmacytoma, a seventh variable indicative of the patient's ECOG performance status, an eighth variable indicative of the patient's history of diabetes, a ninth variable indicative of whether the patient has renal insufficiency, and a tenth variable indicative of whether the patient has used triplet therapy. The use of the first and second computer models including these variables implements a more sophisticated set of variables than prior computational methods and thus provides a technical effect and improved technical performance of enhanced precision and accuracy of final results and intermediate results generated by the numerical model over the prior systems. Further, by conducting the multiple computerized numerical regression analyses to narrow the universe of variables to these particular variables, this provides the technical effect of improved technical performance by permitting the first and second computer models to be trained more quickly, using less computational resources, less memory and less bandwidth, than would be required for significantly more variables, and permits the same technical enhancements when executing the finally trained first and second computer models.

In an example, the computer-readable memory of the system is encoded with instructions for commanding the processing system to execute the steps including validating the first and second computer models with testing using additional independent data not used in training the first and second computer models. In an example, the steps further include providing a graphical user interface with selectable input fields adapted to receive input information from a user, and processing the input information and numerical data of at least one of the first computer model and the second computer model so as to render to the user a probability that the patient will die within at least one of the first predetermined time and the second predetermined time. In an example of the system, the determining of the first selected variables and the second selected variables includes analyzing each variable of the set of patient variables independently of the other variables to determine variables that have a degree of univariate association with patient death within the first predetermined period of time that is above a threshold, and analyzing each variable of the set of patient variables independently of the other variables to determine variables that have a degree of univariate association with patient death within the second predetermined period of time that is above the threshold. In an example of the system, the training of the first computer model and the second computer model includes processing the reference data to determine, for patients represented in the reference data, numerical measures for respective variables of the first selected variables, and conducting a first computerized numerical regression analysis based on the determined numerical measures to determine the first weighting factors, and processing the reference data to determine, for patients represented in the reference data, numerical measures for respective variables of the second selected variables, and conducting a second computerized numerical regression analysis based on the determined numerical measures to determine the second weighting factors. En an example, the computer-readable memory of the system is encoded with instructions for commanding the processing system to execute the steps including determining variables of the first and second selected variables for which an amount of data missing from the reference data is above a predetermined amount, and prior to the training of the first and second computer models, performing an imputation procedure to impute data for the variables having the amount of data missing above the predetermined amount. The above-described operations provide technical effects and improved technical performance for the reasons explained above.

An exemplary non-transitory computer-readable storage medium for constructing a numerical model to generate a probability that a patient diagnosed with multiple myeloma will die within a predetermined period of time comprises computer executable instructions which, when executed, cause a processing system to execute steps. In executing the steps, reference data for a plurality of patients diagnosed with multiple myeloma is received. The reference data comprises for respective patients of the plurality of patients (i) data for variables of a set of patient variables, and (ii) survival data indicative of an amount of time between the patient's cancer diagnosis and the patient's death or between the cancer diagnosis and a date at which the patient is last known to be alive. Multiple candidate computer models comprising different combinations of the variables of the set of patient variables are generated. Each of the candidate computer models includes multiple weighting factors associated with the variables, and each variable of each candidate computer model has an associated weighting factor. Multiple computerized numerical regression analyses for the multiple candidate computer models are conducted based on the data for the variables and the survival data to determine first selected variables and second selected variables from the set of patient variables. The first selected variables satisfy one or more selection criteria to be deemed predictive of mortality for a first predetermined period of time for patients diagnosed with multiple myeloma, and the second selected variables satisfy one or more selection criteria deemed to be predictive of mortality for a second predetermined period of time for patients diagnosed with multiple myeloma. A first computer model comprising a combination of variables of the first selected variables and first weighting factors associated with the respective first selected variables is generated. A second computer model comprising a combination of variables of the second selected variables and second weighting factors associated with the respective selected second variables is generated. The first computer model and the second computer model are trained using the reference data to determine numerical values for the respective first and second weighting factors. The first computer model and the second computer model are updated to include the determined numerical values for the first weighting factors and the second weighting factors for each selected variable of the first and second selected variables such that the first computer model is configured to generate probability data that a patient satisfying certain first selectable criteria will die within the first predetermined period of time and such that the second computer model is configured to generate probability data that a patient satisfying certain second selectable criteria will die within the second predetermined period of time. The conducting of the multiple computerized numerical regression analyses based on the data for the variables and the survival data to determine the first and second selected variables implements a more sophisticated variable selection than prior non-transitory computer-readable storage mediums and thus provides a technical effect and improved technical performance of enhanced precision and accuracy of final results and intermediate results generated by the first and second computer models over the prior storage mediums. This technical effect is achieved without further disadvantages (e.g., increase of computation time, need for additional computational resources, etc.). Further, by conducting the multiple computerized numerical regression analyses to determine the first and second selected variables and generating the first and second computer models based on the first and second selected variables, respectively, the universe of variables is narrowed to those that are screened as most important or predictive, thus providing the technical effect of improved technical performance by permitting the first and second computer models to be trained more quickly, using less computational resources, less memory and less bandwidth, than would be required for significantly more variables, and permits the same technical enhancements when executing the finally trained first and second computer models.

In an example non-transitory computer-readable storage medium, the first selected variables include a first variable indicative of the patient's age, a second variable indicative of the patient's Eastern Cooperative Oncology Group (ECOG) performance status, a third variable indicative of the patient's history of hypertension, a fourth variable indicative of a stage of the patient's multiple myeloma disease, a fifth variable indicative of whether the patient has renal insufficiency, a sixth variable indicative of the patient's platelet count, and a seventh variable indicative of the patient's mobility. In an example, the second selected variables include a first variable indicative of the patient's age, a second variable indicative of the patient's mobility, a third variable indicative of the patient's Del(17P) from FISH and cytogenetic forms, a fourth variable indicative of a stage of the patient's multiple myeloma disease, a fifth variable indicative of the patient's platelet count, a sixth variable indicative of whether the patient has a history of solitary plasmacytoma, a seventh variable indicative of the patient's ECOG performance status, an eighth variable indicative of the patient's history of diabetes, a ninth variable indicative of whether the patient has renal insufficiency, and a tenth variable indicative of whether the patient has used triplet therapy. The use of the first and second computer models including these variables implements a more sophisticated set of variables than prior computational methods and thus provides a technical effect and improved technical performance of enhanced precision and accuracy of final results and intermediate results generated by the numerical model over the prior systems. Further, by conducting the multiple computerized numerical regression analyses to narrow the universe of variables to these particular variables, this provides the technical effect of improved technical performance by permitting the first and second computer models to be trained more quickly, using less computational resources, less memory and less bandwidth, than would be required for significantly more variables, and permits the same technical enhancements when executing the finally trained first and second computer models.

In an example, the non-transitory computer-readable storage medium comprises computer executable instructions which, when executed, cause the processing system to execute the steps including validating the first and second computer models with testing using additional independent data not used in training the first and second computer models. In an example non-transitory computer-readable storage medium, the steps include providing a graphical user interface with selectable input fields adapted to receive input information from a user and processing the input information and numerical data of at least one of the first computer model and the second computer model so as to render to the user a probability that the patient will die within at least one of the first predetermined time and the second predetermined time. In an example non-transitory computer-readable storage medium, the determining of the first selected variables and the second selected variables includes analyzing each variable of the set of patient variables independently of the other variables to determine variables that have a degree of univariate association with patient death within the first predetermined period of time that is above a threshold, and analyzing each variable of the set of patient variables independently of the other variables to determine variables that have a degree of univariate association with patient death within the second predetermined period of time that is above the threshold. In an example non-transitory computer-readable storage medium, the training of the first computer model and the second computer model includes processing the reference data to determine, for patients represented in the reference data, numerical measures for respective variables of the first selected variables, and conducting a first computerized numerical regression analysis based on the determined numerical measures to determine the first weighting factors, and processing the reference data to determine, for patients represented in the reference data, numerical measures for respective variables of the second selected variables, and conducting a second computerized numerical regression analysis based on the determined numerical measures to determine the second weighting factors. In an example, the non-transitory computer-readable storage medium comprises computer executable instructions which, when executed, cause the processing system to execute the steps including determining variables of the first and second selected variables for which an amount of data missing from the reference data is above a predetermined amount, and prior to the training of the first and second computer models, performing an imputation procedure to impute data for the variables having the amount of data missing above the predetermined amount. These operations provide technical effects and improved technical performance for the reasons explained above.

As noted above, the present disclosure also provides computer-implemented systems and methods for generating a probability that a patient diagnosed with multiple myeloma will die within a predetermined period of time. In an example computer-implemented method for generating a probability that a patient diagnosed with multiple myeloma will die within a predetermined period of time, input data for a patient diagnosed with multiple myeloma is received. The input data comprises data for multiple variables of a set of patient variables. The input data is processed to determine a first numerical measure indicative of an age of the patient.

The input data is processed to determine a second numerical measure indicative of a stage of the patient's multiple myeloma disease. The input data is processed to determine a third numerical measure indicative of the patient's mobility. A numerical model associated with a predetermined period of time is applied to the first numerical measure, the second numerical measure, and the third numerical measure to determine a probability that the patient will die within the predetermined period of time. The numerical model includes a first variable and an associated first weighting factor, the first variable receiving a value of the first numerical measure. The numerical model also includes a second variable and an associated second weighting factor, the first variable receiving a value of the second numerical measure. The numerical model further includes a third variable and an associated third weighting factor, the third variable receiving a value of the third numerical measure. The application of the numerical model including the first, second, and third variables, configured to receive the first, second, and third numerical measures, respectively, implements a more sophisticated set of variables than prior computational methods and thus provides a technical effect and improved technical performance of enhanced precision and accuracy of final results and intermediate results generated by the numerical model over the prior computational methods.

In examples, the numerical model may include additional variables that receive values of additional numerical measures determined from the input data including numerical measures indicative of the patient's history of hypertension, performance status, renal sufficiency, platelet count, history of diabetes, Del(17P) from FISH and cytogenetic forms, hyperdiploidy, extramedullary plasmacytoma, novel therapy use, triplet therapy use, and solitary plasmacytoma. The application of the numerical model including these additional variables implements a more sophisticated set of variables than prior computational methods and thus provides a technical effect and improved technical performance of enhanced precision and accuracy of final results and intermediate results generated by the numerical model over the prior computational methods.

In an example, the computer-implemented method includes processing the input data with the processing system to determine a fourth numerical measure indicative of the patient's platelet count, and processing the input data with the processing system to determine a fifth numerical measure indicative of whether the patient has renal insufficiency or a history of diabetes or hypertension. The numerical model is applied to the fourth numerical measure and the fifth numerical measure to determine the probability, where the numerical model includes a fourth variable and an associated fourth weighting factor, the fourth variable receiving a value of the fourth numerical measure and a fifth variable and an associated fifth weighting factor, the fifth variable receiving a value of the fifth numerical measure. The application of the numerical model including the fourth and fifth variables and associated weighting factors implements a more sophisticated set of variables than prior computational methods and thus provides a technical effect and improved technical performance of enhanced precision and accuracy of final results and intermediate results generated by the numerical model over the prior computational methods.

In an example, the computer-implemented method includes processing the input data with the processing system to determine a fourth numerical measure indicative of a performance status of the patient, and applying the numerical model to the fourth numerical measure to determine the probability, the numerical model including a fourth variable and an associated fourth weighting factor, the fourth variable receiving a value of the fourth numerical measure. The application of the numerical model including the fourth variable and associated weighting factor implements a more sophisticated set of variables than prior computational methods and thus provides a technical effect and improved technical performance of enhanced precision and accuracy of final results and intermediate results generated by the numerical model over the prior computational methods.

An exemplary system for generating a probability that a patient diagnosed with multiple myeloma will die within a predetermined period of time includes a processing system and computer-readable memory in communication with the processing system encoded with instructions for commanding the processing system to execute steps. In executing the steps, input data for a patient diagnosed with multiple myeloma is received. The input data comprises data for multiple variables of a set of patient variables. The input data is processed to determine a first numerical measure indicative of an age of the patient. The input data is processed to determine a second numerical measure indicative of a stage of the patient's multiple myeloma disease. The input data is processed to determine a third numerical measure indicative of the patient's mobility. A numerical model associated with a predetermined period of time is applied to the first numerical measure, the second numerical measure, and the third numerical measure to determine a probability that the patient will die within the predetermined period of time. The numerical model includes a first variable and an associated first weighting factor, the first variable receiving a value of the first numerical measure. The numerical model also includes a second variable and an associated second weighting factor, the first variable receiving a value of the second numerical measure. The numerical model further includes a third variable and an associated third weighting factor, the third variable receiving a value of the third numerical measure. The application of the numerical model including the first, second, and third variables, configured to receive the first, second, and third numerical measures, respectively, implements a more sophisticated set of variables than prior systems and thus provides a technical effect and improved technical performance of enhanced precision and accuracy of final results and intermediate results generated by the numerical model over the prior systems.

In examples, the numerical model may include additional variables that receive values of additional numerical measures determined from the input data including numerical measures indicative of the patient's history of hypertension, performance status, renal sufficiency, platelet count, history of diabetes, Del(17P) from FISH and cytogenetic forms, hyperdiploidy, extramedullary plasmacytoma, novel therapy use, triplet therapy use, and solitary plasmacytoma. In an example of the system, the computer-readable memory is encoded with the instructions for commanding the processing system to execute the steps including processing the input data to determine a fourth numerical measure indicative of the patient's platelet count, processing the input data to determine a fifth numerical measure indicative of whether the patient has renal insufficiency or a history of diabetes or hypertension, and applying the numerical model to the fourth numerical measure and the fifth numerical measure to determine the probability. The numerical model includes a fourth variable and an associated fourth weighting factor, the fourth variable receiving a value of the fourth numerical measure, and a fifth variable and an associated fifth weighting factor, the fifth variable receiving a value of the fifth numerical measure. In another example of the system, the computer-readable memory is encoded with the instructions for commanding the processing system to execute the steps including processing the input data to determine a fourth numerical measure indicative of a performance status of the patient applying the numerical model to the fourth numerical measure to determine the probability, the numerical model including a fourth variable and an associated fourth weighting factor, the fourth variable receiving a value of the fourth numerical measure. These operations provide technical effects and improved technical performance for the reasons explained above.

An exemplary non-transitory computer-readable storage medium for generating a probability that a patient diagnosed with multiple myeloma will die within a predetermined period of time comprises computer executable instructions which, when executed, cause a processing system to execute steps. In executing the steps, input data for a patient diagnosed with multiple myeloma is received. The input data comprises data for multiple variables of a set of patient variables. The input data is processed to determine a first numerical measure indicative of an age of the patient. The input data is processed to determine a second numerical measure indicative of a stage of the patient's multiple myeloma disease. The input data is processed to determine a third numerical measure indicative of the patient's mobility. A numerical model associated with a predetermined period of time is applied to the first numerical measure, the second numerical measure, and the third numerical measure to determine a probability that the patient will die within the predetermined period of tune. The numerical model includes a first variable and an associated first weighting factor, the first variable receiving a value of the first numerical measure. The numerical model also includes a second variable and an associated second weighting factor, the first variable receiving a value of the second numerical measure. The numerical model further includes a third variable and an associated third weighting factor, the third variable receiving a value of the third numerical measure. The application of the numerical model including the first, second, and third variables, configured to receive the first, second, and third numerical measures, respectively, implements a more sophisticated set of variables than prior systems and thus provides a technical effect and improved technical performance of enhanced precision and accuracy of final results and intermediate results generated by the numerical model over the prior systems.

In examples, the numerical model may include additional variables that receive values of additional numerical measures determined from the input data including numerical measures indicative of the patient's history of hypertension, performance status, renal sufficiency, platelet count, history of diabetes, Del(17P) from FISH and cytogenetic forms, hyperdiploidy, extramedullary plasmacytoma, novel therapy use, triplet therapy use, and solitary plasmacytoma. In an example, the non-transitory computer-readable storage medium comprises the computer executable instructions which, when executed, cause the processing system to the execute steps including processing the input data to determine a fourth numerical measure indicative of the patient's platelet count, processing the input data to determine a fifth numerical measure indicative of whether the patient has renal insufficiency or a history of diabetes or hypertension, and applying the numerical model to the fourth numerical measure and the fifth numerical measure to determine the probability. The numerical model includes a fourth variable and an associated fourth weighting factor, the fourth variable receiving a value of the fourth numerical measure, and a fifth variable and an associated fifth weighting factor, the fifth variable receiving a value of the fifth numerical measure. In another example, the non-transitory computer-readable storage medium comprises the computer executable instructions which, when executed, cause the processing system to the execute steps including processing the input data to determine a fourth numerical measure indicative of a performance status of the patient, and applying the numerical model to the fourth numerical measure to determine the probability, the numerical model including a fourth variable and an associated fourth weighting factor, the fourth variable receiving a value of the fourth numerical measure. These operations provide technical effects and improved technical performance for the reasons explained above.

The subject matter described herein provides many technical advantages. As described below, the computer-based techniques of the present disclosure provide processes for constructing a numerical model for predicting death in patients diagnosed with multiple myeloma in an automated manner that requires no human intervention or minimal human intervention. In embodiments described below, the constructing of the numerical model includes (i) processing large amounts of reference data via multiple regression analyses to automatically determine predictors of death in patients diagnosed with multiple myeloma, (ii) performing an imputation process to automatically generate data for variables of the reference data determined to have missing data, and (iii) automatically building and training the numerical model, which includes the predictors of death and associated weighting factors that take into account the relative contributions of each of the predictors. After being generated, the numerical model is applied to new data for a patient diagnosed with multiple myeloma to generate a probability that the patient will die within a predetermined period of time. The processes described herein thus enable an accurate, multivariate analysis of a patient's prognosis to be performed in a relatively fast, automated manner that requires no human intervention or only minimal human intervention and provide technological refinements over existing technological approaches by virtue of more sophisticated variable selection and implementation, such that the approaches described herein may provide improved mortality predictions. These technical advantages and others are described in detail below.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIGS. 2A-2H illustrate screenshots of exemplary software utilizing the systems and methods described herein, according to embodiments of the present disclosure.

FIGS. 3B-3D depict exemplary patient variables included in reference data for training the numerical computer model, according to embodiments of the present disclosure.

FIG. 3E is a table including a summary of inferences from a logistic model developed using multiple imputation.

FIG. 3F-1 is a table including an exemplary summary of inferences from a Cox model developed using multiple imputation.

FIG. 3F-2 is a table including another exemplary summary of inferences from a Cox model developed using multiple imputation.

FIGS. 3G, 3H-1, 3H-2, 3H-3, 3I-1, 3I-2, 3I-3, 3J-1, 3J-2, 3J-3, 3K-1, 3K-2, and 3K-3 depict exemplary prediction matrices generated according to embodiments of the present disclosure.

DETAILED DESCRIPTION

Figure 1:
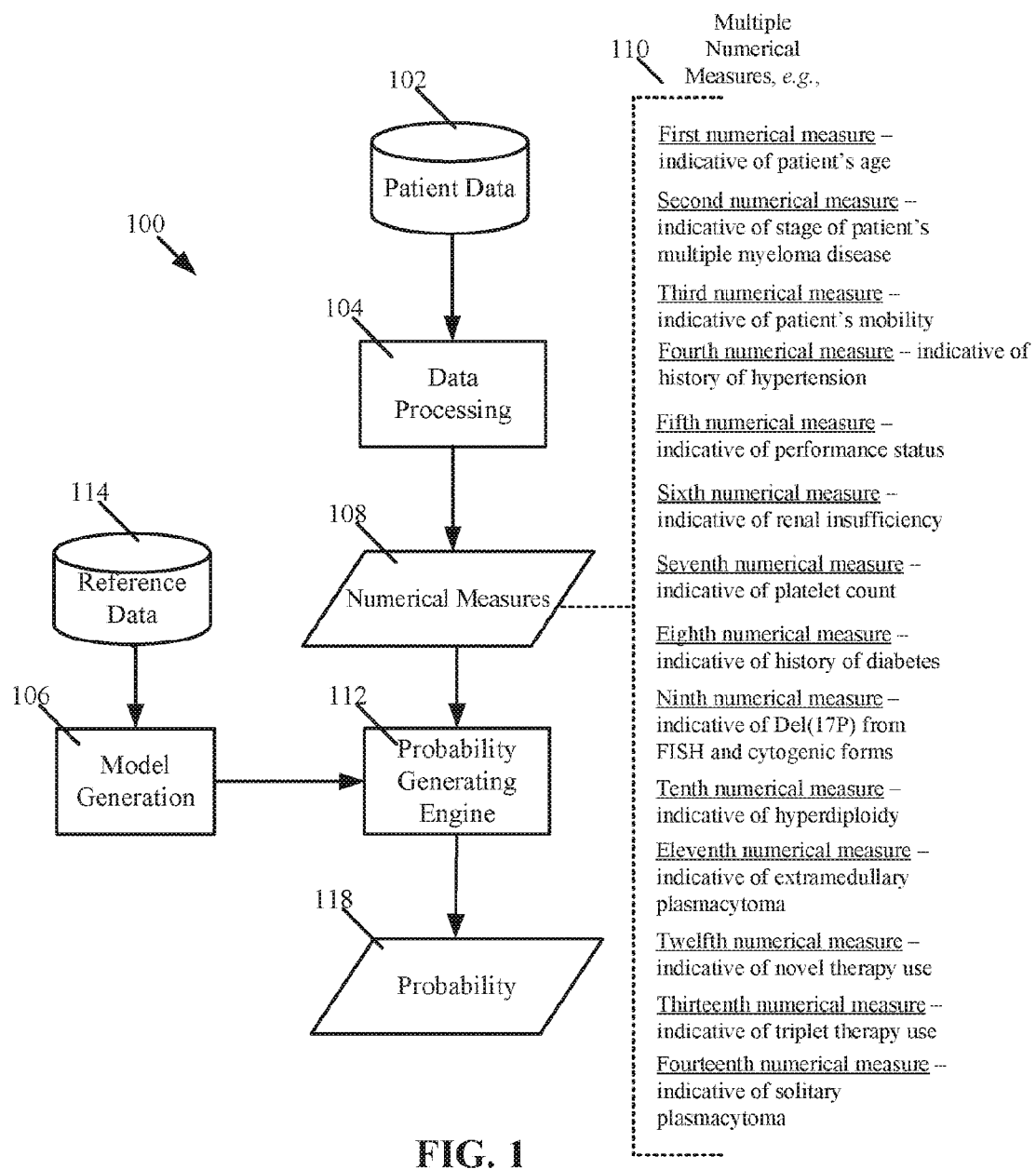
FIG. 1 is a block diagram illustrating an exemplary system for generating a probability that a patient diagnosed with multiple myeloma will die within a predetermined period of time according to an embodiment of the present disclosure.

FIG. 1 is a block diagram 100 illustrating an exemplary system for generating a probability that a patient diagnosed with multiple myeloma will die within a predetermined period of time. To generate this probability, the exemplary system of FIG. 1 comprises a computer-based system for automatically processing patient data 102 for the patient, where the patient data 102 comprises data for multiple variables of a set of variables. For instance, the patient data 102 may include data for one or more of the following variables for the patient: age, performance status (e.g., Eastern Cooperative Oncology Group (ECOG) performance status), whether the patient has a history of diabetes, whether the patient has a history of hypertension, a stage of the patient's multiple myeloma disease (e.g., International Staging System (ISS) stage of the disease), platelet count, serum creatinine level, a measure of the patient's mobility, etc. The patient data 102 may be provided by a user (e.g., the patient, the patient's doctor, a nurse, other medical practitioner, etc.) via a graphical user interface (GUI) of a software application. Exemplary GUIs for receiving data from the user e described below with reference to FIGS. 2A-2F.

The patient data 102 may be received at a data processing module 104 of the computer-based system. Processing performed on the patient data 102 at the data processing module 104 is used to generate one or more numerical measures 108. The processing module 104 may be implemented with a computer processing system comprising one or more central processing units (CPUs) in one computer or distributed among multiple computers in communication with suitable computer memory and programmed to carry out the processing as described herein. The one or more numerical measures 108 may include numerical measures or Boolean values that are representative of aspects of the patient data 102. In embodiments, a numerical measure comprises a value from the patient data 102 (e.g., a value indicative of the patient's age) or a value derived from the patient data 102 (e.g., a value indicative of whether the patient's age is greater than 75 years). Specifically, in embodiments, the one or more numerical measures 108 may include numerical measures that are related to the patient's multiple myeloma disease (e.g., a numerical measure related to a stage of the patient's multiple myeloma disease, etc.) and also numerical measures that are not related to the multiple myeloma disease (e.g., numerical measures relating to the patient's age, health history, etc.). The data processing module 104 generates exemplary numerical measures 110 from the patient data 102. The exemplary numerical measures 110 may include the first, second, and third numerical measures illustrated in FIG. 1, among others.

As shown in FIG. 1, the first exemplary numerical measure is indicative of an age of the patient, where the first numerical measure is determined by processing the patient data 102. For instance, the patient data 102 may include data indicating the patient's age in years (e.g., 77 years, in an example). In embodiments, the first numerical measure is a Boolean value indicative of whether the patient's age is 75 years or older. Thus, in the above example, the patient's age in years (i.e., 77 years) is processed to generate the first numerical measure indicating that the patient's age is 75 years or greater (e.g., a value of "1").

The second exemplary numerical measure of FIG. 1 is indicative of a stage of the patient's multiple myeloma disease, as determined based on the processing of the patient data 102 performed by the data processing module 104. For instance, the patient data 102 may include data indicating the ISS disease stage for the patient's multiple myeloma disease (e.g., an ISS stage of "III" in an example). In embodiments, the second numerical measure has a first Boolean value when the ISS disease stage is "III" and a second Boolean value when the ISS disease stage is "I" or "II." Thus, in the above example, the patient's ISS disease stage (i.e., "III") is processed to generate the second numerical measure indicating that the patient's ISS disease stage is "III," and not "I" or "II." In other embodiments, the second numerical measure may have a first numerical value when the ISS disease stage is "I" (e.g., "0"), a second numerical value when the ISS disease stage is "II" (e.g., "1"), and a third numerical value when the ISS disease stage is "III" (e.g., "2").

The third exemplary numerical measure of FIG. 1 is indicative of the patient's mobility, as determined based on the processing of the patient data 102 performed by the data processing module 104. For instance, the patient data 102 may include a EuroQol five dimensions questionnaire (EQ-5D) mobility score for the patient. In embodiments, the EQ-5D mobility score is processed to generate a mobility score of "0," "1," or "2" for the patient. The third exemplary numerical measure is equal to the generated mobility score.

Other or additional exemplary numerical measures 110 generated from the patient data 102 may include, for example, a numerical measure indicative of the patient's platelet count (e.g., a numerical measure indicative of whether the patient's platelet count is greater than $150 \times 10^9$/L), a numerical measure indicative of whether the patient has renal insufficiency (e.g., a numerical measure indicative of whether the patient's serum creatinine is greater than 2 mg/dL), a numerical measure indicative of a performance status of the patient (e.g., a numerical measure indicative of whether the patient's ECOG performance score is greater than or equal to 2), a numerical measure indicative of whether the patient has a history of hypertension, a numerical measure indicative of whether the patient has a history of diabetes, a numerical measure indicative of Del(17P) from FISH and cytogenetic forms, a numerical measure indicative of hyperdiploidy, a numerical measure indicative of extramedullary plasmacytoma, a numerical measure indicative of novel therapy use, a numerical measure indicative of triplet therapy use, and a numerical measure indicative of solitary plasmacytoma.

The one or more numerical measures 108 determined from the patient data 102 are received at a probability generating engine 112, which may be implemented with a computer processing system such as described above for module 104. The probability generating engine 112 is configured to determine a probability 118 that the patient will die within a predetermined period of time (e.g., a predetermined period of time starting from the date in which the patient was diagnosed with multiple myeloma). In embodiments, the probability 118 indicates whether the patient will die within 180 days (e.g., within 180 days of the patient's myeloma diagnosis), 1 year, 2 years, 3 years, 4 years, or 5 years. In embodiments, the probability generating engine 112 is a computer-based system for automatically generating the probability 118 that requires no human intervention or minimal human intervention. The probability generating engine 112 may determine the probability 118 based on the numerical measures 108 and a numerical computer model. The numerical computer model includes weighting factors for each of the numerical measures 108, and the weighting factors are determined based on reference data 114.

The numerical computer model is applied to the numerical measures 108 to determine the probability 118. In embodiments where the first, second, and third numerical measures 110 are generated, the numerical computer model includes a first variable and an associated first weighting factor, a second variable and an associated second weighting factor, and a third variable and an associated third weighting factor. The first variable receives a value of the first numerical measure, the second variable receives a value of the second numerical measure, and the third variable receives a value of the third numerical measure. By applying the numerical computer model to the first, second, and third numerical measures in this manner, the probability 118 for the patient data 102 is determined. It is noted that the numerical computer model may include other or additional variables that receive values for other numerical measures. The other or additional numerical measures may include, for example, numerical measures indicative of the patient's platelet count, Del(17P) from FISH and cytogenetic forms, hyperdiploidy, extramedullary plasmacytoma, novel therapy use, triplet therapy use, solitary plasmacytoma, performance status, whether the patient has renal insufficiency, whether the patient has a history of hypertension, and whether the patient has a history of diabetes. In generating the probability 118, the numerical computer model may be applied to one or more of these other numerical measures including in combination with previously mentioned numerical measures.

To generate the numerical computer model used in the probability generating engine 112, a model generation module 106 may be used. The model generation module 106 receives the reference data 114 and uses the reference data 114 to determine the weighting factors for the model, e.g., using one or more regression analyses, imputation procedures used to add data that is missing from the reference data 114, and a model training procedure, all of which are discussed in further detail below. In embodiments, the reference; data 114 is data for a plurality patients diagnosed with multiple myeloma. Specifically, in embodiments, the reference data includes for respective patients of the plurality of patients (i) data for multiple variables of a set of patient variables, and (ii) survival data indicative of an amount of time between the patient's multiple myeloma diagnosis and the patient's death or between the multiple myeloma diagnosis and a date (e.g., a date in a database) at which the patient is last known to be alive. The survival data of the reference data 114 spans a range of different amounts of time, and the reference data 114 has been accepted as usable for training the numerical computer model, in embodiments.

In embodiments, the weighting factors of the numerical computer model are determined via a machine learning application trained based on the reference data 114. Specifically, the machine learning application may be a logistic regression classifier or a Cox regression classifier, in embodiments. The model generation module 106 performs various procedures (e.g., imputation procedures to add data that is missing from the reference data 114, etc.), in embodiments, in order to generate the weighting factors of the model. As illustrated in FIG. 1, the model generation module 106 provides the model to the probability generating engine 112, and the probability generating engine 112 uses the model to generate the probability 118, as explained above.

Additionally, in some embodiments, the model generation module 106 performs variable selection procedures to determine the variables that are used in the numerical computer model. Specifically, in embodiments described in further detail below, the model generation module 106 is configured to process the reference data 114 via one or more regression analyses (e.g., univariate regression analyses, multivariate regression analyses, etc.) to automatically determine predictors of death in patients diagnosed with multiple myeloma. Both logistic regression analyses and Cox regression analyses may be used. Such predictors of death are utilized as variables in the numerical computer model. In embodiments, the model generation module 106 further performs imputation procedures to automatically generate data for variables of the reference data 114 determined to have missing data. Then, after determining the variables (e.g., predictors) for the model and imputing data as necessary, the model generation module 106 trains the numerical computer model to determine the weighting factors for the respective variables. The weighting factors thus take into account the relative contributions of each of the predictors.

With the trained numerical computer model in place, the patient data 102 may be scored by applying the numerical computer model as described above. The probability 118 for the patient data 102 is a probability that the patient will die within a predetermined period of time. In embodiments, the probability generating engine 112 implements multiple models, where each model is associated with a particular period of time. For instance, in an embodiment, the probability generating engine 112 utilizes a first numerical computer model to generate a probability that a patient will die within 180 days. The first numerical computer model includes variables configured to receive a particular set of numerical measures.

The probability generating engine 112 may further utilize a second numerical computer model to generate a probability that the patient will die within a longer amount of time (e.g., 1, 2, 3, 4, 5 years). The second numerical computer model may include variables that are configured to receive numerical measures that are different from those received by the first numerical computer model. The use of the different numerical computer models for the different periods of time reflects the fact that some predictors of death are more applicable when considering shorter amounts of time (e.g., death within 180 days) and less applicable when considering longer amounts of time (e.g., death within 1 year, 2 years, 3 years, 4 years, 5 years, etc. and vice versa).

Conventionally, technological solutions based on single, static predictors have been used to predict mortality in patients diagnosed with multiple myeloma. In some conventional approaches, patient mortality may be predicted based on a revised version of the International Staging System (ISS) for multiple myeloma from the International Myeloma Working Group. The revised ISS is a disease-specific predictor and considers only the stage of the patient's disease and not patient-specific characteristics (e.g., the patient's age, etc.). The use of the revised ISS is a technological solution for predicting death because it is based on a quantitative analysis of relevant data (e.g., data indicative of the stage of the patient's disease, etc.). In other conventional approaches, patient mortality is predicted based on a frailty score, whereby the patient is categorized into one of three groups (e.g., fit, intermediate fit, and frail) and the probability of death is assessed based on the frailty score. The frailty score is a patient-specific predictor and considers only characteristics of the patient and not disease-specific characteristics. The use of the frailty score is a technological solution for predicting mortality because it is based on a quantitative analysis of relevant data (e.g., data indicative of patients' age, functional status, comorbidities, etc.).

The techniques of the present disclosure provide solutions rooted in computer technology that improve on the conventional technological solutions described above. As described herein, rather than generating a probability of patient death based on a static, single predictor (e.g., a predictor that is predetermined and that does not change, such as the revised ISS or the frailty score described above), the techniques of the present disclosure provide an accurate, multivariate analysis of patient mortality that takes into account the relative contributions of multiple predictors that are determined automatically from reference data. Using the techniques of the present disclosure, large amounts of reference data are processed via regression analyses to automatically determine multiple predictors of death in patients diagnosed with multiple myeloma. In embodiments, the predictors of death determined via the regression analyses vary based on the time frame considered (e.g., some predictors are valid for predicting whether the patient will die within 180 days but not 1, 2, 3, 4, 5 years and vice versa). It is thus noted that in these embodiments, the predictors of death are not static, "one-size-fits-all" predictors that are predetermined and applied in all instances, as in the conventional approaches. After imputing data for variables of the reference data determined to have missing data, as necessary, the numerical computer model is automatically built and trained, where the numerical computer model includes the predictors of death and associated weighting factors that take into account the relative contributions of each of the predictors. The numerical computer model is then applied to new data for a patient diagnosed with multiple myeloma to generate a probability that the patient will die within a predetermined period of time. The processes described herein thus enable an accurate, multivariate analysis of patient data to be performed in a relatively fast, automated manner that requires no human intervention or only minimal human intervention. The conventional technological solutions cannot provide the automated, multivariate analysis described herein.

Figure 2A:
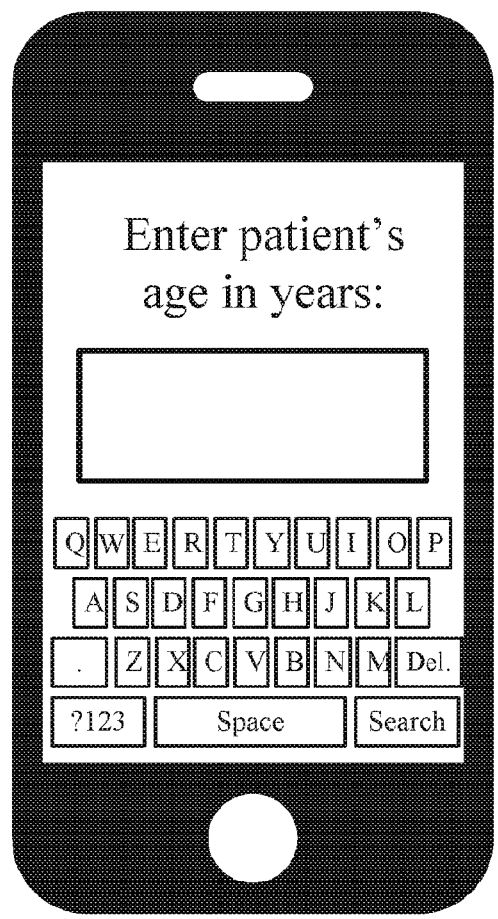
Figure 2B:
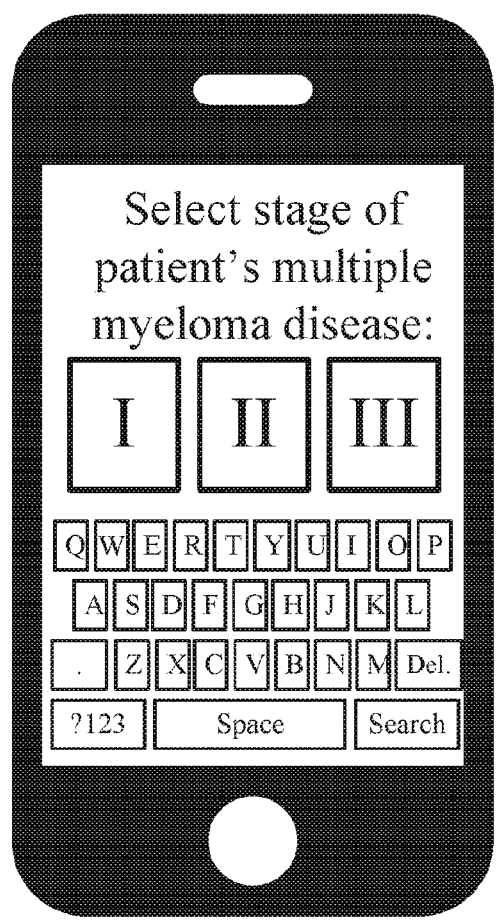
Figure 2C:
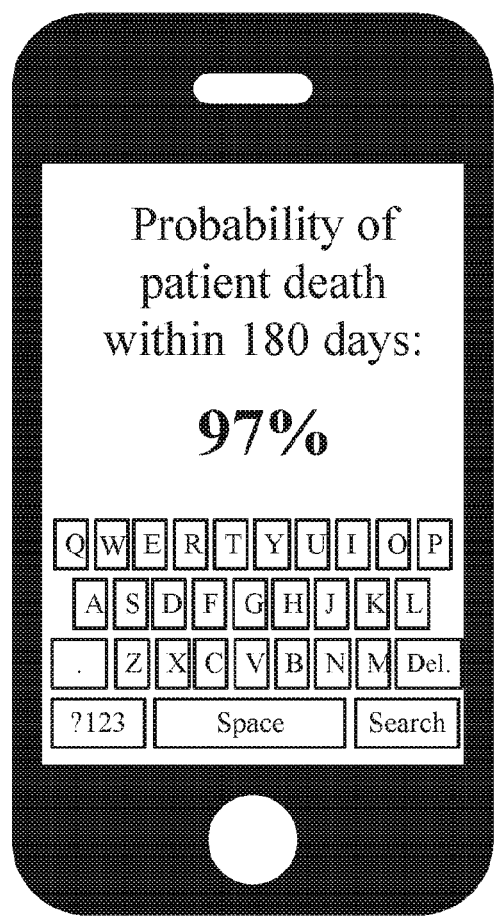

In embodiments of the present disclosure, input data for a patient diagnosed with multiple myeloma may be received via a GUI of a software application, and based on the computer-implemented systems and methods described herein, the software application generates a probability that the patient will die within a predetermined period of time. To illustrate exemplary GUIs for such a software application, reference is made to FIGS. 2A-2F. As illustrated in FIGS. 2A and 2B, in embodiments, a GUI prompts a user to provide data for various patient variables. In FIG. 2A, for instance, the Gill prompts the user to "Enter patient's age in years" and provides a text box for receiving an input from the user. In FIG. 2B, for instance, the GUI prompts the user to "Select stage of patient's multiple myeloma disease" and provides three buttons for receiving an input from the user. Based on these inputs and inputs for multiple other patient variables (e.g., ECOG performance score of patient, whether patient has history of hypertension, whether patient has renal insufficiency, patient's platelet count, patient's mobility score, whether patient has a history of diabetes, etc.) received from the user, the software application applies the trained numerical computer model and generates and displays a probability that the patient will die within a predetermined period of time. For instance, as shown in FIG. 2C, after receiving inputs from the user for multiple patient variables, the software application generates and displays the probability (e.g., "Probability of patient death within 180 days: 97%," in the example of FIG. 2C).

Figure 2E:
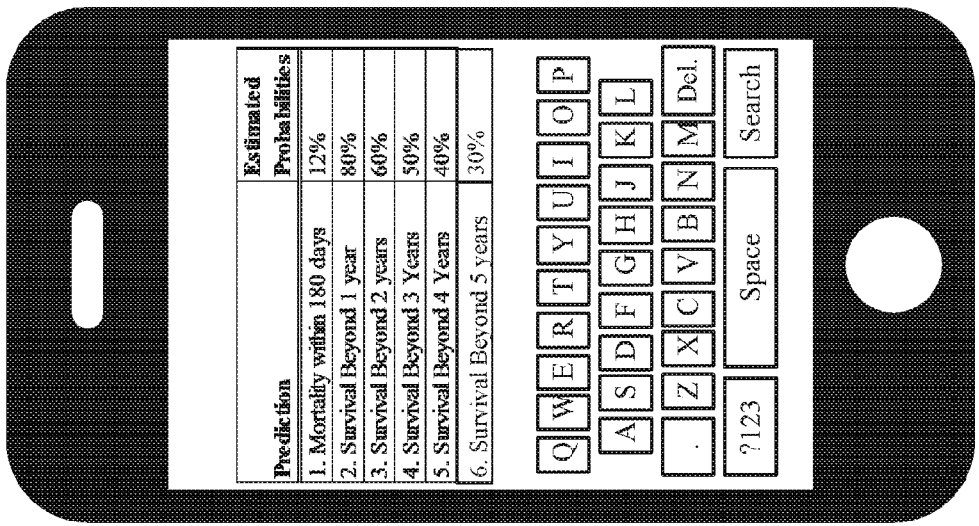
Figure 2D:
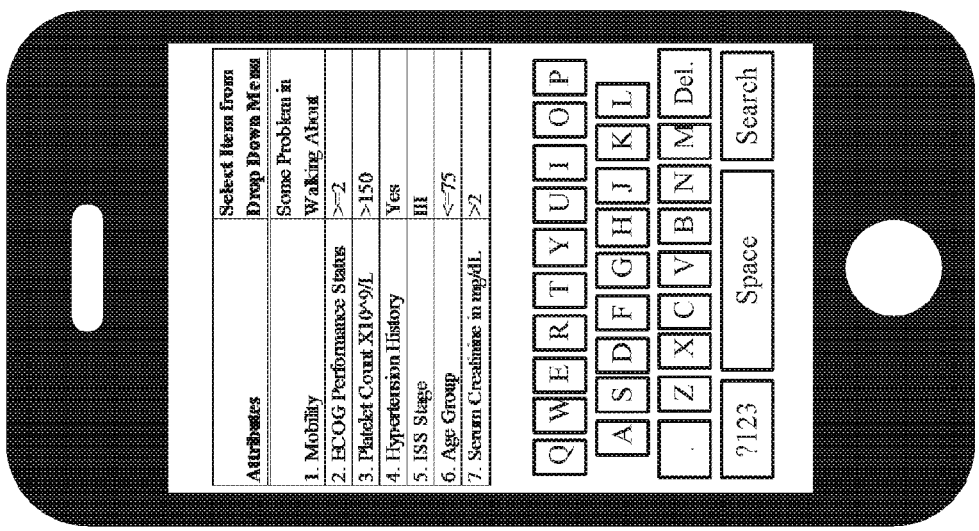

FIG. 2D illustrates another exemplary GUI for receiving input data representative of patient variables of a patient diagnosed with multiple myeloma. In this example, multiple patient variables are displayed, and for each variable, there is a corresponding drop-down menu with multiple selectable options. Although seven (7) variables are illustrated in the example of FIG. 2D, it is noted that these variables are examples only and that in other embodiments, a different set of variables may be presented to the user. Other or additional variables that may be used include variables indicative of the patient's history of diabetes, Del(17P) from FISH and cytogenetic forms, hyperdiploidy, extramedullary plasmacytoma, novel therapy use, triplet therapy use, and solitary plasmacytoma, among others. Based on input data received via the multiple drop-down menus, the soft rare application generates and displays output data on predicted patient mortality. For instance, as shown in FIG. 2E, after receiving the input data, the software application generates a table with estimated probabilities for various amounts of time (e.g., 180 days, 1 year, 2 years, 3 years, 4 years, 5 years, etc.). Specifically as shown in FIG. 2E, the table presents probabilities for "mortality within 180 days," "survival beyond 1 year," "survival beyond 2 years," "survival beyond 3 years," "survival beyond 4 years," and "survival beyond 5 years."

Figure 2F:
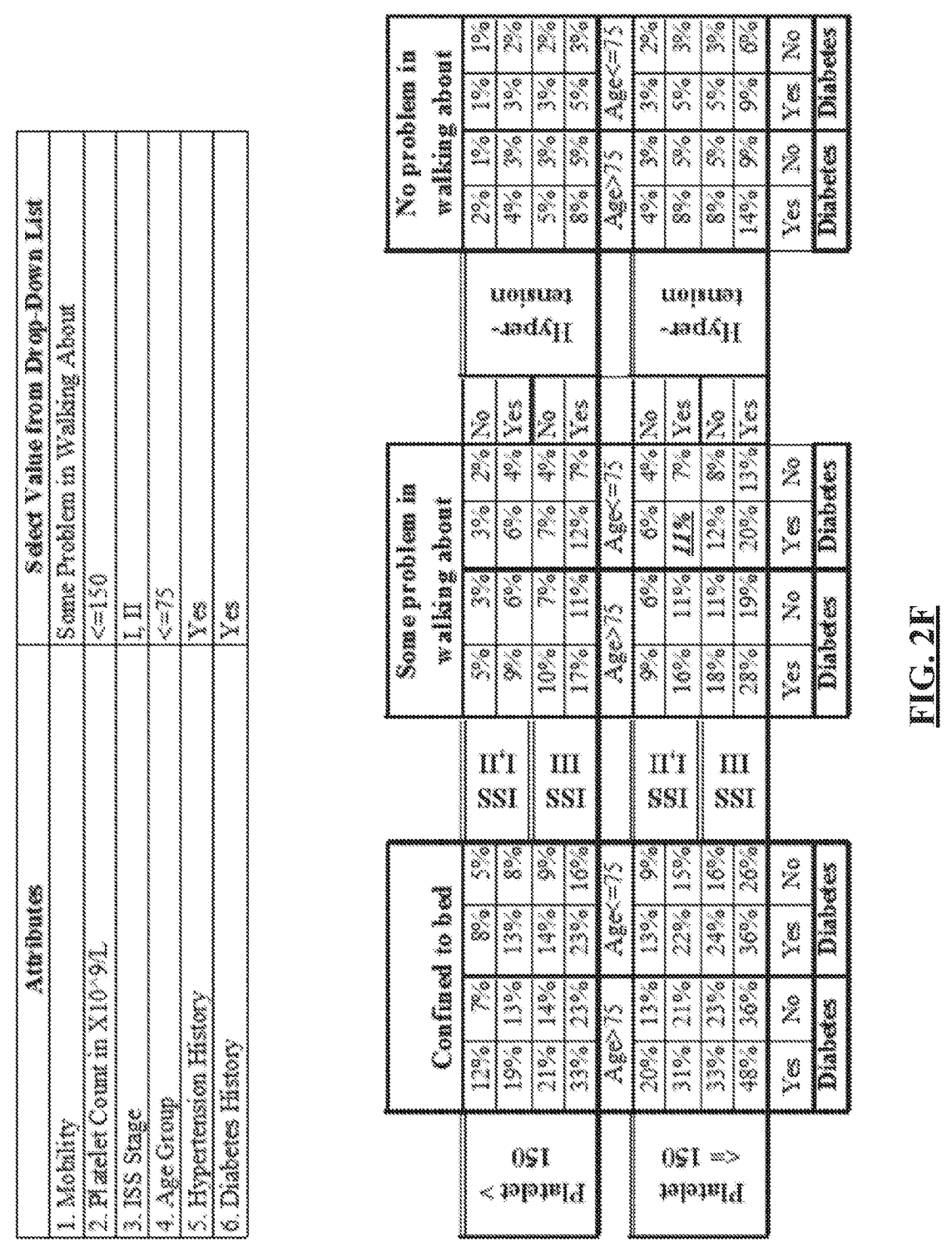

FIG. 2F illustrates another exemplary display generated according to the computer-implemented techniques of the present disclosure. In an upper portion of the exemplary display, multiple patient variables are displayed, and for each variable, there is a corresponding drop-down menu with multiple user-selectable options. Although six (6) variables are illustrated in the example of FIG. 2F, it is noted that these variables are examples only and that in other embodiments, a different set of variables may be presented to the user. An exemplary use of a drop-down menu is illustrated in FIG. 2G. As shown in this figure, when a drop-down menu for the "Mobility" variable is accessed, the user can select one of multiple different values for the variable (e.g., "Confined to Bed," "Some Problem in Walking About," "No Problem in Walking About," etc.). The other drop-down menus shown in the embodiment of FIG. 2F may operate similarly by allowing the user to select values for each of the respective variables. Selectable options for each of the drop down menus are reflected, in the chart in the lower portion of FIG. 2F.

Based on input data received via the multiple drop-down menus, the software application highlights a probability value found in a prediction matrix. An exemplary prediction matrix is illustrated in a lower portion of the exemplary display of FIG. 2F, which is based on application of the trained numerical computer model and which may be displayed to a user (e.g., physician) after inputting values for variables as described above. The patient variables considered in the embodiment of FIG. 2F may be used to estimate the probability that the patient will die within a relatively short amount of time (e.g., 180 days). In this example, a probability value of "11%" is underscored, in boldface, and italicized to indicate that this is the probability value corresponding to the inputs received via the drop-down menus. Of course, other suitable ways of highlighting the relevant values may be used other than or in addition to underlining, boldface, italics, such as for instance color coding the block or text for the relevant value against a different color background, etc. For instance, as can be seen from the prediction matrix, the underscored, boldface, and italicized 11% corresponds to the inputs "Some problem in walking about," "platelet count≤150×10$^9$/L," "IBS stage I or II," "Age 75 years," "history of hypertension," and "history of diabetes." In other words, given these inputs received via the drop-down menus, the software application's probability generating engine (e.g., the probability generating engine 112 described above with reference to FIG. 1) determines that there is an 11% probability that the patient will die within the relatively short amount of time, which may be 180 days or other first predetermined period of time. To generate the prediction matrix, all possible combinations of input values are provided to the probability generating engine, which generates probability values corresponding to each of the different combinations. The probability values are then put into a matrix form, such as that illustrated in FIG. 2F, and the applicable values thereof are coordinated with ride-based selection criteria so as to highlight the appropriate value(s) of the matrix based upon the selected variables. The generation of prediction matrices is described in further detail below.

FIG. 2H illustrates another exemplary display generated according to the computer-implemented techniques of the present disclosure. Similar to the embodiment shown in FIG. 2F, in an upper portion of the exemplary display, multiple patient variables are displayed, and for each variable, there is a corresponding drop-down menu with multiple user-selectable options. Although seven (7) variables are illustrated in the example of FIG. 2H, it is noted that these variables are examples only and that in other embodiments, a different set of variables may be presented to the user. Based on input data received via the multiple drop-down menus, the software application highlights a probability value found in a prediction matrix.

An exemplary prediction matrix is illustrated in a lower portion of the exemplary display of FIG. 2H, which is based on application of the trained numerical computer model and which may be displayed to a user (e.g., physician) after inputting values for variables as described above. The patient variables considered in the embodiment of FIG. 2H, may be used to estimate the probability that the patient will survive a relatively long amount of time (e.g., 3 years). In this example, a probability value of "81%" is underscored, in boldface, and italicized to indicate that this is the probability value corresponding to the inputs received via the drop-down menus. As can be seen from the prediction matrix, the underscored, boldface, and italicized 81'%© corresponds to the inputs "no problem in walking about,"

"age less than or equal to 75 years," "platelet count greater than 150×10⁹/L," "serum creatinine greater than 2 mg/dL," "a history of diabetes," "an ISS stage of I or II," and "use of novel therapies that is less than or equal to 1." In other words, given these inputs received via the drop-down menus, the software application's probability generating engine (e.g., the probability generating engine 112 described above with reference to FIG. 1) determines that there is an 81% probability that the patient will survive the relatively long amount of time, which may be at least 3 years or other second predetermined period of time. To generate the prediction matrix, all possible combinations of input values are provided to the probability generating engine, which generates probability values corresponding to each of the different combinations. The probability values are then put into a matrix form, such as that illustrated in FIG. 2H, and the applicable values thereof are coordinated with rule-based selection criteria so as to highlight the appropriate value(s) of the matrix based upon the selected variables.

Figure 3A:
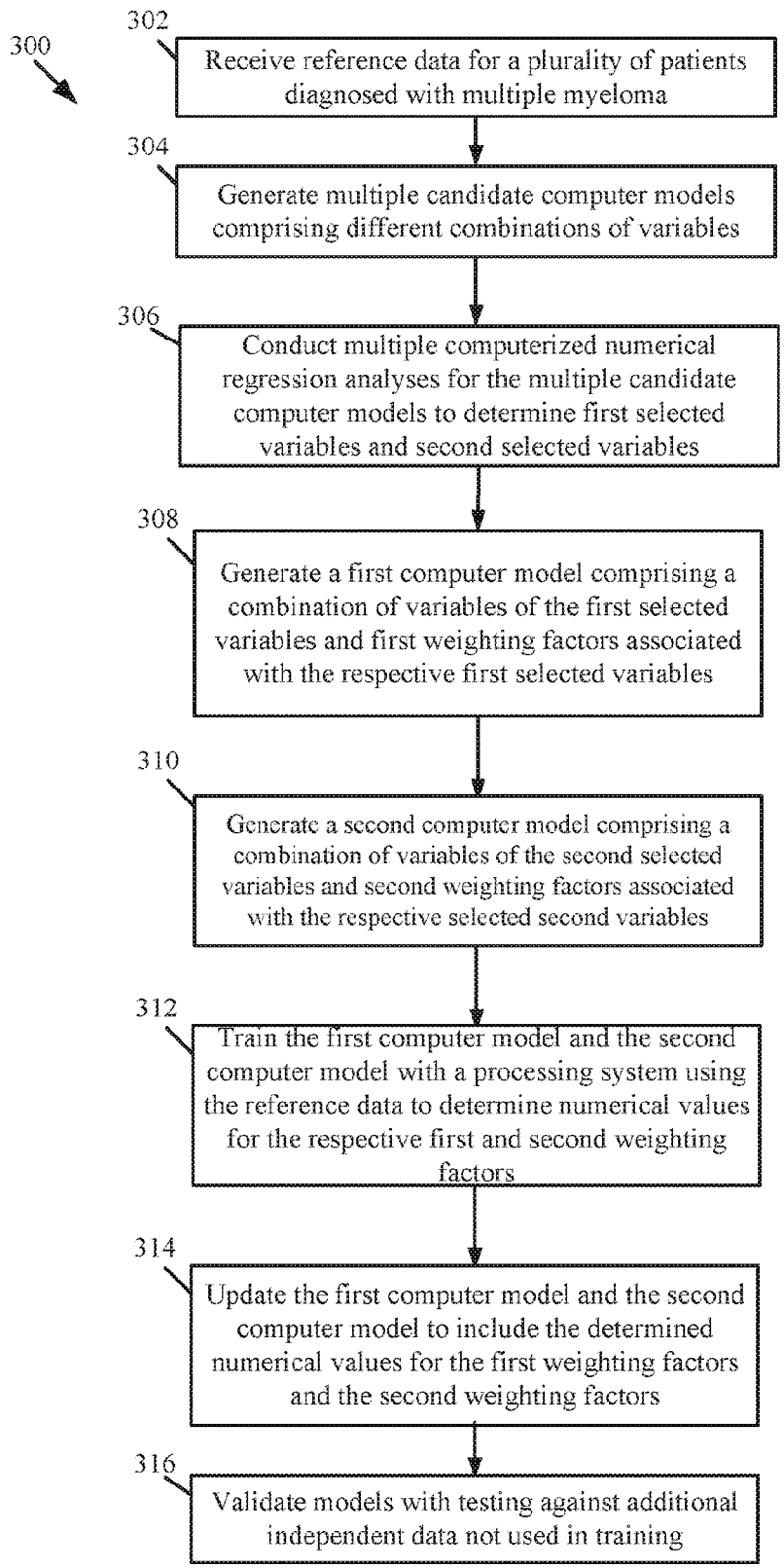
FIG. 3A is a flowchart depicting steps of an exemplary method for constructing a numerical computer model to generate a probability that a patient diagnosed with multiple myeloma will die within a predetermined period of time.
Figure 3K-2:
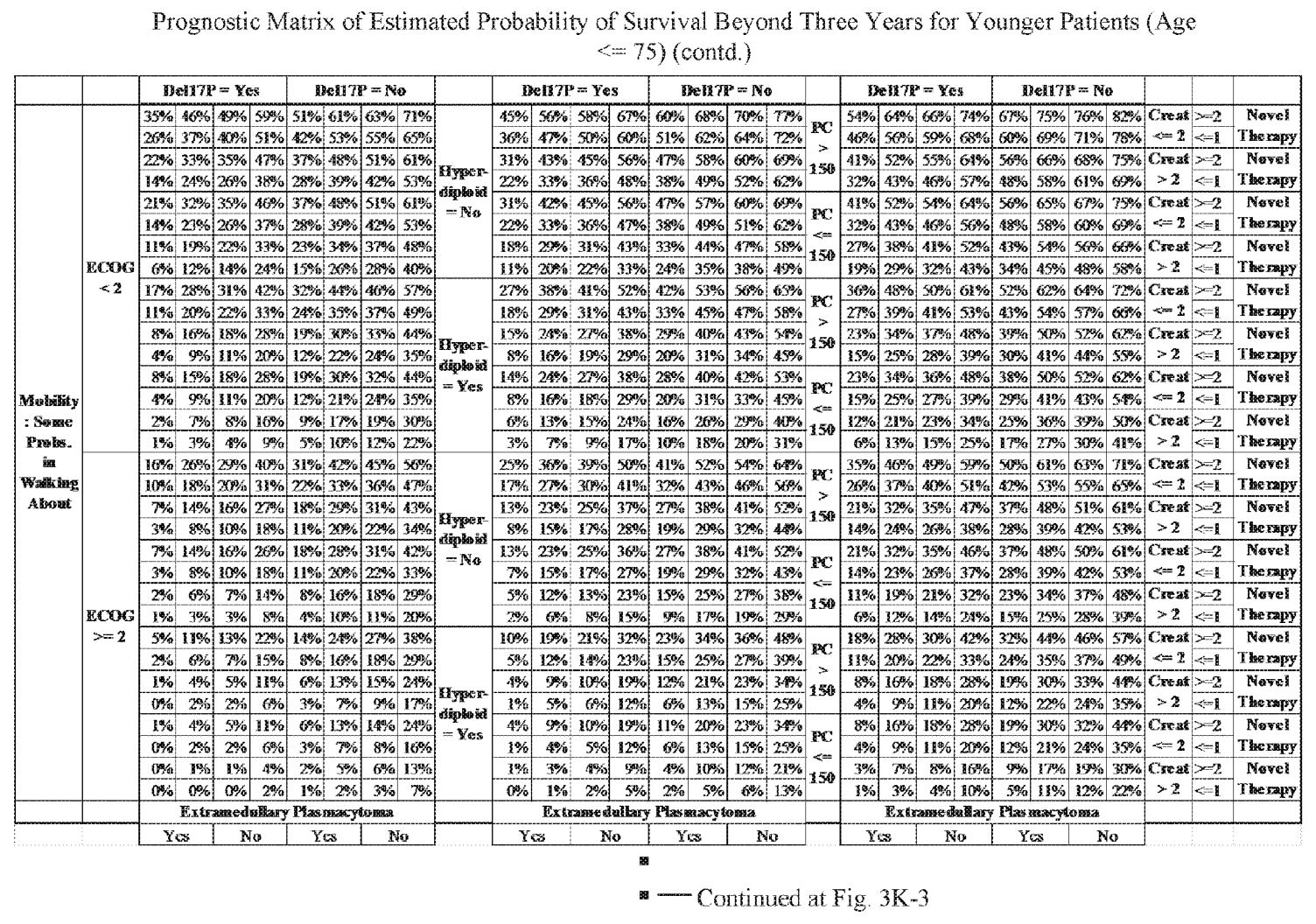

FIG. 3A is a flowchart 300 depicting operations of an exemplary method for constructing a numerical computer model to generate a probability that a patient diagnosed with multiple myeloma will die within a predetermined period of time. As described above with reference to FIG. 1, a model generation module 106 receives reference data 114 for a plurality of patients diagnosed with multiple myeloma and uses the reference data 114 to (i) determine a set of variables to be used in a numerical computer model (e.g., perform variable selection), where each variable has been determined to be predictive of death in patients diagnosed with multiple myeloma, and (ii) determine weighting factors for each of the variables of the numerical computer model. The exemplary operations depicted in the flowchart 300 of FIG. 3A provide further details on the variable selection and training of such a numerical computer model. The exemplary operations depicted in the flowchart 300 of FIG. 3A also provide details on the generation of (i) a first computer model configured to generate probability data that a patient satisfying certain first selectable criteria will die within a first predetermined period of time (e.g., 180 days), and (ii) a second, different computer model (e.g., the second computer model comprising different variables than the first computer model, etc.) configured to generate probability data that a patient satisfying certain second selectable criteria will die within a second predetermined period of time (e.g., 1, 2 3, 4, or 5 years).

At 302, reference data for a plurality of patients diagnosed with multiple myeloma is received. The reference data comprises for respective patients of the plurality of patients (i) data for variables of a set of patient variables, and (ii) survival data indicative of an amount of time between the patient's cancer diagnosis and the patient's death or between the cancer diagnosis and a date at which the patient is last known to be alive. The reference data has been accepted as usable for training a numerical computer model, in embodiments.

To illustrate examples of the patient variables that may be represented in the reference data, reference is made to FIGS. 3B, 3C, and 3D. FIG. 3B depicts examples of "patient-specific" variables (e g variables that are related to the patient and not directly related to multiple myeloma) that may be represented in the reference data. The patient-specific variables may include age (e.g., whether patient's age is 75 years or greater, whether patient's age is 70 years or greater), body mass index, ECOG performance status score, history of diabetes, history of hypertension, history of venous thromboembolism (VIE), del(1.7p) from FISH and cytogenetic forms, 1(4.14) from FISH and cytogenetic forms, T(11.14) from FISH, T(14.16) from FISH, history of MGUS, history of smoldering myeloma, and hyperdiploidy.

FIG. 3C depicts examples of "disease-specific" variables (e.g., variables that are related to the multiple myeloma disease) that may be represented in the reference data. The disease-specific variables may include lactic acid dehydrogenase (e.g., whether lactic acid dehydrogenase is greater than 300 IU/L), history of solitary plasmacytoma, extramedullary plasmacytoma, immunoglobulin IgG class (e.g., whether immunoglobulin IgG class is 5 g/dL or greater), albumin (e.g., whether albumin is greater than 3.5 g/dL), ISS disease stage, myeloma bone involvement, hypercalcemia (e.g., whether serum calcium is greater than or equal to 11.5 mg/dL), renal insufficiency (e.g., whether serum creatinine is greater than 2 mg/dL), anemia (e.g., whether hemoglobin is less than 10 g/dL or whether it is greater than 2 below LLN), clonal bone marrow plasma cells (e.g., whether clonal bone marrow plasma cells are 10% or greater), serum monoclonal protein (e.g., whether serum monoclonal protein is 3 g/dL or greater), serum free light chain abnormality, pathological fracture, platelet count (e.g., whether platelet count is greater than 150×10⁹/L), IMWG risk, and beta 2 microglobulin (e.g., whether beta 2 microglobulin is greater than or equal to 5.5 mg/L), FIG. 3D depicts examples of "HRQOL from EQ-5D" and "novel therapy" variables that may be represented in the reference data. The FIRQOL from EQ-5D variables may include "self-care from EQ-5D" and "mobility from EQ-5D." The novel therapy variables may include a variable that takes into account a number of novel therapies used by the patient and variables that take into account whether the patient has used triplet therapy, IMID-containing therapy, and PI-containing therapy, respectively. In embodiments, "triplet therapy" refers to a treatment regimen that uses at least three medications or drugs, and the triplet therapy variable may be used to store a Boolean value (e.g., "0" or "1," or "yes" or "no") indicative of whether the patient has used triplet therapy or not.

In some embodiments, the reference data comprises data from a non-interventional trial and/or registry. Non-interventional trials or registries allow some latitude in the reporting of observations and procedures by site investigators, leading to a larger degree of missing data than in controlled clinical trials. Accordingly, the computer-implemented procedures described herein for generating the numerical computer model address the issue of data incompleteness (e.g., via imputation procedures, as described herein). In embodiments, the registry used to generate the numerical computer model is the Connect® MM Registry (NCT01081028). This registry enrolled two cohorts. The first cohort has adequate follow-up (e.g., median 33.5 months, N=1493) for analysis. By contrast, analysis for the second cohort is pre-mature due to inadequate follow-up. The Connect MM Registry vitas designed as a prospective, observational, longitudinal, multicenter study of patients with newly diagnosed multiple myeloma.

There is no planned investigational agent, prescribed treatment regimen, or mandated intervention in the Connect MM Registry study. The treating physician determines the enrolled patient's therapy for newly diagnosed multiple myeloma according to his or her clinical judgment. Inclusion criteria are limited to patients who are newly diagnosed with symptomatic multiple myeloma within 2 months of enrollment, age greater than or equal to 18 years, willingness and ability to sign informed consent, and an agreement by the patient to complete patient questionnaires alone or with minimal assistance. No exclusion criteria are used. The data of this registry came largely from community sites (81.1%) while the prevalence of academic and government investigational sites was not significant (17.6% and 1.3%, respectively). An evaluation of the registry's baseline data in comparison to the National Comprehensive Cancer Network's suggested diagnostic work-up for multiple myeloma found that allowing physician discretion in diagnostic data to be collected, as is usually done for non-interventional registries, led to incomplete data. As noted above and described in further detail below, the computer-implemented processes used to build the numerical computer model take into account the issue of data incompleteness.

At 304, multiple candidate computer models comprising different combinations of the variables of the set of patient variables are generated. Each of the candidate computer models includes multiple weighting factors associated with the variables, and each variable of each candidate computer model has an associated weighting factor. At 306, multiple computerized numerical regression analyses for the multiple candidate computer models are conducted based on the data for the variables and the survival data to determine first selected variables and second selected variables from the set of patient variables. The first selected variables satisfy one or more selection criteria to be deemed predictive of mortality for a first predetermined period of time (e.g., mortality within 180 days from diagnosis) for patients diagnosed with multiple myeloma, and the second selected variables satisfy one or more selection criteria deemed to be predictive of mortality for a second predetermined period of time mortality within 1, 2, 3, 4, or 5 years front diagnosis) for patients diagnosed with multiple myeloma.

In embodiments, performing the steps 304 and 306 begins with univariate screening to reduce the number of variables and then proceeds to a variable selection procedure. Specifically, in embodiments, univariate analyses are conducted with the intent of determining the degree of missingness on each variable and the statistical significance of the variable in predicting the dependent measure (e.g., death within a predetermined period of time). In some embodiments, variables significant at the p>0.15 level and with less than 60% missing data are screened in.

In embodiments, in building the first computer model used to generate a probability that a patient diagnosed with multiple myeloma will die within 180 days, the univariate analyses are logistic regression analyses conducted for the discrete variable of mortality within 180 days. Exemplary SAS code for the logistic regression analyses follows, where d180 is the discrete dependent variable:

```
proc logistic data = Edeath descending;
    model d180 = &var/risklimits;
    ods output ParameterEstimates=&univ_est NObs = &univ_miss;
run;
```

By contrast, in building the second computer model used to generate a probability that a patient diagnosed with multiple myeloma will die within 1 year, 2 years, 3 years, 4 years, or 5 years, the univariate analyses are Cox regression analyses, in embodiments. In embodiments, the Cox regression analyses are used to handle censored data. Data is censored when patients discontinue or are otherwise lost to follow-up. From such data, it cannot be determined if the patients are currently dead or alive, and the data merely indicates that after a certain duration of follow-up, the patient discontinued follow-up or was otherwise lost to follow-up. In embodiments, longer time frames involve more censoring of data and thus, in predicting late mortality (e.g., probability of death within 1 year, 2 years, 3 years, 4 years, 5 years, etc., as opposed to a shorter amount of time such as 180 days), Cox regression analyses are used instead of logistic regression. When considering the 180-day time frame, there is little censoring of data, and when there is censoring of data, it can be assumed that the patient is alive, thus leading to a dichotomous variable (i.e., alive or dead at day 180). The simpler logistic regression analyses are used for shorter time frames such as this.

The reference data from the Connect MM Registry includes data for thirty-seven (37) different patient variables (e.g., the 37 different variables shown in FIGS. 3B, 3C, and 3D), in embodiments. In embodiments, using the univariate screening procedure described above, thirteen (13) variables are screened through the logistic regression analyses, and twenty-eight (28) variables are screened through Cox regression analyses. The average amount of missing data for the logistic-regression-screened variables is 9.23%, and the average amount of missing data for the Cox-regression-screened variables is 15.4%, in embodiments.

To address the issue of missing data in the reference data, a number of imputed datasets are created, in embodiments. The relative efficiency (RE) of multiple imputation is given by the following:

$$RE=(1+\lambda/m)^{-1},$$

where $\lambda$ is the fraction of missing information about the parameter being estimated, and m is the number of imputed datasets. The fraction of missing data is roughly proportional to the average amount of missing data. For three (3) imputations, the RE is 0.9375 and 0.8571 for missing fractions of 20% and 50%, respectively. For the intended ten (10) imputations, the RE increases to 0.9804 and 0.9524, respectively.

In embodiments, Rubin's imputation framework may be used for the imputation analysis. This analysis involves (i) assuming an imputation model, (ii) obtaining the predictive distribution of the missing data conditional on observed data and distribution parameters, and (iii) producing multiple imputed datasets using the predictive distribution. Analysis under multiple imputation is robust under less restrictive assumptions of Missing at Random (MAR) compared to the case-wise deletion of data records with any data missing on any variable. Further, case-wise deletion of data missing on any variable leads to considerable loss of information on other collected variables. In embodiments, the imputation model utilized is the Fully Conditional Specification (FCS) as recommended in "Multiple Imputation of Discrete and Continuous Data by Fully Conditional Specification," van Buuren S., Statistical Methods in Medical Research, 2007; 16:219-242, which is incorporated herein by reference in its entirety. All variables (including those screened out) are used in the imputation model to extract all information on the missingness of the predictors contained in the dataset, and ten imputations are generated. Exemplary SAS code for this analysis is as follows:

```
proc mi data=os nimpute=10 seed=5122017 out=osm;
    class agen hispan bmi issstagen ecogn ...;
    fcs logistic(agen hispan bmi issstagen ecogn ...);
    var agen hispan bmi issstagen ecogn ...;
run;
```

In other embodiments, the imputation model utilized is the Markov Chain Monte Carlo (MCMC) method under the multivariate normal model. All variables (including those screened out) are used in the imputation model to extract all information on the missingness of the predictors contained in the dataset, and ten imputations are generated, in embodiments. Exemplary SAS code for performing this analysis is as follows:

```
proc mi data =Edeath nimpute = 10 seed = 651467 out=Edeathm ;
var agen hispan bmi issstagen mhecogynn ......partial list of
    variables ....;
run;
```

In embodiments, following the univariate screening and imputation procedures described above, a computer-implemented variable selection procedure is performed. In the variable selection procedure, the imputed datasets are stacked on top of each other, and the multivariate logistic and Cox regressions are run using underweighted observations with the underweighting being proportional to the number of imputed datasets and to the degree of missingness. The variables used are those screened in under the univariate regression analyses described above. The SAS code for the first computer model (e.g., the logistic model, as described herein) requesting all possible models follows. The weight is equal to (1−f)/(# of imputations), where f is the average fraction of missing data.

```
proc logistic data = Edeathm2 ;
model d180 (event = 'yes') = agen issstagen mhecogynn imwg_risk
mhdiabn mhhyn calcium creat plat_ct caref mobf gp_17p_ad
novelf/
    selection = score details lackfit ;
        weight wt;
run;
```

The code "selection=score" provides the score statistic for all possible models. In embodiments, the difference in score statistics between models is a chi-squared distribution with degrees of freedom given by the difference in the number of variables in the models. In embodiments, starting with the best 1-variable model, movement in one variable increments to the best k-variable model is performed until the incremental score statistic is less than the critical value obtained as the 0.1-level Wald $X^2$ chi-square value for one degree of freedom. In embodiments, several models with score statistics in the neighborhood of that for the best k-variable model are considered as candidate models, and an appropriate model is selected. In embodiments, for each candidate model, multivariate Logistic/Cox regression are fit on each of the 10 imputed datasets, and the average Bayesian Information Criterion (BIC) value is calculated. The final multivariate model is selected as the candidate model with the minimum average BIC amongst models judged to be clinically appropriate.

In embodiments, in building the first computer model for generating a probability that a patient diagnosed with multiple myeloma will die within 180 days, the variable selection procedure described above may result in the selection of seven (7) variables. As described herein, these variables are selected using a stacked, weighted logistic regression analyses. These variables are illustrated in FIG. 3E, which lists the seven variables under a column heading "Characteristic," In embodiments, in building the second computer model for generating a probability that a patient diagnosed with multiple myeloma will die within 1 year, 2 years, 3 years, 4 years, or 5 years, the variable selection procedure described above results in the selection of ten (10) variables. As described herein, these variables are selected using a stacked, weighted Cox regression analyses. These variables are illustrated in FIG. 3F-1, which lists the ten variables under a column heading "Characteristic." In other embodiments, in building the second computer model for generating a probability that a patient diagnosed with multiple myeloma will die within 1 year, 2 years, 3 years, 4 years, or 5 years, the variable selection procedure described above results in the selection of eleven (11) variables. As described herein, these variables are selected using a stacked, weighted Cox regression analyses. These eleven variables are illustrated in FIG. 3F-2.

At the conclusion of steps 304 and 306 of FIG. 3A, first and second selected variables from the set of patient variables are determined, where the first selected variables are deemed predictive of mortality for the first predetermined period of time (e.g., death within 180 days) and the second selected variable are deemed predictive of mortality for the second predetermined period of time (e.g., death within 1, 2, 3, 4, or 5 years). At 308, the first computer model comprising combination of variables of the first selected variables and first weighting factors associated with the respective first selected variables is generated, and at 310, the second computer model comprising a combination of variables of the second selected variables and second weighting factors associated with the respective selected second variables is generated. At 312, the first computer model and the second computer model are trained using the reference data to determine numerical values for the respective first and second weighting factors.

The training of the first computer model may include (i) processing the reference data to determine, for patients represented in the reference data, numerical measures for respective variables of the first selected variables, and (ii) conducting a first computerized numerical regression analysis based on the determined numerical measures to determine the first weighting factors. Likewise, the training of the second computer model may include (i) processing the reference data to determine, for patients represented in the reference data, numerical measures for respective variables of the second selected variables, and (ii) conducting a second computerized numerical regression analysis based on the determined numerical measures to determine the second weighting factors. For example, in an embodiment in which the first or second selected variables include a variable indicative of an age of the patient, the reference data is processed to determine, for respective patients represented in the reference data, numerical values corresponding to the patients' ages. Likewise, in an embodiment in which the first or second selected variables include a variable indicative of a stage of the patient's multiple myeloma disease, the reference data is processed to determine, for respective patients represented in the reference data, numerical values corresponding to disease stages. After determining the numerical measures, the aforementioned numerical regression analyses are conducted based on the numerical measures and survival data for the respective patients represented in the reference data to determine the weighting factors of the respective first and second computer models.

In embodiments, a machine learning approach is used to build and train the first and second computer models. Specifically, in embodiments, reference data for a plurality of patients diagnosed with multiple myeloma is used, and numerical measures are determined from the reference data. The determined numerical measures for the first computer model associated with early stage mortality (e.g., death within 180 days of multiple myeloma diagnosis) may include one or more of the numerical measures 422 described below with reference to FIG. 4A, among other numerical measures. The determined numerical measures for the second computer model associated with late stage mortality (e.g., death within 1, 2, 3, 4, or 5 years of multiple myeloma diagnosis) may include one or more of the numerical measures 472 described below with reference to FIG. 4B, among other numerical measures. In constructing the first computer model, the determined numerical measures may be combined in a logistic regression classifier, which uses the determined numerical measures and the survival data for the patients represented in the reference data to generate weighting factors for the numerical measures. In constructing the second computer model, the determined numerical measures may be combined in a Cox regression classifier, which uses the determined numerical measures and the survival data for the patients represented in the reference data to generate weighting factors for the numerical measures.

In embodiments, the training of the first and second computer models may include combining the inferences for the regressions applied to each imputed dataset. The training of the first computer model for generating a probability that a patient diagnosed with multiple myeloma will die within 180 days will now be described. By Rubin's imputation framework, the estimate of a parameter of interest is the average of estimates from each imputed dataset. Such an estimate is efficient and unbiased under MAR assumptions. As described above, in building the numerical computer model for mortality within 180 days, the variable selection procedure results in the selection of the seven (7) variables shown in FIG. 3E, in embodiments. The separate estimates and the combined inferences may be obtained using the following exemplary SAS code for the seven selected variables, in embodiments:

```
proc logistic data=Edeathm2;
model d180 (event = 'Yes') = agen issstagen mhecogynn mhhyn
creat plat_ct mobf /risklimits details lackfit covb;
by _Imputation_;
ods output ParameterEstimates=lgparms CovB=lgcovb;
run;
proc mianalyze parms=lgparms
covb=lgcovb;
modeleffects Intercept agen issstagen mhecogynn mhhyn creat
plat_ct mobf;
ods output ParameterEstimates=est1;
run;
```

The output dataset est1 above contains the estimates of the intercept parameter α and the regression coefficients β's for each predictor $x_i$ in the logistic model given by $$\pi(x) = \frac{\exp\left(\alpha + \sum_{i=1}^{p} \beta_i x_i\right)}{1 + \exp\left(\alpha + \sum_{i=1}^{p} \beta_i x_i\right)},$$

where π(x) is the probability of the event corresponding at a vector of predictor values x. Exponentiation of the parameter estimates and confidence limits provides the odds ratios for a one point increment in the predictor variable. In embodiments, all of the variables for the 180-day-mortality numerical computer model listed in FIG. 3E, with the exception of the mobility variable, are dummy coded as binary values 0 and 1 because they are dichotomized variables. In embodiments, the mobility variable is ordinal and takes three levels from 0 to 2, and its odds ratio represents, on average, the change in odds for every increase in the level of mobility. FIG. 3E provides a summary of inferences from the final logistic model using multiple imputation. The odds ratio of 1.70 implies that the odds of mortality within 180 days for those patients with age greater than 75 years is 1.7 times that for those patients with age less than or equal to 75 years. Similar interpretations apply for other characteristics in the table.

The training of the second computer model for generating a probability that a patient diagnosed with multiple myeloma will die within 1 year, 2 years, 3 years, 4 years, or 5 years will now be described. As described above, in building this numerical model, the variable selection procedure results in the selection of the ten (10) variables listed in FIG. 3F-1, in embodiments. The separate estimates by imputation and the combined inferences may be obtained using the following exemplary SAS code for the ten selected variables:

```
proc phreg data=Edeathm2;
model dur*death(0) = agen issstagen mhecogynn mhdiabn creat
plat_ct solitary_plasmacytoma mobf gp_17p_ad triplet_therapy
by _Imputation_;
ods output ParameterEstimates=lgparms CovB=lgcovb;
run;
proc mianalyze parms=lgparms
covb=lgcovb;
modeleffects agen issstagen mhecogynn mhdiabn creat plat_ct
solitary_plasmacytoma mobf gp_17p_ad triplet_therapy;
ods output ParameterEstimates=est1;
run;
```

In other embodiments, as described above, in building the numerical computer model, the variable selection procedure results in the selection of the eleven (11) variables listed in FIG. 3F-2. The separate estimates by imputation and the combined inferences may be obtained using the following exemplary SAS code for the eleven selected variables:

```
proc phreg data=Edeathm2;
model dur*death(0) = agen issstagen mhecogynn mhdiabn creat
plat_ct mhsolynn mobf gp_17p_ad gp_hyper_ad novelf
by _Imputation_;
ods output ParameterEstimates=lgparms CovB=lgcovb;
run;
proc mianalyze parms=lgparms
covb=lgcovb;
modeleffects agen issstagen mhecogynn mhdiabn creat plat_ct
mhsolynn mobf gp_17p_ad gp_hyper_ad novelf;
ods output ParameterEstimates=est2;
run;
```

The output datasets est1 and est2 generated by the example code above contain the estimates of the regression coefficients β's for each predictor $x_i$ in the Cox model given by $$h(t, x) = h_0(t) \exp\left(\sum_{i}^{p} \beta_i x_i\right),$$

where h(t,x) is the hazard function at time I defined at a vector of predictor values x and $h_0(t)$ is the baseline hazard function. Exponentiation of the parameter estimates and confidence limits provide the hazard ratios and confidence limits for a one point increment in the predictor variable. In embodiments, all of the variables for the 1/2/3/4/5-year-mortality numerical computer model listed in FIGS. 3F-1 and 3F-2, with the exception of mobility and ISS stage, are dummy coded as binary values 0 and 1 because they are dichotomized variables. In embodiments, mobility and ISS are ordinal and take three levels, and the hazard ratio represents, on average, the change in hazard for every increase in level. FIGS. 3F-1 and 3F-2 provide a summary of inferences from the final Cox model using multiple imputation. In FIG. 3F-1, the hazard ratio of 1.89 for age implies that the hazard of mortality for those patients with age greater than 75 years is 1.89 times that for patients with age less than or equal to 75 years. Similar interpretations apply for other characteristics in the table.

At 314, the first computer model and the second computer model are updated to include the determined numerical values for the first weighting factors and the second weighting factors for each selected variable of the first and second selected variables. Accordingly, the first computer model is configured to generate probability data that a patient satisfying certain first selectable criteria will die within the first predetermined period of time (e.g., 180 days), and the second computer model is configured to generate probability data that a patient satisfying certain second selectable criteria will die within the second predetermined period of time (e.g., 1, 2, 3, 4, or 5 years). The first and second computer models are then ready to be used for generating probabilities, i.e., to receive numerical measures corresponding to variables of the respective computer models, where the numerical measures are new data for a patient, so as to generate a probability that the patient will die within the first and second predetermined periods of time. In this manner, the numerical computer models are thereafter configured to perform automated determination of probabilities for new patient data.

As described above, in some embodiments, a prediction matrix is generated, and the prediction matrix includes probability values for all possible combinations of patient input data. The generation of an exemplary prediction matrix using the 180-day-mortality numerical computer model will now be described. In some embodiments, the prediction matrix is designed to show less favorable outcomes in the bottom left corner and inure favorable outcomes towards the top right corner of the matrix. Further, in some embodiments, the variables are ordered by importance which is assessed by multiplying the odds ratio by (# of predictor levels-1). The odds ratios for the variables of interest are illustrated in the table of FIG. 3E. For instance, in embodiments, mobility is assessed to be most relevant to the matrix because 2.42×(3−1)=4.84 is the largest computed value, and accordingly, this variable is placed in a largest row header of the matrix. ECOG status is the next most important and is placed to be the largest column header of the matrix, in embodiments. The third most relevant variable, platelet count, bifurcates the mobility header. The fourth most important variable, hypertension history, bifurcates the ECOG header. Alternating between rows and columns in a similar manner populates row and column headers with all variables of the numerical computer model. The row header predictors have the predictor level with the favorable outcome on top, and the column header predictors have the predictor level with the favorable outcome to the right, in embodiments. An exemplary prediction matrix with row and column headers created in this manner is illustrated in FIG. 3G.

The above steps are used to generate a blank matrix with column and row headers, in embodiments. To populate these blank cells with the appropriate probability values, the numerical computer model is used to compute the probabilities for every possible combination of patient input values. The probabilities are then inserted into the prediction matrix. Exemplary SAS code to generate data for insertion into the section of the matrix where mobility=0 (No problem in walking about) is as follows:

```
options orientation=portrait;
%let sitevar=8; *Number of blocks;
%let ptsvar=64; *number of cells;
%let blocksize=8; *number of cells per block;
%let ptspersite=%sysevalf(&ptsvar/&sitevar);
%let blockspersite=%sysevalf(&ptspersite/&blocksize,ceil);
%put &ptspersite;
proc plan ;
    factors block=&sitevar ordered pt=&blocksize ordered
/noprint;
    output out=rsched;
run;
proc sort data=rsched;by block;run;
data rsched1;;
    set rsched;
    mobf=0; *Can be changed to 0 1 or 2;
    *mhecogynn=0; *Can be changed to 0 or 1;
    cell + 1;
    if first._n_ then cell = 1;
run;
data rsched1;
    set rsched1;
        if block in (1 2 3 4) then mhecogynn=1;
        if block in (5 6 7 8) then mhecogynn=0;
            if block in (1 2 5 6) then mhhyn=1;
            if block in (3 4 7 8) then mhhyn=0;
            if block in (1 3 5 7) then agen=1;
            if block in (2 4 6 8) then agen=0;
            if pt in (1 2 3 4) then plat_ct=0;
            if pt in (5 6 7 8) then plat_ct=1;
                if pt in (1 2 5 6) then issstagen=0;
                if pt in (3 4 7 8) then issstagen=1;
                if pt in (1 3 5 7) then creat=0;
                if pt in (2 4 6 8) then creat=1;
run;
data covals;
    set rsched1;
    drop pt block;
run;
proc sort data=covals;by cell;run;
data est2;
    set est1;
    keep parm estimate;
run;
***************Transpose estimate*******************;
proc transpose data=est2 out=est3;
    id parm;
run;
*Macro to rename variable so that we can merge the transposed
data set with the main dataset covals;
%macro rename1(oldvarlist, newvarlist);
    %let k=1;
    %let old = %scan(&oldvarlist, &k);
    %let new = %scan(&newvarlist, &k);
        %do %while(("&old" NE "") & ("&new" NE ""));
        rename &old = &new;
            %let k = %eval(&k + 1);
            %let old = %scan(&oldvarlist, &k);
            %let new = %scan(&newvarlist, &k);
        %end;
%mend;
data est3;
    set est3;
    drop _NAME_ ;
    %rename1(agen issstagen mhecogynn mhhyn plat_ct creat mobf,
    agenm issstagem mhecogynm mhhynm plat_ctm creatm mobfm);
run;
data est3b;
set est3;
```

-continued

```
do cell=1 to 64; /*Change to ptsvar number above in this case
ptsvar=32*/
    output;
    end;
run;
proc sort data=est3b; by cell; run;
proc sort data=covals; by cell; run;
data covals1;
  merge covals est3b;
  by cell;
run;
proc sort data=covals1;by cell; run;
*To sum Beta for each cell;
data covals2;
  set covals1;
  Intercept1=intercept;
  agens=agenm*agen;
  issstages=issstagem*issstagen;
  mhecogyns=mhecogynm*mhecogvnn;
  *mhdiabns=mhdiabnm*mhdiabn;
  mhhyns=mhhynm*mhhyn;
  creats=creatm*creat;
  *mhsolynns=mhsolynnm*mhsolynn;
  *calciums=calciumm1*calcium;
  plat_cts=plat_ctm*plat_ct;
  mobfs=mobfm*mobf;
  *agdiab=agenmhdiabnm1*agenmhdiabn;
  *pltmob=plat_ctmobfm1*plat_ctmobf;
  sumbeta=agens+issstages+mhecogyns+mhhyns+plat_cts+creats+mobfs;
run;
*To calculate the Predicted Probability for each cell;
data pred;
  set covals2;
  x=Intercept1 + sumbeta;
  xy=1+exp(-x);
  prob=1/xy;
run;
proc sort data=pred;by cell;run;
proc sort data=rsched1;by cell;run;
data all;
  merge pred rsched1;
  by cell;
  keep cell agen issstagen mhecogynn plat_ct mhhyn mobf creat pt
block prob;
  format prob percent10.;
run;
proc print data=all;run;
proc print data=all;var cell prob;run;
```

In the exemplary prediction matrix of FIG. 3G, smaller blocks are used within the larger blocks with factors which have succeeding smaller effects. Numeric values in the matrix are the probabilities of mortality within 180 days, as generated using the numerical computer model described herein.

The generation of an exemplary prediction matrix corresponding to the 1/2/3/4/5-year-mortality numerical computer model will now be described. Steps similar to those described above for generating a blank matrix are used. To populate these blank cells with appropriate probability values, the numerical computer model is used to compute the probabilities for every possible combination of patient input values. Exemplary SAS code to implement this starts with SAS PROC PLAN code, and a dataset "covals" is generated. This dataset contains the combinations of the levels of the predictors along with the mapping to cells in the matrix. To generate the probabilities for filling the matrix, the exemplary code below uses the covals dataset in the baseline statement of the SAS PHREG procedure to generate survival probabilities at every event time in the registry along with confidence intervals. To obtain the survival probability beyond three years, the data records corresponding to event time closest to and less than the three-year time-point (1095 days) are retained. The prediction of survival beyond three years for each predictor combination is estimated as the average of the corresponding 3 year survivals from each of the imputations. In embodiments in which the variables shown in FIG. 3F-1 are considered, this is implemented in the exemplary SAS code below:

```
proc phreg data=Edeathm2;
  model dur*death(0) = agen issstagen mhecogynn mhdiabn creat
  plat_ct solitary_plasmacytoma mobf gp_17p_ad triplet_therapy
  /ties=efron;
    baseline out=a covariates=covals survival=s lower=lcl
    upper=ucl/nomean;
    by _Imputation_;
run;
```

In embodiments in which the variables shown in FIG. 3F-2 are considered, generating the prediction of survival beyond three years for filling the matrix is implemented in the exemplary SAS code below:

```
proc phreg data=Edeathm2;
  model dur*death(0) = agen issstagen mhecogynn mhdiabn creat
  plat_ct mhsolynn mobf gp_17p_ad gp_hyper_ad novelf /ties=efron;
    baseline out=a covariates=covals survival=s lower=lcl
    upper=ucl/nomean;
    by _Imputation_;
run;
```

To illustrate exemplary prediction matrices generated using the 1/2/3/4/5-year-mortality numerical computer model, reference is made to FIGS. 3H-1, 3H-2, 3H-3, 3I-1, 3I-2, and 3I-3. FIGS. 3H-1, 3H-2, and 3H-3 collectively illustrate an exemplary prediction matrix of survival probability beyond three years for patients having an age that is less than or equal to 75 years, and FIGS. 3I-1, 3I-2, and 3I-3 collectively illustrate an exemplary prediction matrix of survival probability beyond three years for patients having an age that is greater than 75 years. As seen in these figures, the 1/2/3/4/5-year-mortality numerical computer model may consider the variables listed in FIG. 3F-1. In embodiments, these variables are based on the patient's mobility, ECOG performance status, ISS stage, Del 17P status, platelet count, triplet therapy use, renal insufficiency status (e.g., whether serum creatinine is greater than 2 mg/dL), age, diabetes history, and whether the patient has solitary plasmacytoma.

To illustrate additional exemplary prediction matrices generated using the 1/2/3/4/5-year-mortality numerical computer model, reference is made to FIGS. 3J-1, 3J-2, 3J-3, 3K-1, 3K-2, and 3K-3. FIGS. 3J-1, 3J-2, and 3J-3 collectively illustrate an exemplary prediction matrix of survival probability beyond three years for patients having an age that is greater than 75 years, and FIGS. 3K-1, 3K-2, and 3K-3 collectively illustrate an exemplary prediction matrix of survival probability beyond three years for patients having an age that is less than or equal to 75 years. As seen in these figures, the 1/2/3/4/5-year-mortality numerical computer model may consider the variables listed in FIG. 3F-2. In embodiments, these variables are based on the patient's mobility, ECOG performance status, ISS stage, Del 17P status, platelet count, novel therapy use, renal insufficiency status (e.g., whether serum creatinine is greater than 2 mg/dL), age, diabetes history, and whether the patient has extramedullary plasmacytoma and hyperdiploidy.

With reference again to FIG. 3A, at 316, the first and second computer models are validated. Each of the first and second computer models may be validated with both an "internal" validation procedure and an "external" validation procedure. The validation of the first computer model used in generating a probability that a patient diagnosed with multiple myeloma will die within 180 days will now be described. In some embodiments, internal validation involves the splitting of the dataset into test and training samples, and the model obtained in the training sample is evaluated in the test sample. Better estimates of validation indices may be obtained when they are obtained through analysis of repeated random splits into test and training samples, a process referred to as bootstrap re-sampling. The validation index used in embodiments to measure the predictive ability of the computer model is Harrell's C-Index. This index is interpretable as a concordance probability, i.e., the probability that a randomly selected pair of patients, one with a poorer survival outcome than the other, will be correctly differentially identified based on inputting the two patients' baseline prognostic characteristics in the fitted model. To compute the index, each of the 10 imputed datasets is imputed into R software, and the following R code is executed for each dataset for 100 bootstrap sample pairs:

```
library("rms")
Imputation # 1
f <- lrm(d180 ~
age+iss+ecog+hyptension+platcount+mobility+creatine, data =
impt1log, x=TRUE, y=TRUE)
validate(f, B=100, dxy = TRUE)
```

This R script above provides the Somer's D statistic Dxy. The concordance probability for each imputation can be computed as C-Index=0.5*|Dxy|+0.5. Training datasets may have better predictive ability due to the possibility of over fitting the model to the data, and the training optimism adjusted concordance probability adjusts for this bias. In the multiple imputation context, the concordance probability is computed as the average of the adjusted concordance probabilities from each imputation. For the logistic model used in the generation of the first computer model (e.g., computer model used in predicting 180-day mortality), the concordance probability may be identical to the area under the receiver operating characteristic (ROC) curve for the model, and confidence intervals can therefore be computed using expressions developed for determining this area under the curve. The percent reduction in the concordance probability for the test samples compared to the training samples is 2.53% in some embodiments for the logistic model, indicating the unlikelihood of an overfitted model. The training optimism adjusted concordance probability of the fitted logistic model is estimated at 74.3% (95% CI: 68.7,80.0), in embodiments. A concordance probability significantly greater than 50% is indicative of a good predictive model.

External validation may be a measure of how well a computer model (e.g., a computer model derived from data from a registry, as described above) works for an additional, independent external dataset. The external dataset may thus comprise additional, independent data not used in the training of the computer model. In embodiments, the external data is from the "FIRST" multiple myeloma clinical study (N=1623). This study was a phase III, randomized, open-label, 3-Arm study to determine the efficacy and safety of lenalidomide (Revlimid) plus low-dose dexamethasone when given until progressive disease or for 18 four-week cycles versus the combination of Melphalan, Prednisone, and Thalidomide given for 12 six-week cycles in patients with previously untreated multiple myeloma who are either 65 years of age or older or not candidates for stem cell transplantation.

In performing the external validation for the first computer model used in generating a probability that a patient diagnosed with multiple myeloma will die within 180 days, the seven variables used in the logistic model may be collected in the FIRST study data. These variables, as well as mortality within 180 days, may be extracted from the FIRST database. Then, the probability of mortality within 180 days was computed for the FIRST data using the first computer model and compared against actual outcomes in the FIRST study. This may be achieved using the R package rms with the following code:

```
library(rms)
phat <- 1/(1+exp(-(-4.543656+(0.883258*logist$mobf
+0.673436*logist$mhhyn+1.359005*logist$mhecogynn+0.617535*logist
$issstage+0.533151*logist$agen+0.830696*logist$plat_ct+0.466740
*logist$creat))))
val.prob(phat, logist$dthbf180, xlab="Predicted Probability of
Death Before 180 Days ", ylab=" Actual Probability of Death
Before 180 Days ", lim=c(0,1.0), legendloc = c(0.75,0.15), m=
30, cex = 0.7)
```

In embodiments, the concordance probability of the first computer model is 71.83% (95% CI: 66.2, 77.4), which compares favorably to the 74.3% determined in the internal validation. These results show that the first computer model may be relatively portable (e.g., the first computer model may work relatively well on a variety of different datasets). As is evident from the description above, the external validation procedure may include validating the first computer model with testing using additional independent data (e.g., data from the "FIRST" study) not used in the training of the first computer model.

The validation of the second computer model used in generating a probability that a patient diagnosed with multiple myeloma will die within 1, 2, 3, 4, or 5 years will now be described. Internal validation for the second computer model may involve bootstrap re-sampling of 100 test and training datasets and the computation of concordance probabilities. In embodiments in which the ten variables shown in FIG. 3F-1 are considered, to compute this concordance index, each of the 10 imputed datasets is imported into the R software, and the following R code is executed:

```
library("rms")
Imputation # 1
f <- cph(formula=Surv(dur,death) ~
age+iss+ecog+diabetes+creatine+platcount+solitary_plasmacytoma+
mobility+triplet+del17p, data = impt1dt, x=TRUE, y=TRUE, surv =
T)
validate(f,B=100, dxy =TRUE)
```

In embodiments in which the eleven variables shown in FIG. 3F-2 are considered, to compute this concordance index, each of the 10 imputed datasets is imported into the R software, and the following R code is executed:

```
library("rms")
Imputation # 1
f <- cph(formula=Surv(dur,death) ~
age+iss+ecog+diabetes+creatine+platcount+plasmacytoma+mobility+
novel+del17p+hyperploid, data = impt1dt, x=TRUE, y=TRUE, surv =
T)
validate(f,B=100, dxy =TRUE)
```

In embodiments, the percent reduction in the concordance probability for the test samples compared to the training samples is 0.94% for the second computer model, indicating the unlikelihood of an over-fitted model. The training optimism adjusted concordance probability of the second computer model is estimated at 69.5% (95% CI: 66.6, 72.4), in embodiments. A concordance probability significantly greater than 50% may be indicative of a good predictive model.

External validation of the second computer model may be conducted to determine how well the second computer model works for data from the FIRST study. In embodiments in which the variables of FIG. 3F-1 are considered, the ten variables used in the second computer model may be collected in the FIRST study data. The ten variables, as well as the survival duration and censoring variables, may be extracted from the FIRST database. Then, the probability of survival beyond 3 years is computed for FIRST data using the second computer model and compared against actual outcomes in the FIRST study. To compute the probability of survival beyond 3 years, SAS code similar to that described above using the actual predictor combinations found in the FIRST study instead of the covals dataset may be utilized. To compare actual outcomes in FIRST to predicted outcomes generated by the model, the following R code may be utilized:

```
library(rms)
surv.obj2 = with(dmm020cox,Surv(time, cens))
w <- rcorr.cens(x=dmm020cox$s,S=surv.obj2)
C <- w['C Index']
se <- w['S.D.']/2
low <- C-1.96*se; hi <- C+1.96*se
library(rms)
S <- Surv(dmm020cox$time, dmm020cox$cens)
if('polspline' %in% row.names(installed.packages( ))) {
w <- val.surv(est.surv=dmm020cox$s, S=S, u=1095,
fun=function(p)log(-log(p)))
plot(w, xlab="Predicted Probability of Surviving Beyond 3 Years",
ylab="Actual Probability of Surviving Beyond 3 Years",
lim=c(.05,1),scat1d.opts=list(nhistSpike=200, side=1))
groupkm(dmm020cox$s, S, m=100, u=1095, p1=TRUE, add=TRUE)
text(0.4,0.95, "C-Index = 0.6787", cex = 0.9)
}
```

In embodiments, the first part of the above code computes the concordance index and 95% CI as 67.8% (66.1, 69.6). In embodiments, the concordance probability compares favorably to 69.5% in the internal validation, thus supporting the portability of the second computer model. As is evident from the description above, the external validation procedure may include validating the second computer model with testing using additional independent data (e.g., data from the "FIRST" study) not used in the training of the second computer model.

In embodiments in which the variables of FIG. 3F-2 are considered, the eleven variables used in the second computer model may be collected in the FIRST study data. The variable '# of novel therapies' has levels defined as >=2 novel therapies or (0,1) novel therapies as part of the induction regimen in first line. Novel therapies being administered in cohort 1 of the registry included the multiple myeloma drugs Revlimid, Pomalidomide, Velcade and Carfilzomib. In the FIRST study, patients were randomized to Revlimid+Dexamethasone continuous, Revlimid+Dexamethasone for 18 months and Melphalan, Prednisone and Thalidomide for 18 months. The first of the three groups was most efficacious and was mapped to the >=2 level and the remaining groups to (0,1) of the novel therapy variable. The eleven variables, as well as the survival duration and censoring variables, may be extracted from the FIRST database. Then, the probability of survival beyond 3 years is computed for FIRST data using the second computer model and compared against actual outcomes in the FIRST study. To compute the probability of survival beyond 3 years, SAS code similar to that described above using the actual predictor combinations found in the FIRST study instead of the covals dataset may be utilized. To compare actual outcomes in FIRST to predicted outcomes generated by the model, R code similar to that described above for the embodiment considering the variables listed in FIG. 3F-1 may be used.

The above description indicates that the first computer model is used in generating a probability that a patient diagnosed with multiple myeloma will die within a relatively short amount of time (e.g., 180 days), while the second computer model is used in generating a probability that a patient diagnosed with multiple myeloma will die within a longer amount of time (e.g., 1, 2, 3, 4, or 5 years). It is noted, however, that in other embodiments, the first and second computer models may be associated with different respective periods of time. Thus, in embodiments, the first computer model may be trained to predict mortality within 3 months of a multiple myeloma diagnosis, and the second computer model may be trained to predict mortality within 6 months of diagnosis. The first and second computer models are trained to predict mortality for various other periods of time, in embodiments.

Figure 4A:
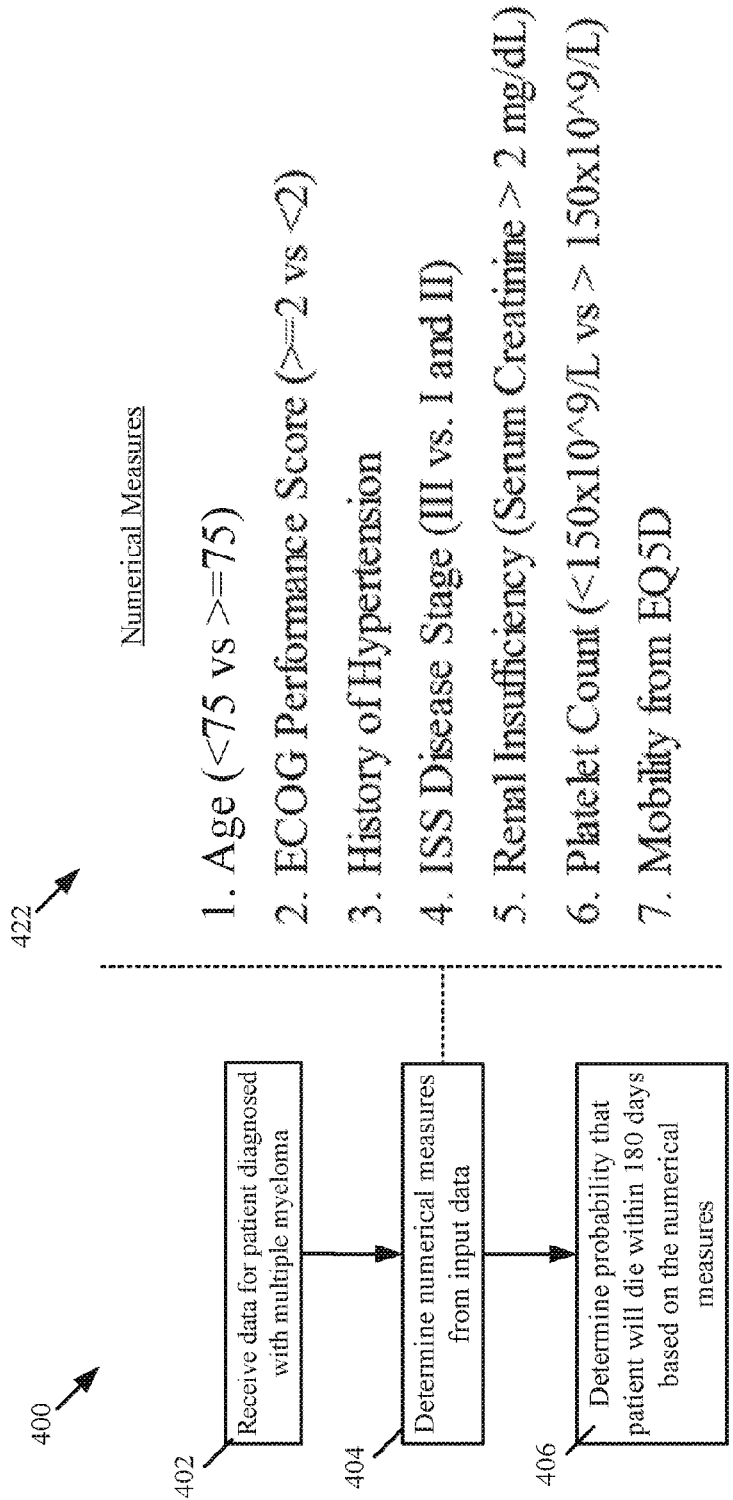
FIGS. 4A and 4B are flowcharts depicting steps of respective exemplary methods for generating a probability that a patient diagnosed with multiple myeloma will die within a predetermined period of time.

FIG. 4A depicts a flowchart 400 including exemplary steps for generating a probability that a patient diagnosed with multiple myeloma will die within 180 days of being diagnosed. This figure further depicts exemplary numerical measures 422 determined from the patient's input data and used in generating the probability. At 402, input data for a patient diagnosed with multiple myeloma is received, where the input data comprises data for multiple variables of a set of patient variables.

At 404, one or more numerical measures are determined by processing the input data. The one or more numerical measures may include numerical measures from the exemplary numerical measures 422 of FIG. 4A. A first numerical measure, "age (<75 years versus ≥75 years)" is indicative of the patient's age and specifically whether the patient's age is greater than or equal to 75. In embodiments, the input data may comprise patient's age in years, and thus, determining the first numerical measure includes comparing the patient's age against "75 years" to determine whether the patient's age is greater than or equal to 75 years. A second numerical measure, "ECOG Performance Score (≥2 versus <2)" is indicative of the patient's performance status and specifically whether the patient's ECOG performance status is greater than or equal to 2. In embodiments, the input data comprises ECOG performance scores in a number format (e.g., 0, 1, 2, etc.), and determining the second numerical measure includes comparing the patient's ECOG performance score against "2" to determine whether the patient's ECOG performance score is greater than or equal to 2.

A third numerical measure, "history of hypertension" is indicative of whether the patient has a history of hypertension. In embodiments, the third numerical measure comprises a Boolean value (e.g., "0" if the patient has no history of hypertension, and "1" if the patient has a history of hypertension, etc.). A fourth numerical measure, "ISS disease stage (III versus I and II)" is indicative of a stage of the patient's multiple myeloma disease and specifically whether the ISS stage of the patient's disease is "III" or whether it is "I or II." A fifth numerical measure, "renal insufficiency (serum creatinine >2 mg/dL)" is indicative of whether the patient has renal insufficiency and specifically whether the patient's serum creatinine is greater than 2 mg/dL. A sixth numerical measure, "platelet count ($<150\times10^9$/L versus $>150\times10^9$/L)" is indicative of the patient's platelet count and specifically whether the platelet count is greater than $150\times10^9$/L. A seventh numerical measure, "mobility from EQ-5D" is indicative of the patient's mobility and specifically the patient's EuroQol five dimensions questionnaire (EQ-5D) mobility score. In embodiments, the seventh numerical measure can take on values of "0," "1," or "2," corresponding to the possible EQ-5D mobility scores. Additional numerical measures not included in the numerical measures 422 of FIG. 4A may be used in other examples.

At 406, a probability that the patient will die within 180 days is determined by applying the numerical computer model to the determined numerical measures.

Figure 4B:
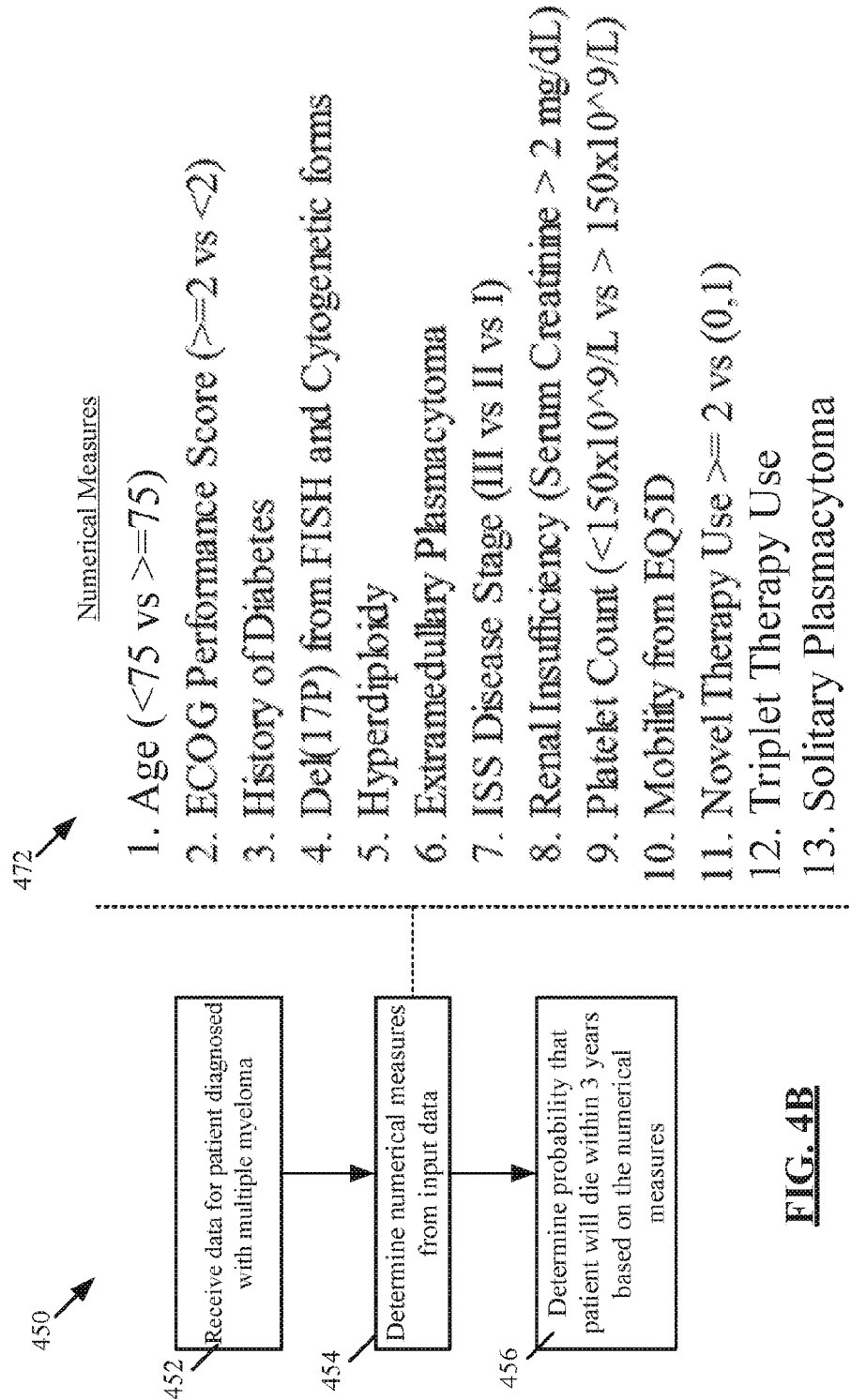

FIG. 4B depicts a flowchart 450 including exemplary steps for generating a probability that a patient diagnosed with multiple myeloma will die within 1 year, 2 years, 3 years, 4 years, or 5 years of being diagnosed. This figure further depicts exemplary numerical measures 472 determined from the patient's input data and used in generating the probability. At 452, input data for a patient diagnosed with multiple myeloma is received, where the input data comprises data for multiple variables of a set of patient variables.

At 454, one or more numerical measures are determined by processing the input data. The one or more numerical measures may include numerical measures from the exemplary numerical measures 472 of FIG. 4B. A first numerical measure, "age (<75 years versus ≥75 years)" is indicative of the patient's age and specifically whether the patient's age is greater than or equal to 75 years. A second numerical measure, "ECOG Performance Score (≥2 versus <2)" is indicative of the patient's performance status and specifically whether the patient's ECOG performance status is greater than or equal to 2. A third numerical measure, "history of diabetes" is indicative of whether the patient has a history of diabetes. In embodiments, the third numerical measure comprises a Boolean value (e.g., "0" if the patient has no history of diabetes and "1" if the patient has a history of diabetes, etc). A fourth numerical measure "Del(17P) from FISH and cytogenetic forms" is indicative of whether the patient has a deleted chromosome 17. A fifth numerical measure "hyperdiploidy" indicates whether the patient has hyperdiploidy. A sixth numerical measure "extramedullary plasmacytoma" indicates whether the patient has extramedullary plasmacytoma.

A seventh numerical measure, "ISS disease stage (III versus II versus I)" is indicative of a stage of the patient's multiple myeloma disease and specifically whether the ISS stage of the patient's disease is "III," "II," or "I." An eighth numerical measure, "renal insufficiency (serum creatinine >2 mg/dL)" is indicative of whether the patient has renal insufficiency and specifically whether the patient's serum creatinine is greater than 2 mg/dL. A ninth numerical measure, "platelet count ($<150\times10^9$/L versus $>150\times10^9$/L)" is indicative of the patient's platelet count and specifically whether the platelet count is greater than $150\times10^9$/L. A tenth numerical measure, "mobility from EQ-5D" is indicative of the patient's mobility and specifically the patient's EuroQol five dimensions questionnaire (EQ-5D) mobility score. In embodiments, the tenth numerical measure can take on values of "0," "1," or "2," corresponding to the possible EQ-5D mobility scores. An eleventh numerical measure, "novel therapy use (≥2 versus (0, 1)" is indicative of a number of novel therapies that the patient has used and specifically whether the number is greater than or equal to 2.

A twelfth numerical measure, "triplet therapy use" is indicative of whether the patient has used triplet therapy. A thirteenth numerical measure, "solitary plasmacytoma" indicates whether the patient has solitary plasmacytoma. Additional numerical measures not included in the numerical measures 472 of FIG. 49 may be used in other examples.

At 456, a probability that the patient will die within 1 year, 2 years, 3 years, 4 years, or 5 years is determined by applying the numerical computer model to the numerical measures. In comparing FIGS. 4A and 4B, it can be seen that the exemplary numerical measures 422 used in generating the probability that the patient will die within 180 days differ from the exemplary numerical measures 472 used in generating the probability that the patient will die within 1 year, 2 years, 3 years, 4 years, or 5 years. As described herein, using the techniques of the present disclosure, reference data is processed to automatically determine a set of variables (e.g., predictors) to be used in a numerical computer model. In embodiments, the variables determined via the processing of the reference data vary based on the time frame considered (e.g., some predictors are valid for predicting whether the patient will die within 180 days but not 1 year, 2 years, 3 years, 4 years, or 5 years, and vice versa. This reflects that early mortality (e.g., mortality within 180 days of diagnosis lay have a different etiology than later mortality (e.g., mortality within 1 year, 2 years, 3 years, 4 years, or 5 years of diagnosis), with co-morbidities dominating the former and disease factors more relevant for the latter.

Figure 5:
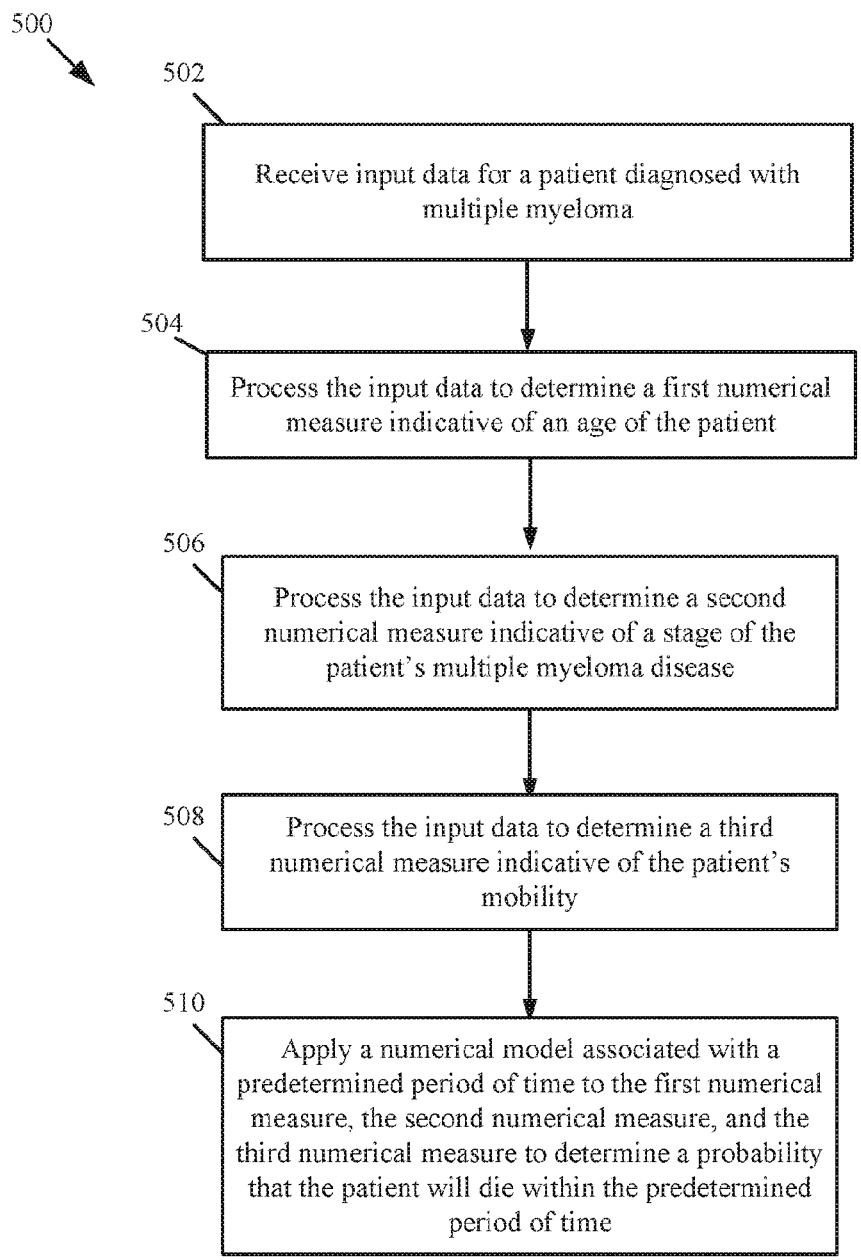
FIG. 5 is a flowchart depicting steps of an exemplary method for generating a probability that a patient diagnosed with multiple myeloma will die within a predetermined period of time.

FIG. 5 is a flowchart 500 depicting steps of an exemplary method for generating a probability that a patient diagnosed with multiple myeloma will die within a predetermined period of time. At 502, input data for a patient diagnosed with multiple myeloma is received. The input data comprises data for multiple variables of a set of patient variables. At 504, the input data is processed to determine a first numerical measure indicative of an age of the patient. At 506, the input data is processed to determine a second numerical measure indicative of a stage of the patient's multiple myeloma disease. At 508, the input data is processed to determine a third numerical measure indicative of the patient's mobility.

At 510, a numerical computer model associated with a predetermined period of time is applied to the first numerical measure, the second numerical measure, and the third numerical measure to determine a probability that the patient will die within the predetermined period of time. The numerical computer model includes a first variable and an associated first weighting factor, the first variable receiving a value of the first numerical measure. The numerical computer model also includes a second variable and an associated second weighting factor, the first variable receiving a value of the second numerical measure. The numerical computer model further includes a third variable and an associated third weighting factor, the third variable receiving a value of the third numerical measure. The application of the numerical computer model at this stage may involve the actual variable selection, training and configuration of the computer model. Alternatively, the application of the numerical computer model at this stage may involve accessing pre-calculated results the numerical computer model and applying rule-based selection criteria based on the particular numerical measures to select the corresponding mortality value(s) applicable from pre-calculated data from the numerical computer model applicable to the particular numerical measures for the associated variables.

As described above, the present disclosure provides computer-based techniques for predicting likelihoods of near-term and long-term mortality in patients diagnosed with multiple myeloma. However, the computer-based techniques described herein may be applied to other cancers and other diseases beyond multiple myeloma through application of regression analysis for selecting suitable patient variables for multiple computer models, training the computer models with suitable patient reference data to determine weighting factors associated with the variables for the models for desired mortality time periods, updating the computer models with the appropriate weighting factors, and validating the computer models for use in making actual predictions.

Figure 6A:
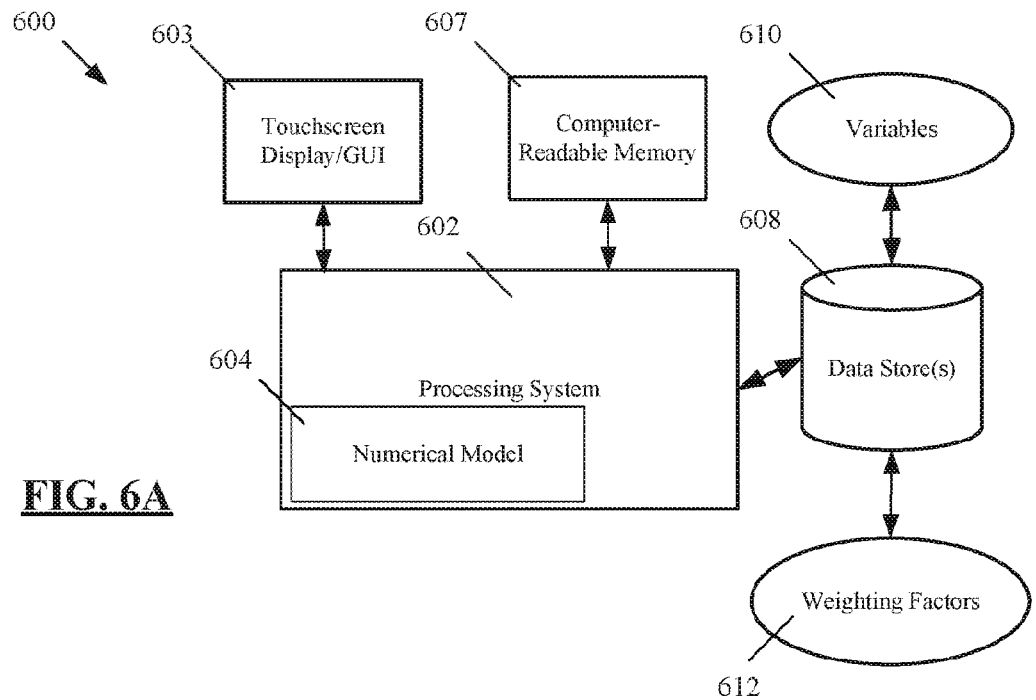
FIGS. 6A, 6B, and 6C depict exemplary systems for implementing the techniques described herein.
Figure 6B:
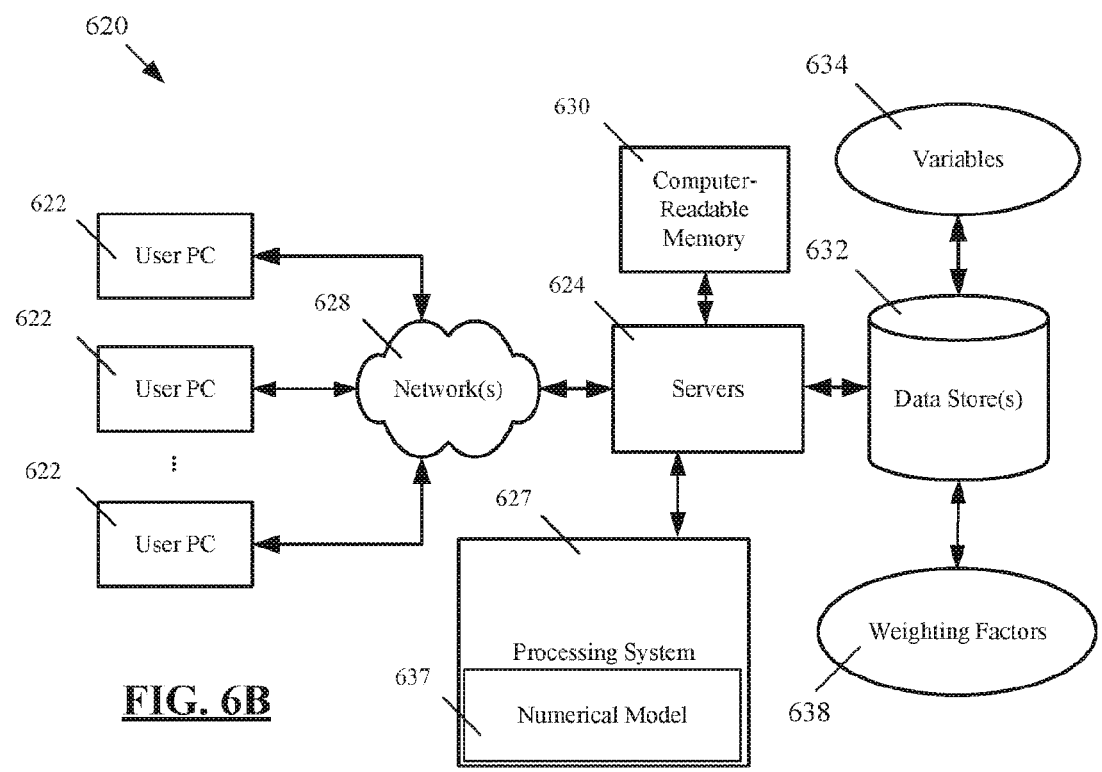
Figure 6C:
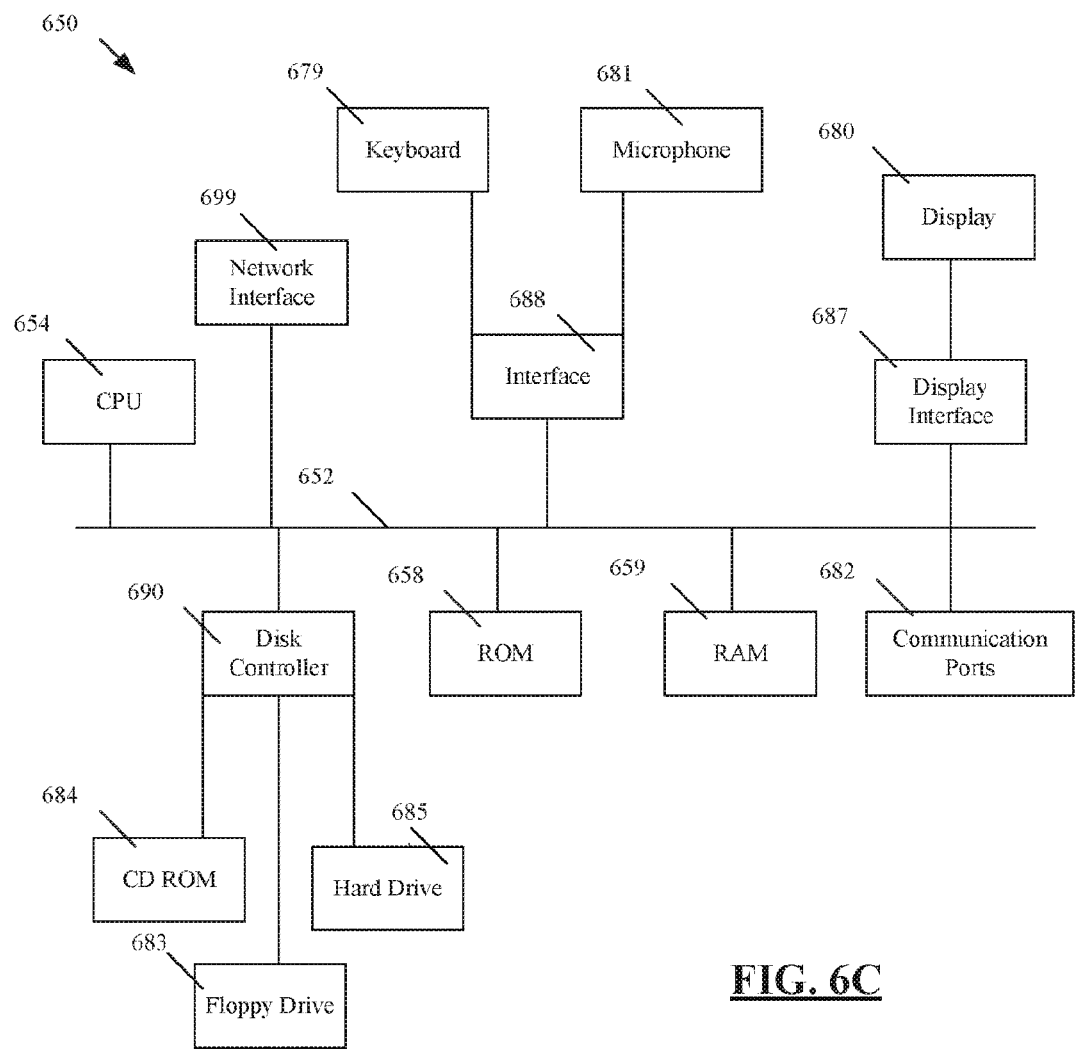

FIGS. 6A, 6B, and 6C depict exemplary systems for implementing the techniques described herein. For example, FIG. 6A depicts an exemplary system 600 that includes a standalone computer architecture where a processing system 602 (e.g., one or more computer processors located in a given computer or in multiple computers that may be separate and distinct from one another) includes a numerical computer model 604 being executed on the processing system 602. For instance, the processing system 602 represented in FIG. 6A may be that of a touchscreen smartphone, a touchscreen tablet, a laptop PC, a desktop PC, etc. Accordingly, the processing system 602 may communicate with a touchscreen display or GUI 603 to display outputs to the user and receive inputs from the user. The processing system 602 has access to a computer-readable memory 607 in addition to one or more data stores 608. The one or more data stores 608 may include variables 610 as well as weighting factors 612. The processing system 602 may be a distributed parallel computing environment, which may be used to handle very large-scale data sets.

FIG. 6B depicts a system 620 that includes a client-server architecture. One or more user PCs 622 access one or more servers 624 running a numerical computer model 604 on a processing system 627 via one or more networks 628. The one or more servers 624 may access a computer-readable memory 630 as well as one or more data stores 632. The one or more data stores 632 may include variables 634 as well as weighting factors 638.

FIG. 6C shows a block diagram of exemplary hardware for a standalone computer architecture 650, such as the architecture depicted in FIG. 6A that may be used to include and/or implement the program instructions of system embodiments of the present disclosure. A bus 652 may serve as the information highway interconnecting the other illustrated components of the hardware. A processing system 654 labeled CPU (central processing unit) (e.g., one or more computer processors at a given computer or at multiple computers), may perform calculations and logic operations required to execute a program. A non-transitory processor-readable storage medium, such as read only memory (ROM) 658 and random access memory (RAM) 659, may be in communication with the processing system 654 and may include one or more programming instructions for performing methods (e.g., algorithms) for constructing a numerical computer model to generate a probability that a patient diagnosed with multiple myeloma will die within a predetermined period of time. Optionally, program instructions may be stored on a non-transitory computer-readable storage medium such as a magnetic disk, optical disk, recordable memory device, flash memory, or other physical storage medium.

In FIGS. 6A, 6B, and 6C, computer readable memories 607, 630, 658, 659 or data stores 608, 632, 683, 684 may include one or more data structures for storing and associating various data used in the exemplary systems for constructing a numerical computer model to generate a probability that a patient diagnosed with multiple myeloma will die within a predetermined period of time. For example, a data structure stored in any of the aforementioned locations may be used to store data relating to variables and/or weighting factors. A disk controller 690 interfaces one or more optional disk drives to the system bus 652. These disk drives may be external or internal floppy disk drives such as 683, external or internal CD-ROM, CD-R, CD-RW or DVD drives such as 684, or external or internal hard drives 685. As indicated previously, these various disk drives and disk controllers are optional devices.

Each of the element managers, real-time data buffer, conveyors, input file processor, database index shared access memory loader, reference data buffer and data managers may include a software application stored in one or more of the disk drives connected to the disk controller 690, the ROM 658 and/or the RAM 659. The processor 654 may access one or more components as required.

A display interface 687 may permit information from the bus 652 to be displayed on a display 680 in audio, graphic, or alphanumeric format. Communication with external devices may optionally occur using various communication ports 682.

In addition to these computer-type components, the hardware may also include data input devices, such as a keyboard 679, or other input device 681, such as a microphone, remote control, pointer, mouse and/or joystick. Such data input devices communicate with the standalone computer architecture 650 via an interface 688, in some embodiments. The standalone computer architecture 650 further includes a network interface 699 that enables the architecture 650 to connect to a network, such as a network of the one or more networks 628.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein and may be provided in any suitable language such as C, C−+, JAVA, for example, or any other suitable programming language. Other implementations may also be used, however, such as firmware or even appropriately designed hardware configured to carry out the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, Flash memory, flat files, databases, programming data structures, programming variables, IF-THEN (or similar type) statement constructs, etc.). It is noted that data structures describe formats for use in organizing and storing data in databases, programs, memory, or other computer-readable media for use by a computer program.

The computer components, software modules, functions, data stores and data structures described herein may be connected directly or indirectly to each other in order to allow the flow of data needed for their operations. It is also noted that a module or processor includes but is not limited to a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue f computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or arty equivalent storage medium. The machine-readable medium can alternatively or additionally store such machine instructions in a transient manner, such as for example as would a processor cache or other random access memory associated with one or more physical processor cores.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer-implemented method comprising:
receiving data characterizing health of a patient diagnosed with multiple myeloma;
generating, using the received data and a first computer model, a first probability that the patient will die within a first predetermined period of time;
generating, using the received data and a second computer model, a second probability that the patient will die within a second predetermined period of time, the second predetermined period of time being different from the first predetermined period of time, the first computer model being trained separately from the second computer model, and
displaying the first probability and the second probability in a graphical user interface;
wherein the first computer model and the second computer model are generated and validated by:
receiving reference data for a plurality of patients diagnosed with multiple myeloma, the reference data comprising for respective patients of the plurality of patients (i) data for variables of a set of patient variables, and (ii) survival data indicative of an amount of time between the patient's cancer diagnosis and the patient's death or between the cancer diagnosis and a date at which the patient is last known to be alive;
generating multiple candidate computer models comprising different combinations of the variables of the set of patient variables, each of the candidate computer models including multiple weighting factors associated with the variables and having missing data, each variable of each candidate computer model having an associated weighting factor, the generating comprising imputing the missing data from the multiple candidate computer models;
conducting multiple computerized numerical regression analyses for the multiple candidate computer models based on the data for the variables and the survival data to determine first selected variables and second selected variables from the set of patient variables, the first selected variables satisfying one or more selection criteria to be deemed predictive of mortality for a first predetermined period of time for patients diagnosed with multiple myeloma and the second selected variables satisfying one or more selection criteria deemed to be predictive of mortality for a second predetermined period of time for patients diagnosed with multiple myeloma;

generating the first computer model comprising a combination of variables of the first selected variables and first weighting factors associated with the respective first selected variables;

generating the second computer model comprising a combination of variables of the second selected variables and second weighting factors associated with the respective selected second variables;

training the first computer model and the second computer model with a processing system using the reference data to determine numerical values for the respective first and second weighting factors;

updating the first computer model and the second computer model to include the determined numerical values for the first weighting factors and the second weighting factors for each selected variable of the first and second selected variables such that the first computer model is configured to generate probability data that a patient satisfying certain first selectable criteria will die within the first predetermined period of time and such that the second computer model is configured to generate probability data that a patient satisfying certain second selectable criteria will die within the second predetermined period of time; and computing indices for the respective first and second computer models by randomly sampling from test and training data, applying the first and second computer models to the randomly sampled data, and calculating the indices based on outputs of the models, wherein each of the indices is a numerical measure of the predictive ability of the associated model.

2. The computer-implemented method of claim 1, wherein the received data consists of: a first variable indicative of the patient's age, a second variable indicative of the patient's Eastern Cooperative Oncology Group (ECOG) performance status, a third variable indicative of the patient's history of hypertension, a fourth variable indicative of a stage of the patient's multiple myeloma disease, a fifth variable indicative of whether the patient has renal insufficiency, a sixth variable indicative of the patient's platelet count, and a seventh variable indicative of the patient's mobility.

3. The computer-implemented method of claim 1, wherein the second selected variables comprise a first variable indicative of the patient's age, a second variable indicative of the patient's mobility, a third variable indicative of the patient's Del(17P) from FISH and cytogenetic forms, a fourth variable indicative of a stage of the patient's multiple myeloma disease, a fifth variable indicative of the patient's platelet count, a sixth variable indicative of whether the patient has a history of solitary plasmacytoma, a seventh variable indicative of the patient's ECOG performance status, an eighth variable indicative of the patient's history of diabetes, a ninth variable indicative of whether the patient has renal insufficiency, and a tenth variable indicative of whether the patient has used triplet therapy.

4. The computer-implemented method of claim 1, comprising validating the first and second computer models with testing using additional independent data not used in training the first and second computer models.

5. The computer-implemented method of claim 1, comprising providing selectable input fields in the graphical user interface adapted to receive input information from a user, the processing system processing the input information and numerical data of at least one of the first computer model and the second computer model so as to render to the user a probability that the patient will die within at least one of the first predetermined time and the second predetermined time.

6. The computer-implemented method of claim 1, wherein the determining of the first selected variables and the second selected variables comprises:

analyzing each variable of the set of patient variables independently of the other variables to determine variables that have a degree of univariate association with patient death within the first predetermined period of time that is above a threshold; and analyzing each variable of the set of patient variables independently of the other variables to determine variables that have a degree of univariate association with patient death within the second predetermined period of time that is above the threshold.

7. The computer-implemented method of claim 1, wherein the training of the first computer model and the second computer model comprises:

processing the reference data to determine, for patients represented in the reference data, numerical measures for respective variables of the first selected variables, and conducting a first computerized numerical regression analysis based on the determined numerical measures to determine the first weighting factors; and processing the reference data to determine, for patients represented in the reference data, numerical measures for respective variables of the second selected variables, and conducting a second computerized numerical regression analysis based on the determined numerical measures to determine the second weighting factors.

8. The computer-implemented method of claim 1, further comprising:

determining variables of the first and second selected variables for which an amount of data missing from the reference data is above a predetermined amount; and prior to the training of the first and second computer models, performing a Monte Carlo-based imputation procedure to impute data for the variables having the amount of data missing above the predetermined amount.

9. A system for constructing and validating a numerical model configured to generate a probability that a patient diagnosed with multiple myeloma will die within a predetermined period of time, the system comprising:

a processing system; and computer-readable memory in communication with the processing system encoded with instructions for commanding the processing system to execute steps comprising:

receiving data characterizing health of a patient diagnosed with multiple myeloma;

generating, using the received data and a first computer model, a first probability that the patient will die within a first predetermined period of time;

generating, using the received data and a second computer model, a second probability that the patient will die within a second predetermined period of time, the second predetermined period of time being different from the first predetermined period of time, the first computer model being trained separately from the second computer model; and displaying the first probability and the second probability in a graphical user interface;

wherein the first computer model and the second computer model are generated and validated by:

receiving reference data for a plurality of patients diagnosed with multiple myeloma, the reference data comprising for respective patients of the plurality of patients (i) data for variables of a set of patient variables, and (ii) survival data indicative of an amount of time between the patient's cancer diagnosis and the patient's death or between the cancer diagnosis and a date at which the patient is last known to be alive;

generating multiple candidate computer models comprising different combinations of the variables of the set of patient variables, each of the candidate computer models including multiple weighting factors associated with the variables, each variable of each candidate computer model having an associated weighting factor;

conducting multiple computerized numerical regression analyses for the multiple candidate computer models based on the data for the variables and the survival data to determine first selected variables and second selected variables from the set of patient variables, the first selected variables satisfying one or more selection criteria to be deemed predictive of mortality for a first predetermined period of time for patients diagnosed with multiple myeloma and the second selected variables satisfying one or more selection criteria deemed to be predictive of mortality for a second predetermined period of time for patients diagnosed with multiple myeloma;

generating the first computer model comprising a combination of variables of the first selected variables and first weighting factors associated with the respective first selected variables;

generating the second computer model comprising a combination of variables of the second selected variables and second weighting factors associated with the respective selected second variables;

training the first computer model and the second computer model using the reference data to determine numerical values for the respective first and second weighting factors;

updating the first computer model and the second computer model to include the determined numerical values for the first weighting factors and the second weighting factors for each selected variable of the first and second selected variables such that the first computer model is configured to generate probability data that a patient satisfying certain first selectable criteria will die within the first predetermined period of time and such that the second computer model is configured to generate probability data that a patient satisfying certain second selectable criteria will die within the second predetermined period of time; and computing indices for the respective first and second computer models by randomly sampling from test and training data, applying the first and second computer models to the randomly sampled data, and calculating the indices based on outputs of the models, wherein each of the indices is a numerical measure of the predictive ability of the associated model.

10. The computer-implemented system of claim 9, wherein the first selected variables comprise a first variable indicative of the patient's age, a second variable indicative of the patient's ECOG performance status, a third variable indicative of the patient's history of hypertension, a fourth variable indicative of a stage of the patient's multiple myeloma disease, a fifth variable indicative of whether the patient has renal insufficiency, a sixth variable indicative of the patient's platelet count, and a seventh variable indicative of the patient's mobility.

11. The computer-implemented system of claim 9, wherein the second selected variables comprise a first variable indicative of the patient's age, a second variable indicative of the patient's mobility, a third variable indicative of the patient's Del(17P) from FISH and cytogenetic forms, a fourth variable indicative of a stage of the patient's multiple myeloma disease, a fifth variable indicative of the patient's platelet count, a sixth variable indicative of whether the patient has a history of solitary plasmacytoma, a seventh variable indicative of the patient's ECOG performance status, an eighth variable indicative of the patient's history of diabetes, a ninth variable indicative of whether the patient has renal insufficiency, and a tenth variable indicative of whether the patient has used triplet therapy.

12. The computer-implemented system of claim 9, wherein the steps comprise:

validating the first and second computer models with testing using additional independent data not used in training the first and second computer models.

13. The computer-implemented system of claim 9, wherein the steps comprise:

providing a graphical user interface with selectable input fields adapted to receive input information from a user; and processing the input information and numerical data of at least one of the first computer model and the second computer model so as to render to the user a probability that the patient will die within at least one of the first predetermined time and the second predetermined time.

14. The system of claim 9, wherein the determining of the first selected variables and the second selected variables comprises:

analyzing each variable of the set of patient variables independently of the other variables to determine variables that have a degree of univariate association with patient death within the first predetermined period of time that is above a threshold; and analyzing each variable of the set of patient variables independently of the other variables to determine variables that have a degree of univariate association with patient death within the second predetermined period of time that is above the threshold.

15. The system of claim 9, wherein the training of the first computer model and the second computer model comprises:

processing the reference data to determine, for patients represented in the reference data, numerical measures for respective variables of the first selected variables, and conducting a first computerized numerical regression analysis based on the determined numerical measures to determine the first weighting factors; and processing the reference data to determine, for patients represented in the reference data, numerical measures for respective variables of the second selected variables, and conducting a second computerized numerical regression analysis based on the determined numerical measures to determine the second weighting factors.

16. The system of claim 9, wherein the steps further comprise:
determining variables of the first and second selected variables for which an amount of data missing from the reference data is above a predetermined amount; and
prior to the training of the first and second computer models, performing an imputation procedure to impute data for the variables having the amount of data missing above the predetermined amount.

17. A non-transitory computer-readable storage medium comprising computer executable instructions which, when executed, cause a processing system to execute steps comprising:
receiving data characterizing health of a patient diagnosed with multiple myeloma;
generating, using the received data and a first computer model, a first probability that the patient will die within a first predetermined period of time;
generating, using the received data and a second computer model, a second probability that the patient will die within a second predetermined period of time, the second predetermined period of time being different from the first predetermined period of time, the first computer model being trained separately from the second computer model; and
displaying the first probability and the second probability in a graphical user interface;
wherein the first computer model and the second computer model are generated and validated by:
receiving reference data for a plurality of patients diagnosed with multiple myeloma, the reference data comprising for respective patients of the plurality of patients (i) data for variables of a set of patient variables, and (ii) survival data indicative of an amount of time between the patient's cancer diagnosis and the patient's death or between the cancer diagnosis and a date at which the patient is last known to be alive;
generating multiple candidate computer models comprising different combinations of the variables of the set of patient variables, each of the candidate computer models including multiple weighting factors associated with the variables, each variable of each candidate computer model having an associated weighting factor;
conducting multiple computerized numerical regression analyses for the multiple candidate computer models based on the data for the variables and the survival data to determine first selected variables and second selected variables from the set of patient variables, the first selected variables satisfying one or more selection criteria to be deemed predictive of mortality for a first predetermined period of time for patients diagnosed with multiple myeloma and the second selected variables satisfying one or more selection criteria deemed to be predictive of mortality for a second predetermined period of time for patients diagnosed with multiple myeloma;
generating the first computer model comprising a combination of variables of the first selected variables and first weighting factors associated with the respective first selected variables;
generating the second computer model comprising a combination of variables of the second selected variables and second weighting factors associated with the respective selected second variables;
training the first computer model and the second computer model using the reference data to determine numerical values for the respective first and second weighting factors;
updating the first computer model and the second computer model to include the determined numerical values for the first weighting factors and the second weighting factors for each selected variable of the first and second selected variables such that the first computer model is configured to generate probability data that a patient satisfying certain first selectable criteria will die within the first predetermined period of time and such that the second computer model is configured to generate probability data that a patient satisfying certain second selectable criteria will die within the second predetermined period of time; and
computing indices for the respective first and second computer models by randomly sampling from test and training data, applying the first and second computer models to the randomly sampled data, and calculating the indices based on outputs of the models, wherein each of the indices is a numerical measure of the predictive ability of the associated model.

18. The non-transitory computer-readable storage medium of claim 17, wherein the first selected variables comprise a first variable indicative of the patient's age, a second variable indicative of the patient's ECOG performance status, a third variable indicative of the patient's history of hypertension, a fourth variable indicative of a stage of the patient's multiple myeloma disease, a fifth variable indicative of whether the patient has renal insufficiency, a sixth variable indicative of the patient's platelet count, and a seventh variable indicative of the patient's mobility.

19. The non-transitory computer-readable storage medium of claim 17, wherein the second selected variables comprise a first variable indicative of the patient's age, a second variable indicative of the patient's mobility, a third variable indicative of the patient's Del(17P) from FISH and cytogenetic forms, a fourth variable indicative of a stage of the patient's multiple myeloma disease, a fifth variable indicative of the patient's platelet count, a sixth variable indicative of whether the patient has a history of solitary plasmacytoma, a seventh variable indicative of the patient's ECOG performance status, an eighth variable indicative of the patient's history of diabetes, a ninth variable indicative of whether the patient has renal insufficiency, and a tenth variable indicative of whether the patient has used triplet therapy.

20. The non-transitory computer-readable storage medium of claim 17, wherein the steps comprise:
validating the first and second computer models with testing using additional independent data not used in training the first and second computer models.

21. The non-transitory computer-readable storage medium of claim 17, wherein the steps comprise:
providing selectable input fields in the graphical user interface adapted to receive input information from a user; and
processing the input information and numerical data of at least one of the first computer model and the second computer model so as to render to the user a probability that the patient will die within at least one of the first predetermined time and the second predetermined time.

22. The non-transitory computer-readable storage medium of claim 17, wherein the determining of the first selected variables and the second selected variables comprises:
analyzing each variable of the set of patient variables independently of the other variables to determine variables that have a degree of univariate association with patient death within the first predetermined period of time that is above a threshold; and
analyzing each variable of the set of patient variables independently of the other variables to determine variables that have a degree of univariate association with patient death within the second predetermined period of time that is above the threshold.

23. The non-transitory computer-readable storage medium of claim 17, wherein the training of the first computer model and the second computer model comprises:
processing the reference data to determine, for patients represented in the reference data, numerical measures for respective variables of the first selected variables, and conducting a first computerized numerical regression analysis based on the determined numerical measures to determine the first weighting factors; and
processing the reference data to determine, for patients represented in the reference data, numerical measures for respective variables of the second selected variables, and conducting a second computerized numerical regression analysis based on the determined numerical measures to determine the second weighting factors.

24. The non-transitory computer-readable storage medium of claim 17, wherein the steps further comprise:
determining variables of the first and second selected variables for which an amount of data missing from the reference data is above a predetermined amount; and
prior to the training of the first and second computer models, performing an imputation procedure to impute data for the variables having the amount of data missing above the predetermined amount.

25. A computer-implemented method of generating a probability that a patient diagnosed with multiple myeloma will die within a predetermined period of time, the method comprising:
receiving input data for a patient diagnosed with multiple myeloma, the input data comprising data for multiple variables of a set of patient variables;
processing the input data with a processing system to determine a first numerical measure indicative of an age of the patient;
processing the input data with the processing system to determine a second numerical measure indicative of a stage of the patient's multiple myeloma disease;
processing the input data with the processing system to determine a third numerical measure indicative of the patient's mobility;
applying a first numerical model associated with a first predetermined period of time to the first numerical measure, the second numerical measure, and the third numerical measure to determine a first probability that the patient will die within the first predetermined period of time;
applying a second numerical model associated with a second predetermined period of time to the first numerical measure, the second numerical measure, and the third numerical measure to determine a second probability that the patient will die within the second predetermined period of time, the second predetermined period of time being different than the first predetermined period of time, the first computer model being trained separately from the second computer model; and
displaying the first probability and the second probability in a graphical user interface;
wherein the first and second numerical models each include:
a first variable and an associated first weighting factor, the first variable receiving a value of the first numerical measure,
a second variable and an associated second weighting factor, the first variable receiving a value of the second numerical measure, and
a third variable and an associated third weighting factor, the third variable receiving a value of the third numerical measure, wherein the numerical model has an index indicative of the predictive capability of the numerical model, the index being computed by randomly sampling from test and training data, applying the numerical model to the randomly sampled data, and calculating the index based on an output of the numerical model.

26. The computer-implemented method of claim 25, the first and second numerical models include additional variables that receive values of additional numerical measures determined from the input data including one or more numerical measures indicative of one or more of the patient's history of hypertension, ECOG performance status, renal sufficiency, platelet count, history of diabetes, Del (17P) from FISH and cytogenetic forms, solitary plasmacytoma, and triplet therapy use.

27. The computer-implemented method of claim 25, further comprising:
processing the input data with the processing system to determine a fourth numerical measure indicative of the patient's platelet count;
processing the input data with the processing system to determine a fifth numerical measure indicative of whether the patient has renal insufficiency or a history of diabetes or hypertension; and
applying the first and second numerical models to the fourth numerical measure and the fifth numerical measure to determine the first and second probabilities, the first and second numerical models each including
a fourth variable and an associated fourth weighting factor, the fourth variable receiving a value of the fourth numerical measure, and
a fifth variable and an associated fifth weighting factor, the fifth variable receiving a value of the fifth numerical measure.

28. The computer-implemented method of claim 25, further comprising:
processing the input data with the processing system to determine a fourth numerical measure indicative of an ECOG performance status of the patient; and
applying the first and second numerical models to the fourth numerical measure to determine the first and second probabilities, the first and second numerical models each including a fourth variable and an associated fourth weighting factor, the fourth variable receiving a value of the fourth numerical measure.

29. A system for generating a probability that a patient diagnosed with multiple myeloma will die within a predetermined period of time, the system comprising:

a processing system; and computer-readable memory in communication with the processing system encoded with instructions for commanding the processing system to execute steps comprising:

receiving input data for a patient diagnosed with multiple myeloma, the input data comprising data for multiple variables of a set of patient variables;

processing the input data to determine a first numerical measure indicative of an age of the patient;

processing the input data to determine a second numerical measure indicative of a stage of the patient's multiple myeloma disease;

processing the input data to determine a third numerical measure indicative of the patient's mobility;

applying a first numerical model associated with a first predetermined period of time to the first numerical measure, the second numerical measure, and the third numerical measure to determine a first probability that the patient will die within the first predetermined period of time;

applying a second numerical model associated with a second predetermined period of time to the first numerical measure, the second numerical measure, and the third numerical measure to determine a second probability that the patient will die within the second predetermined period of time, the second predetermined period of time being different than the first predetermined period of time, the first computer model being trained separately from the second computer model; and displaying the first probability and the second probability in a graphical user interface;

wherein the first and second numerical models each include:
  a first variable and an associated first weighting factor, the first variable receiving a value of the first numerical measure,
  a second variable and an associated second weighting factor, the first variable receiving a value of the second numerical measure, and
  a third variable and an associated third weighting factor, the third variable receiving a value of the third numerical measure, wherein the numerical model has an index indicative of the predictive capability of the numerical model, the index being computed by randomly sampling from test and training data, applying the numerical model to the randomly sampled data, and calculating the index based on an output of the numerical model.

30. The system of claim 29, the numerical model including additional variables that receive values of additional numerical measures determined from the input data including one or more numerical measures indicative of one or more of the patient's history of hypertension, ECOG performance status, renal sufficiency, platelet count, history of diabetes, Del(17P) from FISH and cytogenetic forms, solitary plasmacytoma, and triplet therapy use.

31. The system of claim 29, wherein the steps further comprise:

processing the input data to determine a fourth numerical measure indicative of the patient's platelet count;

processing the input data to determine a fifth numerical measure indicative of whether the patient has renal insufficiency or a history of diabetes or hypertension; and applying the first and second numerical models to the fourth numerical measure and the fifth numerical measure to determine the first and second probabilities, the first and second numerical models each including
  a fourth variable and an associated fourth weighting factor, the fourth variable receiving a value of the fourth numerical measure, and
  a fifth variable and an associated fifth weighting factor, the fifth variable receiving a value of the fifth numerical measure.

32. The system of claim 29, wherein the steps further comprise:

processing the input data to determine a fourth numerical measure indicative of an ECOG performance status of the patient; and applying the first and second numerical models to the fourth numerical measure to determine the first and second probabilities, the first and second numerical models each including a fourth variable and an associated fourth weighting factor, the fourth variable receiving a value of the fourth numerical measure.

33. A non-transitory computer-readable storage medium for generating a probability that a patient diagnosed with multiple myeloma will die within a predetermined period of time, the computer-readable storage medium comprising computer executable instructions which, when executed, cause a processing system to execute steps comprising:

receiving input data for a patient diagnosed with multiple myeloma, the input data comprising data for multiple variables of a set of patient variables;

processing the input data to determine a first numerical measure indicative of an age of the patient;

processing the input data to determine a second numerical measure indicative of a stage of the patient's multiple myeloma disease;

processing the input data to determine a third numerical measure indicative of the patient's mobility;

applying a first numerical model associated with a first predetermined period of time to the first numerical measure, the second numerical measure, and the third numerical measure to determine a first probability that the patient will die within the first predetermined period of time;

applying a second numerical model associated with a second predetermined period of time to the first numerical measure, the second numerical measure, and the third numerical measure to determine a second probability that the patient will die within the second predetermined period of time, the second predetermined period of time being different than the first predetermined period of time; and displaying the first probability and the second probability in a graphical user interface;

wherein the first and second numerical models each include:
  a first variable and an associated first weighting factor, the first variable receiving a value of the first numerical measure,
  a second variable and an associated second weighting factor, the first variable receiving a value of the second numerical measure, and
  a third variable and an associated third weighting factor, the third variable receiving a value of the third numerical measure, wherein the numerical model has an index indicative of the predictive capability of the numerical model, the index being computed by randomly sampling from test and training data, applying the numerical model to the randomly sampled data, and calculating the index based on an output of the numerical model.

34. The non-transitory computer-readable storage medium of claim 33, the first and second numerical models each include additional variables that receive values of additional numerical measures determined from the input data including one or more numerical measures indicative of one or more of the patient's history of hypertension, ECOG performance status, renal sufficiency, platelet count, history of diabetes, Del(17P) from FISH and cytogenetic forms, solitary plasmacytoma, and triplet therapy use.

35. The non-transitory computer-readable storage medium of claim 33, wherein the steps further comprise:
processing the input data to determine a fourth numerical measure indicative of the patient's platelet count;
processing the input data to determine a fifth numerical measure indicative of whether the patient has renal insufficiency or a history of diabetes or hypertension; and
applying the first and second numerical models to the fourth numerical measure and the fifth numerical measure to determine the first and second probabilities, the first and second numerical models each including
a fourth variable and an associated fourth weighting factor, the fourth variable receiving a value of the fourth numerical measure, and
a fifth variable and an associated fifth weighting factor, the fifth variable receiving a value of the fifth numerical measure.

36. The non-transitory computer-readable storage medium of claim 33, wherein the steps further comprise:
processing the input data to determine a fourth numerical measure indicative of an ECOG performance status of the patient; and
applying the first and second numerical models to the fourth numerical measure to determine the first and second probabilities, the first and second numerical models each including a fourth variable and an associated fourth weighting factor, the fourth variable receiving a value of the fourth numerical measure.

37. The computer-implemented method of claim 1, wherein determining the first selected variables and the second selected variables includes:
performing a first univariate analysis of each variable of the set of patient variables independently of the other variables to determine a first set of variables that have a degree of univariate association with an outcome of patient death within the first predetermined period of time that is above a threshold, the first univariate analysis measuring the outcome with a dichotomous variable in which there are only two possible outcomes;
performing a second univariate analysis of each variable of the set of patient variables independently of the other variables to determine a second set of variables that have a degree of univariate association with an outcome of patient death within the second predetermined period of time that is above the threshold, the second univariate analysis measuring the outcome with a non-dichotomous variable in which there are more than two possible outcomes; and
conducting multiple computerized numerical regression analyses for the multiple candidate computer models based on the data for the first set of variables, the second set of variables, and the survival data to determine the first selected variables and the second selected variables.

* * * * *